United States Patent
Karki et al.

(10) Patent No.: US 8,877,815 B2
(45) Date of Patent: Nov. 4, 2014

(54) SUBSTITUTED CARBAMOYLCYCLOALKYL ACETIC ACID DERIVATIVES AS NEP

(75) Inventors: Rajeshri Ganesh Karki, Somerville, MA (US); Toshio Kawanami, Boston, MA (US); Gary Michael Ksander, Boston, MA (US); Qian Liu, Malden, MA (US); Muneto Mogi, Waltham, MA (US); Nikolaus Schiering, Weil am Rhein (DE); Robert Sun, Natick, MA (US)

(73) Assignee: Novartis AG, Basel (CH)

(*) Notice: Subject to any disclaimer, the term of this patent is extended or adjusted under 35 U.S.C. 154(b) by 25 days.

(21) Appl. No.: 13/293,560

(22) Filed: Nov. 10, 2011

(65) Prior Publication Data

US 2012/0122764 A1    May 17, 2012

Related U.S. Application Data

(60) Provisional application No. 61/414,171, filed on Nov. 16, 2010.

(51) Int. Cl.

| | | |
|---|---|---|
| A61K 31/165 | (2006.01) |
| C07D 295/185 | (2006.01) |
| C07C 237/22 | (2006.01) |
| C07D 257/04 | (2006.01) |
| C07D 307/52 | (2006.01) |
| C07C 233/63 | (2006.01) |
| C07D 213/55 | (2006.01) |
| C07C 233/52 | (2006.01) |
| C07D 471/04 | (2006.01) |
| C07D 207/16 | (2006.01) |

(52) U.S. Cl.
CPC .......... C07C 233/52 (2013.01); C07C 295/185 (2013.01); C07C 237/22 (2013.01); C07D 257/04 (2013.01); C07D 307/52 (2013.01); C07C 233/63 (2013.01); C07D 213/55 (2013.01); C07C 2101/08 (2013.01); C07D 471/04 (2013.01); C07D 207/16 (2013.01)
USPC .......... 514/579; 514/617; 514/619; 514/621; 514/646

(58) Field of Classification Search
None
See application file for complete search history.

(56) References Cited

U.S. PATENT DOCUMENTS

| | | | |
|---|---|---|---|
| 5,635,504 | A | 6/1997 | Ryono et al. |
| 6,531,494 | B1 | 3/2003 | Khanna et al. |
| 6,660,756 | B2 * | 12/2003 | Challenger et al. ........... 514/357 |
| 2002/0169101 | A1 | 11/2002 | Gonzalez et al. |
| 2009/0270338 | A1 | 10/2009 | Galemmo, Jr. et al. |
| 2009/0286758 | A1 | 11/2009 | McElroy et al. |

FOREIGN PATENT DOCUMENTS

| | | |
|---|---|---|
| EP | 0 534 396 A2 | 3/1993 |
| EP | 0 617 009 A1 | 9/1994 |
| EP | 0 747 393 A1 | 12/1996 |
| IN | 2006-DE1558 A | 1/2008 |
| JP | 5092948 | 4/1993 |
| JP | 8259532 A | 10/1996 |
| WO | 94/15908 A1 | 7/1994 |
| WO | WO9415908 * | 7/1994 |
| WO | 00/48988 A1 | 8/2000 |
| WO | 01/42215 A1 | 6/2001 |
| WO | 01/42225 A1 | 6/2001 |
| WO | 01/74784 A1 | 10/2001 |
| WO | 02/40008 A2 | 5/2002 |
| WO | 02079143 A1 | 10/2002 |
| WO | 2007/056324 A2 | 5/2007 |
| WO | 2007/100763 A2 | 9/2007 |
| WO | 2009/015485 A1 | 2/2009 |
| WO | 2010/136474 A2 | 12/2010 |
| WO | 2010/136493 A1 | 12/2010 |

OTHER PUBLICATIONS

McDowell, Garry and Nicholls, D. Paul; "The therapeutic potential candoxatril, a neutral endopeptidase inhibitor, in humans." Cardiovascular Drug Rev. (2000) 18(4) p. 259-270.*
Machine translation of WO9415908, originally published Jul. 1994.*
Pryde et al.; "Novel selective inhibitors of neutral endopeptidase for the treatment of female sexual arousal disorder"; Bioorganic & Medicinal Chemistry; 15:142-159 (2007).

* cited by examiner

*Primary Examiner* — James H Alstrum Acevedo
*Assistant Examiner* — Fred Reynolds
(74) *Attorney, Agent, or Firm* — Sophie Binet-Cross

(57) ABSTRACT

The present invention provides a compound of formula I;

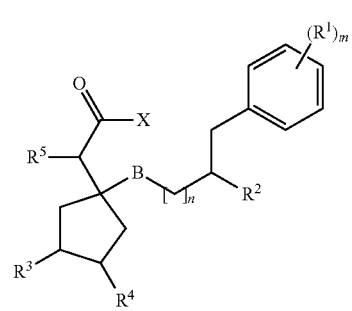

or a pharmaceutically acceptable salt thereof, wherein $R^1$, $R^2$, $R^3$, $R^4$, $R^5$, B, X, m and n are defined herein. The invention also relates to a method for manufacturing the compounds of the invention, and its therapeutic uses. The present invention further provides pharmaceutical composition of compounds of the invention, and a combination of pharmacologically active agents and a compound of the invention.

18 Claims, No Drawings

SUBSTITUTED CARBAMOYLCYCLOALKYL ACETIC ACID DERIVATIVES AS NEP

This application claims benefit under 35 U.S.C. §119(e) of U.S. Provisional Application No. 61/414,171, filed Nov. 16, 2010, the content of which are incorporated herein by reference in their entirety.

BACKGROUND OF THE INVENTION

Endogenous atrial natriuretic peptides (ANP), also called atrial natriuretic factors (ANF) have diuretic, natriuretic and vasorelaxant functions in mammals. The natural ANF peptides are metabolically inactivated, in particular by a degrading enzyme which has been recognized to correspond to the enzyme neutral endopeptidase (NEP) EC 3.4.24.11, also responsible for e.g. the metabolic inactivation of enkephalins.

Neutral endopeptidase (EC 3.4.24.11; enkephalinase; atriopeptidase; NEP) is a zinc-containing metalloprotease that cleaves a variety of peptide substrates on the amino side of hydrophobic residues [see *Pharmacol Rev*, Vol. 45, p. 87 (1993)]. Substrates for this enzyme include, but are not limited to, atrial natriuretic peptide (ANP, also known as ANF), brain natriuretic peptide (BNP), met- and leu-enkephalin, bradykinin, neurokinin A, endothelin-1 and substance P. ANP is a potent vasorelaxant and natriuretic agent [see *J Hypertens*, Vol. 19, p. 1923 (2001)]. Infusion of ANP in normal subjects resulted in a reproducible, marked enhancement of natriuresis and diuresis, including increases in fractional excretion of sodium, urinary flow rate and glomerular filtration rate [see *J Clin Pharmacol*, Vol. 27, p. 927 (1987)]. However, ANP has a short half-life in circulation, and NEP in kidney cortex membranes has been shown to be the major enzyme responsible for degrading this peptide [see *Peptides*, Vol. 9, p. 173 (1988)]. Thus, inhibitors of NEP (neutral endopeptidase inhibitors, NEPi) should increase plasma levels of ANP and, hence, are expected to induce natriuretic and diuretic effects.

This enzyme is involved in the breakdown of several bioactive oligopeptides, cleaving peptide bonds on the amino side of hydrophobic amino acid residues. The peptides metabolised include atrial natriuretic peptides (ANP), bombesin, bradykinin, calcitonin gene-related peptide, endothelins, enkephalins, neurotensin, substance P and vasoactive intestinal peptide. Some of these peptides have potent vasodilatory and neurohormone functions, diuretic and natriuretic activity or mediate behaviour effects.

SUMMARY OF THE INVENTION

The aim of the present invention is to provide novel compounds which are useful as neutral endopeptidase inhibitors, e.g. as inhibitors of the ANF-degrading enzyme in mammals, so as to prolong and potentiate the diuretic, natriuretic and vasodilator properties of ANF in mammals, by inhibiting the degradation thereof to less active metabolites. The compounds of this invention are thus particularly useful for the treatment of conditions and disorders responsive to the inhibition of neutral endopeptidase (NEP) EC 3.4.24.11.

The invention pertains to the compounds, which inhibit NEP, their pharmaceutical composition, and their methods of use, as described herein. Examples of compounds of the invention include the compounds according to anyone of Formulae I to VI, or a pharmaceutically acceptable salt thereof and the compounds of the examples.

The invention therefore provides a compound of the formula (I):

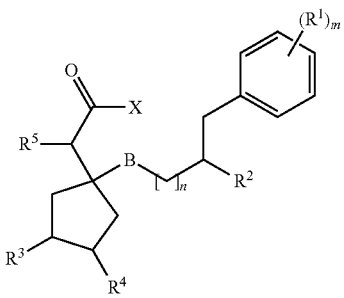

or a pharmaceutically acceptable salt thereof wherein:
$R^3$ and $R^4$ are H or $R^3$ and $R^4$ together with the carbon atoms to which they are attached form a phenyl ring;
n is 0 or 1;
$R^1$, for each occurrence, is independently halo, $C_{1-6}$alkyl, $C_{1-6}$alkoxy, hydroxy, heteroaryl or phenyl; wherein heteroaryl and phenyl can be optionally substituted with one or more substituents independently selected from halo, $C_{1-6}$alkyl, halo-$C_{1-6}$alkyl, cyano, $C_{1-6}$alkoxy, hydroxy and $NR^cR^d$; wherein $R^c$ and $R^d$ are independently H or $C_{1-6}$alkyl; or two adjacent $R^1$ groups form together with the carbon atoms to which they are attached a 5- or 6-membered heteroaryl ring optionally substituted with one or more substitutents independently selected from halo, $C_{1-6}$alkyl, cyano, hydroxy and $C_{1-6}$alkoxy;
$R^2$ is $(CH_2)_pC(O)X^1$, or $(CH_2)_s$-heteroaryl; wherein heteroaryl is a mono or bicyclic heteroaryl ring containing from 5-10 ring members selected from carbon atoms and 1 to 5 heteroatoms, and each heteroatom is independently selected from O, N or S wherein S and N may be oxidized to various oxidation states and the heteroaryl is optionally substituted with one or more substituents independently selected from halo, $C_{1-6}$alkyl, cyano, hydroxy, $C_{1-6}$alkoxy, carboxy and $C(O)O-C_{1-6}$alkyl;
$R^5$ is H, $C_{1-6}$alkyl or $C_{6-10}$aryl-$C_{1-6}$alkyl;
p is 0 or 1;
s is 0, 1, 2, 3 or 4;
m is 0, 1, 2, 3, 4 or 5;
X and $X^1$ are independently OH, O—$C_{1-6}$alkyl, O-benzyl or $NR^aR^b$ wherein $R^a$ and $R^b$ are independently H, $C_{1-6}$alkyl optionally substituted with one or more substituents independently selected from halo, hydroxy, $C_{1-6}$alkoxy and carboxy; or $R^a$ and $R^b$ together with the nitrogen atom to which they are attached form a 5- or 6-membered heterocyclyl optionally substituted with one or more substituents independently selected from $C_{1-6}$alkyl, halo, hydroxy, $C_{1-6}$alkoxy, carboxy, C(O)O—$C_{1-6}$alkyl and C(O)O-benzyl; and
B is C(O)NH or NHC(O), with the proviso that the compound is not 4-(bisphenyl-4-yl)-3-(1-carboxymethyl)cyclopentanecarboxamido)butanoic acid.

The compounds of the invention, by inhibiting the neutral endopeptidase EC.3.4.24.11, can potentiate the biological effects of bioactive peptides. Thus, in particular the compounds have utility in the treatment of a number of disorders, including hypertension, pulmonary hypertension, pulmonary arterial hypertension, isolated systolic hypertension, resistant hypertension, peripheral vascular disease, heart failure, congestive heart failure, left ventricular hypertrophy, angina, renal insufficiency (diabetic or non-diabetic), renal failure (including edema and salt retention), diabetic nephropathy, non-diabetic nephropathy, constrast induced nephropathy, nephroic syndrome, glomerulonephritis, scleroderma, glomerular sclerosis, proteinurea of primary renal disease, renal vascular hypertention, diabetic retinopathy and end-stage renal disease (ESRD), endothelial dysfunction, diastolic dysfunction, hypertrophic cardiomyopathy, diabetic cardiac myopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), renal failure (including edema and salt retension), cyclical oedema, Menières disease, hyperaldosteroneism (primary and secondary) and hypercalciuria, ascites. In addition, because of their ability to potentiate the effects of ANF the compounds have utility in the treatment of glaucoma. As a further result of their ability to inhibit the neutral endopeptidase E.C.3.4.24.11 the compounds of the invention may have activity in other therapeutic areas including for example the treatment of menstrual disorders, preterm labor, pre-eclampsia, endometriosis, and reproductive disorders (especially male and female infertility, polycystic ovarian syndrome, implantation failure). Also the compounds of the invention should treat asthma, obstructive sleep apnea, inflammation, leukemia, pain, epilepsy, affective disorders such as depression and psychotic condition such as dementia and geriatric confusion, obesity and gastrointestinal disorders (especially diarrhea and irritable bowel syndrome), wound healing (especially diabetic and venous ulcers and pressure sores), septic shock, gastric acid secretion dysfunction, hyperreninaemia, cystic fibrosis, restenosis, type-2 diabetes, metabolic syndrome, diabetic complications and athereosclerosis, male and female sexual dysfunction.

In a preferred embodiment the compounds of the invention are useful in the treatment of cardiovascular disorders.

In another embodiment, the invention pertains to a method for treating a disorders or diseases responsive to the inhibition of neutral endopeptidase EC 3.4.24.11 (NEP), in a subject in need of such treatment, comprising: administering to the subject an effective amount of a compound according to anyone of Formulae I-VI, or a pharmaceutically acceptable salt thereof, such that the disorder or disease responsive to the inhibition of neutral endopeptidase EC 3.4.24.11 (NEP) in the subject is treated.

In yet another embodiment, the invention pertains to pharmaceutical compositions, comprising a compound according to anyone of Formulae I-VI, or a pharmaceutically acceptable salt thereof, and one or more pharmaceutically acceptable carriers.

In still another embodiment, the invention pertains to combinations including, a compound according to anyone of Formulae I-VI, or a pharmaceutically acceptable salt thereof, and pharmaceutical combinations of one or more therapeutically active agents.

In another embodiment, the invention pertains to a method for inhibiting neutral endopeptidase EC 3.4.24.11 in a subject in need thereof, comprising: administering to the subject a therapeutically effective amount of a compound according to anyone of Formulae I-VI, or a pharmaceutically acceptable salt thereof, such that neutral endopeptidase EC 3.4. 24.11 is inhibited.

DETAILED DESCRIPTION OF THE INVENTION

Definition

For purposes of interpreting this specification, the following definitions will apply unless specified otherwise and whenever appropriate, terms used in the singular will also include the plural and vice versa.

As used herein, the term "alkyl" refers to a fully saturated branched or unbranched (or straight chain or linear) hydrocarbon moiety, comprising 1 to 20 carbon atoms. Preferably the alkyl comprises 1 to 6 carbon atoms, and more preferably 1 to 4 carbon atoms. Representative examples of alkyl include methyl, ethyl, n-propyl, iso-propyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl. The term "$C_{1-6}$alkyl" refers to a hydrocarbon having from one to six carbon atoms. The term "alkylene" refers to a divalent alkyl radical, wherein alkyl is as previously defined.

As used herein, the term "haloalkyl" refers to an alkyl as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Preferably, the polyhaloalkyl contains up to 12, or 10, or 8, or 6, or 4, or 3, or 2 halo groups. Representative examples of haloalkyl are fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms. The term "halo-$C_{1-6}$alkyl" refers to a hydrocarbon having one to six carbon atoms and being substituted by one or more halo groups.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tert-butoxy, pentyloxy, hexyloxy, cyclopropyloxy-, cyclohexyloxy- and the like. Preferably, alkoxy groups have about 1-6, more preferably about 1-4 carbons.

As used herein, the term "cycloalkyl" refers to saturated or partially unsaturated monocyclic, bicyclic or tricyclic hydrocarbon groups of 3-12 carbon atoms, preferably 3-8, or 3-7 carbon atoms. For bicyclic, and tricyclic cycloalkyl system, all rings are non-aromatic. Exemplary monocyclic hydrocarbon groups include cyclopropyl, cyclobutyl, cyclopentyl, cyclopentenyl, cyclohexyl and cyclohexenyl. Exemplary bicyclic hydrocarbon groups include bornyl, decahydronaphthyl, bicyclo[2.1.1]hexyl, bicyclo[2.2.1]heptyl, bicyclo[2.2.1]heptenyl, bicyclo[2.2.2]octyl. Exemplary tricyclic hydrocarbon groups include adamantyl. The term "$C_{3-7}$cycloakyl" refers to a cyclic hydrocarbon groups having 3 to 7 carbon atoms.

The term "aryl" refers to monocyclic or bicyclic aromatic hydrocarbon groups having 6-10 carbon atoms in the ring portion. The term "aryl" also refer to a group in which the aromatic ring is fused to a cycloalkyl ring, where the radical of attachment is on the aromatic ring or on the fused cycloalkyl ring. Representative examples of aryl are phenyl, naphthyl, hexahydroindyl, indanyl or tetrahydronaphthyl. The term "$C_{6-10}$aryl" refers to an aromatic hydrocarbon groups having 6 to 10 carbon atoms in the ring portion.

The term "arylalkyl" is an alkyl substituted with aryl. Representative examples of arylalkyl are benzyl or Phenyl-$CH_2CH_2$—. The term "$C_{6-10}$aryl-$C_{1-6}$alkyl" refers to a hydrocarbon having one to six carbon atoms, which hydrocarbon is substituted with an aryl having 6 to 10 carbon atoms.

The term "Heteroaryl" includes monocyclic or bicyclic heteroaryl, containing from 5-10 ring members selected from carbon atoms and 1 to 5 heteroatoms, and each heteroatoms is independently selected from O, N or S wherein S and N may be oxidized to various oxidation states. For bicyclic heteroaryl system, the system is fully aromatic (i.e. all rings are aromatic).

Typical monocyclic heteroaryl groups include thienyl, furyl, pyrrolyl, imidazolyl, pyrazolyl, thiazolyl, isothiazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, isothiazol-3-yl, isothiazol-4-yl, isothiazol-5-yl, oxazol-2-yl, oxazol-4-yl, oxazol-5-yl, isoxazol-3-yl, isoxazol-4-yl, isoxazol-5-yl, 1,2,4-triazol-3-yl, 1,2,4-triazol-5-yl, 1,2,3-triazol-4-yl, 1,2,3-triazol-5-yl, tetrazolyl, pyrid-2-yl, pyrid-3-yl, or pyridyl-4-yl, pyridazin-3-yl, pyridazin-4-yl, pyrazin-3-yl, 2-pyrazin-2-yl, pyrazin-4-yl, pyrazin-5-yl, 2-, 4-, or 5-pyrimidin-2-yl, pyrimidin-4-yl, pyrimidin-5-yl. The term "heteroaryl" also refers to a group in which a heteroaromatic ring is fused to one or more aryl rings, where the radical or point of attachment is on the heteroaromatic ring or on the fused aryl ring. Representative examples of bicyclic heteroaryl are indolyl, isoindolyl, indazolyl, indolizinyl, purinyl, quinolizinyl, quinolinyl, isoquinolinyl, cinnolinyl, phthalazinyl, naphthyridinyl, quinazolinyl, quinaxalinyl, phenanthridinyl, phenathrolinyl, phenazinyl, phenothiazinyl, phenoxazinyl, benzisoqinolinyl, thieno[2,3-b]furanyl, furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl, 7-benzo[b]thienyl, benzoxazolyl, benzimidazolyl, benzothiazolyl, benzoxapinyl, benzoxazinyl, 1H-pyrrolo[1,2-b][2]benzazapinyl, benzofuryl, benzothiophenyl, benzotriazolyl, pyrrolo[2,3-b]pyridinyl, pyrrolo[3,2-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-d]pyridinyl, pyrazolo[3,4-b]pyridinyl, imidazo[1,2-a]pyridinyl, pyrazolo[1,5-a]pyridinyl, pyrrolo[1,2-b]pyridazinyl, imidazo[1,2-c]pyrimidinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, or pyrimido[4,5-d]pyrimidinyl. When a heteroaryl moiety is substituted with hydroxy, the invention also pertains to its oxo tautomeric. For example, an oxadiazole substituted with hydroxy also includes oxo-oxadiazole also known as oxadiazolone. The tautomerisation is represented as follow:

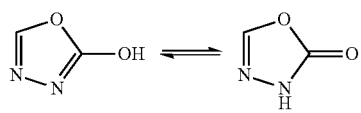

As used herein, the term "heterocyclyl" or "heterocyclo" refers to an optionally substituted, saturated or unsaturated non-aromatic (partially unsaturated) ring which is a 4-, 5-, 6-, or 7-membered monocyclic, and contains at least one heteroatom selected from O, S and N, where the N and S can also optionally be oxidized to various oxidation states. For bicyclic and tricyclic heterocyclyl ring system, a non-aromatic ring system is defined as being a non-fully or partially unsaturated ring system. Therefore bicyclic and tricyclic heterocyclyl ring systems includes heterocyclyl ring systems wherein one of the fused rings is aromatic but the other(s) is (are) non-aromatic. In one embodiment, heterocyclyl moiety represents a saturated monocyclic ring containing from 5-7 ring atoms and optionally containing a further heteroatom, selected from O, S or N. The heterocyclic group can be attached at a heteroatom or a carbon atom. The heterocyclyl can include fused or bridged rings as well as spirocyclic rings. Examples of heterocycles include dihydrofuranyl, dioxolanyl, dioxanyl, dithianyl, piperazinyl, pyrrolidine, dihydropyranyl, oxathiolanyl, dithiolane, oxathianyl, thiomorpholino, oxiranyl, aziridinyl, oxetanyl, oxepanyl, azetidinyl, tetrahydrofuranyl, tetrahydrothiophenyl, pyrrolidinyl, tetrahydropyranyl, piperidinyl, morpholine, piperazinyl, azepinyl, oxapinyl, oxaazepanyl, oxathianyl, thiepanyl, azepanyl, dioxepanyl, and diazepanyl.

The term "halogen" or "halo" includes fluoro, bromo, chloro and iodo. The term "perhalogenated" generally refers to a moiety wherein all hydrogens are replaced by halogen atoms.

The term "heteroatom" includes atoms of any element other than carbon or hydrogen. Preferred heteroatoms are nitrogen, oxygen, sulfur and phosphorus. In one embodiment the heteroatoms is selected from N, O and S.

Compound of the Invention:

Various embodiments of the invention are described herein. It will be recognized that features specified in each embodiment may be combined with other specified features to provide further embodiments.

The invention therefore provides a compound of the formula (I):

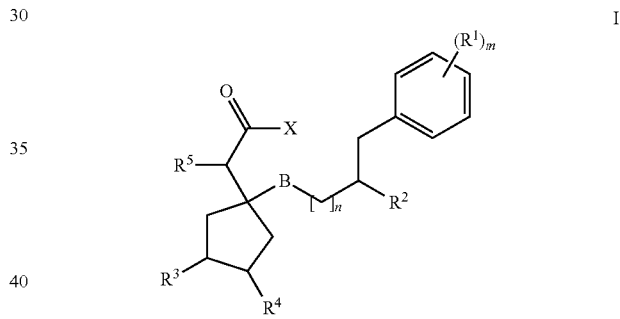

or a pharmaceutically acceptable salt thereof wherein:
$R^3$ and $R^4$ are H or $R^3$ and $R^4$ together with the carbon atoms to which they are attached form a phenyl ring;
n is 0 or 1;
$R^1$, for each occurrence, is independently halo, $C_{1-6}$alkyl, $C_{1-6}$alkoxy, hydroxy, heteroaryl or phenyl; wherein heteroaryl and phenyl can be optionally substituted with one or more substituents independently selected from halo, $C_{1-6}$alkyl, halo-$C_{1-6}$alkyl, cyano, $C_{1-6}$alkoxy, hydroxy and $NR^cR^d$; wherein $R^c$ and $R^d$ are independently H or $C_{1-6}$alkyl; or two adjacent $R^1$ groups form together with the carbon atoms to which they are attached a 5- or 6-membered heteroaryl ring optionally substituted with one or more substitutents independently selected from halo, $C_{1-6}$alkyl, cyano, hydroxy and $C_{1-6}$alkoxy;
$R^2$ is $(CH_2)_pC(O)X^1$, or $(CH_2)_s$-heteroaryl; wherein heteroaryl is a mono or bicyclic heteroaryl ring containing from 5-10 ring members selected from carbon atoms and 1 to 5 heteroatoms, and each heteroatom is independently selected from O, N or S wherein S and N may be oxidized to various oxidation states and the heteroaryl is optionally substituted with one or more substituents independently selected from halo, $C_{1-6}$alkyl, cyano, hydroxy, $C_{1-6}$alkoxy, carboxy and $C(O)O-C_{1-6}$alkyl;

$R^5$ is H, $C_{1-6}$alkyl or $C_{6-10}$aryl-$C_{1-6}$alkyl;

p is 0 or 1;

s is 0, 1, 2, 3 or 4;

m is 0, 1, 2, 3, 4 or 5;

X and $X^1$ are independently OH, O—$C_{1-6}$alkyl, O-benzyl or $NR^aR^b$ wherein $R^a$ and $R^b$ are independently H, $C_{1-6}$alkyl optionally substituted with one or more substituents independently selected from halo, hydroxy, $C_{1-6}$alkoxy and carboxy; or $R^a$ and $R^b$ together with the nitrogen atom to which they are attached form a 5- or 6-membered heterocyclyl optionally substituted with one or more substituents independently selected from $C_{1-6}$alkyl, halo, hydroxy, $C_{1-6}$alkoxy, carboxy, C(O)O—$C_{1-6}$alkyl and C(O)O-benzyl; and B is C(O)NH or NHC(O), with the proviso that the compound is not 4-(bisphenyl-4-yl)-3-(1-carboxymethyl)cyclopentanecarboxamido)butanoic acid, 4-([1,1'-biphenyl]-4-yl)-3-(1-(2-(benzyloxy)-2-oxoethyl)cyclopentanecarboxamido)butanoic acid or tert-butyl 4-([1,1'-biphenyl]-4-yl)-3-(1-(2-(benzyloxy)-2-oxoethyl)cyclopentanecarboxamido)butanoate.

Certain compounds of Formula I wherein n is 0 include compounds of Formula II:

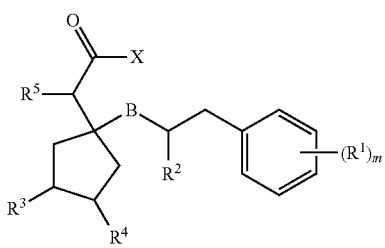

II or a pharmaceutically acceptable salt thereof, wherein $R^1$, $R^2$, $R^3$, $R^4$, $R^5$, B, X and m have the definition of Formula I, supra.

Certain compounds of Formula I wherein n is 1 include compounds of Formula III:

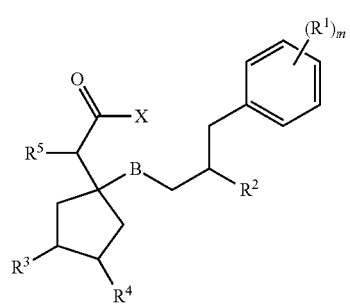

III or a pharmaceutically acceptable salt thereof, wherein $R^1$, $R^2$, $R^3$, $R^4$, $R^5$, B, X and m have the definition of Formula I, supra.

In one embodiment the invention pertains to compounds of formula I, II or III wherein B is C(O)NH. This embodiment is represented by compounds of Formula IV:

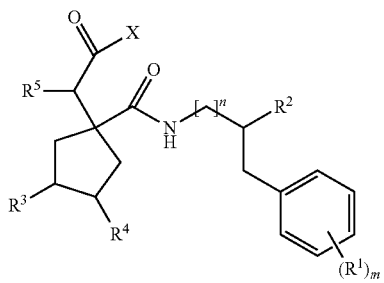

IV a pharmaceutically acceptable salt thereof, wherein $R^1$, $R^2$, $R^3$, $R^4$, $R^5$, X, n and m have the definition of Formula I, supra.

In another embodiment the invention pertains to compounds of anyone of formulae I to IV wherein $R^1$ is phenyl or pyridinyl each of which is optionally substituted by one or more substituents selected from halo, $C_{1-6}$alkyl, halo-$C_{1-6}$alkyl, cyano, $C_{1-6}$alkoxy, hydroxy and $NR^cR^d$; wherein $R^c$ and $R^d$ are independently H or $C_{1-6}$alkyl, or a pharmaceutically acceptable salt thereof. In a further aspect of this embodiment $R^1$ is phenyl optionally substituted by one or more substituents selected from halo, $C_{1-6}$alkyl, halo-$C_{1-6}$alkyl, cyano, $C_{1-6}$alkoxy, hydroxy and $NR^cR^d$; wherein $R^c$ and $R^d$ are independently H or $C_{1-6}$alkyl; or a pharmaceutically acceptable salt thereof. In yet a further aspect of this embodiment, $R^1$ is phenyl and is attached to the para position of the phenyl ring. This embodiment is illustrated by a compound of Formula V:

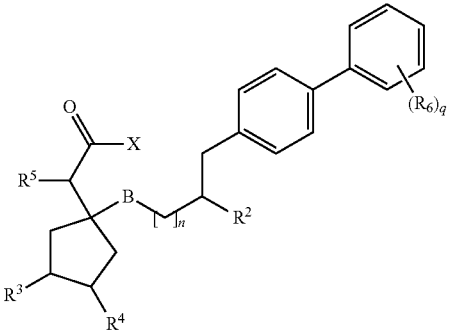

V a pharmaceutically acceptable salt thereof, wherein $R^2$, $R^3$, $R^4$, $R^5$, X, n have the definition of Formula I, supra; $R^6$ is halo, $C_{1-6}$alkyl, halo-$C_{1-6}$alkyl, cyano, $C_{1-6}$alkoxy, hydroxy or $NR^cR^d$; wherein $R^c$ and $R^d$ are independently H or $C_{1-6}$alkyl; and q is 0, 1, 2, 3, 4 or 5.

In one embodiment, the invention pertains to compound of Formula V wherein n is 0.

In another embodiment, the invention pertains to compounds of Formula V wherein n is 1.

In yet another embodiment, the invention pertains to compounds of Formula V, or classes or subclasses of compounds of Formula V as described supra, wherein B is C(O)NH.

In yet another aspect of this embodiment, the invention pertains to compounds of Formula V wherein n is 0, B is C(O)NH and the stereochemistry at the carbon bearing the $R^2$ group and the benzyl group is as depicted in Formula VI:

VI

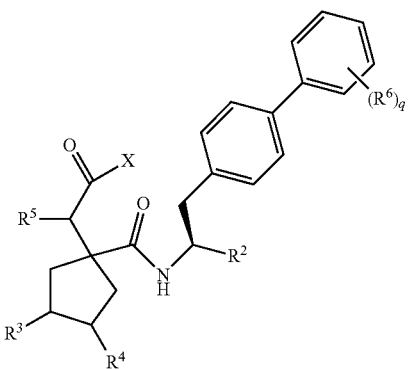

a pharmaceutically acceptable salt thereof, wherein $R^2$, $R^3$, $R^4$, $R^5$, X, n have the definition of Formula I, supra; $R^6$ is halo, $C_{1-6}$alkyl, halo-$C_{1-6}$alkyl, cyano, $C_{1-6}$alkoxy, hydroxy or $NR^cR^d$; wherein $R^c$ and $R^d$ are independently H or $C_{1-6}$alkyl; and q is 0, 1, 2, 3, 4 or 5. In one aspect of this embodiment, $R^6$ is halo and is in the meta position of the $R^1$ phenyl ring, the meta position being meta from the point of attachment of the $R^1$ group to the phenyl ring.

The following embodiments can be used independently, collectively or in any combination or sub-combination:

In one embodiment, the invention pertains to compounds according to anyone of Formulae I to VI, or any of any other classes and subclasses described supra, or a pharmaceutically acceptable salt thereof, wherein $R^5$ is H or $C_{1-6}$alkyl. In a further embodiment $R^5$ is H.

In another embodiment, the invention pertains to compounds according to anyone of Formulae I to III and V or any of any other classes and subclasses described supra, or a pharmaceutically acceptable salt thereof, wherein B is C(O)NH.

In another embodiment, the invention pertains to compounds according to anyone of Formulae I to III and V or any of any other classes and subclasses described supra, or a pharmaceutically acceptable salt thereof, wherein B is NHC(O).

In another embodiment, the invention pertains to compounds according to anyone of Formulae I to VI or any of any other classes and subclasses described supra, or a pharmaceutically acceptable salt thereof, wherein $R^3$ and $R^4$ are H.

In another embodiment, the invention pertains to compounds according to anyone of Formulae I to VI or any of any other classes and subclasses described supra, or a pharmaceutically acceptable salt thereof, wherein $R^3$ and $R^4$ together with the carbon to which they are attached form a phenyl ring.

In another embodiment, the invention pertains to compounds according to anyone of Formulae I to VI or any of any other classes and subclasses described supra, or a pharmaceutically acceptable salt thereof, wherein X is OH, O—$C_{1-6}$alkyl or O-benzyl In yet another embodiment, the invention pertains to compounds according to anyone of Formulae I to VI or any of any other classes and subclasses described supra, or a pharmaceutically acceptable salt thereof, wherein X is $NR^aR^b$, wherein $R^a$ and $R^b$ are independently H, $C_{1-6}$alkyl optionally substituted with one or more substituents independently selected from halo, hydroxy, $C_{1-6}$alkoxy and carboxy; or $R^a$ and $R^b$ together with the nitrogen atom to which they are attached form a 5- or 6-membered heterocyclyl optionally substituted with one or more substituents independently selected from $C_{1-6}$alkyl, halo, hydroxy, $C_{1-6}$alkoxy, carboxy, C(O)O—$C_{1-6}$ alkyl and C(O)O-benzyl. In a further aspect of this embodiment, $R^a$ and $R^b$ form a pyrrolidine optionally substituted with $C_{1-6}$alkyl, halo, hydroxy, $C_{1-6}$alkoxy, carboxy, C(O)O—$C_{1-6}$alkyl or C(O)O-benzyl.

In another embodiment, the invention pertains to compounds according to anyone of Formulae I to VI or any of any other classes and subclasses described supra, or a pharmaceutically acceptable salt thereof, wherein $R^2$ is $(CH_2)_pC(O)X^1$ and p and $X^1$ are as defined supra in Formula I. In one aspect of this embodiment $R^2$ is $C(O)X^1$. In another aspect of this embodiment, $R^2$ is $CH_2C(O)X^1$. In yet another aspect of this embodiment, $R^2$ is $C(O)X^1$ when n is 1. In yet another aspect of this embodiment, $R^2$ is $C(O)X^1$ when n is 0. In yet another aspect of this embodiment, $R^2$ is $CH_2C(O)X^1$ when n is 1.

In another embodiment, the invention pertains to compounds according to anyone of Formulae, I, II, IV, V and VI or of any other classes and subclasses described supra, or a pharmaceutically acceptable salt thereof, wherein $R^2$ is $CH_2C(O)X^1$, n is 0, B is NHC(O) and $X^1$ is defined supra in Formula I.

In another embodiment, the invention pertains to compounds according to anyone of Formulae, I, II, IV, V and VI or of any other classes and subclasses described supra, or a pharmaceutically acceptable salt thereof, wherein $R^2$ is $CH_2C(O)X^1$, n is 0, $X^1$ is $NR^aR^b$ wherein $R^a$ and $R^b$ are as defined above.

In another embodiment, the invention pertains to compounds according to anyone of Formulae, I, II, IV, V and VI or of any other classes and subclasses described supra, or a pharmaceutically acceptable salt thereof, wherein $R^2$ is $C(O)X^1$ or $(CH_2)_s$heteroaryl, which is optionally substituted with one or more substituents independently selected from halo, $C_{1-6}$alkyl, halo-$C_{1-6}$alkyl, cyano, hydroxy, $C_{1-6}$alkoxy, carboxy and C(O)O—$C_{1-6}$alkyl, and wherein $X^1$ is defined supra in Formula I.

In another embodiment, the invention pertains to compounds according to anyone of Formulae I to VI or any of any other classes and subclasses described supra, or a pharmaceutically acceptable salt thereof, wherein $R^2$ is $(CH_2)_s$-heteroaryl, wherein heteroaryl is mono or bicyclic heteroaryl ring containing from 5-10 ring members selected from carbon atoms and 1 to 5 heteroatoms, each heteroatom being independently selected from O, N and S, wherein S or N may be oxidized to various oxidation states and heteroaryl is optionally substituted with one or more substituents independently selected from halo, $C_{1-6}$alkyl, halo-$C_{1-6}$alkyl, cyano, hydroxy, $C_{1-6}$alkoxy, carboxy and C(O)O—$C_{1-6}$alkyl.

In one aspect of this embodiment, the invention pertains to compounds according to anyone of Formulae I to VI or any of any other classes and subclasses described supra, or a pharmaceutically acceptable salt thereof, wherein $R^2$ is $(CH_2)_s$-heteroaryl, and heteroaryl is a 5- or 6-membered heteroaryl, optionally substituted with halo, $C_{1-6}$alkyl, halo-$C_{1-6}$alkyl, cyano, hydroxy, $C_{1-6}$alkoxy, carboxy or C(O)O—$C_{1-6}$alkyl. In a further aspect of this embodiment, the heteroaryl is a 5-membered heteroaryl selected from the group consisting of oxazole, pyrrole, pyrazole, isooxazole, triazole, tetrazole, oxadiazole (e.g. 1-oxa-3,4-diazole, 1-oxa-2,4-diazole), oxadiazolone (e.g. oxadiazol-2-one), thiazole, isothiazole, thiophene, imidazole and thiadiazole, each of which is optionally substituted with one or more substitutents independently selected from halo, $C_{1-6}$alkyl, halo-$C_{1-6}$alkyl, cyano, hydroxy, $C_{1-6}$alkoxy, carboxy and C(O)O—$C_{1-6}$alkyl. In yet a further aspect of this embodiment, the heteroaryl is tetrazole or imidazole optionally substituted with one or more substituents independently selected from halo, $C_{1-6}$alkyl, halo-$C_{1-6}$alkyl, cyano, hydroxy, $C_{1-6}$alkoxy, carboxy and C(O)O—$C_{1-6}$alkyl. In yet another aspect of this embodiment, the heteroaryl is a 6-membered heteroaryl selected from the group consisting of pyrazine, pyridine, pyrimidine, pyranone (e.g. optionally substituted pyran-4-one, pyran-2-one such as 3-hydroxy-pyran-4-one, 3-hydroxy-pyran-2-one), pyrimidinone and pyridinone (e.g. optionally substituted pyridin-4-one or pyridin-2-one such as for example 3-hydroxy-1-methyl-pyridin-4-one or 1-benzyl-pyridin-2-one).

In another embodiment $R^1$, $R^2$, $R^3$, $R^4$, $R^5$, B, X, m and n groups are those defined by the $R^1$, $R^2$, $R^3$, $R^4$, $R^5$, B, X, m and n groups in the Examples section below.

In another embodiment individual compounds according to the invention are those listed in the Examples section below or a pharmaceutically acceptable salt thereof.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)— or (S)—. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95 enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O' p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

As used herein, the term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids, e.g., acetate, aspartate, benzoate, besylate, bromide/hydrobromide, bicarbonate/carbonate, bisulfate/sulfate, camphorsulformate, chloride/hydrochloride, chlortheophyllonate, citrate, ethandisulfonate, fumarate, gluceptate, gluconate, glucuronate, hippurate, hydroiodide/iodide, isethionate, lactate, lactobionate, laurylsulfate, malate, maleate, malonate, mandelate, mesylate, methylsulphate, naphthoate, napsylate, nicotinate, nitrate, octadecanoate, oleate, oxalate, palmitate, pamoate, phosphate/hydrogen phosphate/dihydrogen phosphate, polygalacturonate, propionate, stearate, succinate, sulfosalicylate, tartrate, tosylate and trifluoroacetate salts.

Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like. Pharmaceutically acceptable base addition salts can be formed with inorganic and organic bases. Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate or the like), or by reacting free base forms of these compounds with a stoichiometric amount of the appropriate acid. Such reactions are typically carried out in water or in an organic solvent, or in a mixture of the two. Generally, use of non-aqueous media like ether, ethyl acetate, ethanol, isopropanol, or acetonitrile is desirable, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. For example, any hydrogen represented by "H" in any of the formulae herein is intended to represent all isotopic forms of hydrogen (e.g. $^1$H, $^2$H or D, $^3$H); any carbon represented by "C" in any of the formulae herein is intended to represent all isotopic forms of carbon (e.g. $^{11}$C, $^{13}$C, $^{14}$C); any nitrogen represented by "N" is intended to represent all isotopic forms of nitrogen (e.g. $^{14}$N, $^{15}$N). Other examples of isotopes that are included in the invention include isotopes of oxygen, sulfur, phosphorous, fluorine, iodine and chlorine, such as $^{18}$F $^{31}$P, $^{32}$P, $^{35}$S, $^{36}$Cl, $^{125}$I. The invention includes various isotopically labeled compounds as defined herein, for example those into which radioactive isotopes, such as $^3$H, $^{13}$C, and $^{14}$C are present. In one embodiment, the atoms in the formulae herein occur in their natural abundance. In another embodiment, one or more hydrogen atom may be enriched in $^2$H; or/and one or more carbon atom may be enriched in $^{11}$C, $^{13}$C or $^{14}$C; or/and one or more nitrogen may be enriched in $^{14}$N. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, enrichment with heavier isotopes, particularly deuterium (i.e., $^2$H or D) may afford certain therapeutic advantages resulting from greater metabolic stability, for example increased in vivo half-life or reduced dosage requirements or an improvement in therapeutic index. It is understood that deuterium in this context is regarded as a substituent of a compound of the formulae I to VI. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). Isotopically-enriched compounds of formulae I to VI can generally be prepared by conventional techniques known to those skilled in the art or by processes analogous to those described in the accompanying Examples and Preparations using an appropriate isotopically-enriched reagent in place of the non-enriched reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds according to anyone of formulae I to VI that contain groups capable of acting as donors and/or acceptors for hydrogen bonds may be capable of forming co-crystals with suitable co-crystal formers. These co-crystals may be prepared from compounds according to anyone of formulae I to VI by known co-crystal forming procedures. Such procedures include grinding, heating, co-subliming, co-melting, or contacting in solution compounds according to anyone of formulae I to VI with the co-crystal former under crystallization conditions and isolating co-crystals thereby formed. Suitable co-crystal formers include those described in WO 2004/078163. Hence the invention further provides co-crystals comprising a compound according to anyone of formulae I to VI or a pharmaceutically acceptable salt thereof.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, and the like and combinations thereof, as would be known to those skilled in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or amelioration of a symptom, alleviation of a condition, slow or delay disease progression, or prevention of a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, a disorder or a disease or a symptom thereof (i)ameliorated by the inhibition of neutral endopeptidase EC 3.4.24.11 or (ii) associated with neutral endopeptidase EC 3.4.24.11 activity, or (iii) characterized by abnormal activity of neutral endopeptidase EC 3.4.24.11; or (2) reduce or inhibit the activity of neutral endopeptidase EC 3.4.24.11; or (3) reduce or inhibit the expression of neutral endopeptidase EC 3.4.24.11. In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of neutral endopeptidase EC 3.4.24.11; or at least partially reduce or inhibit the expression of neutral endopeptidase EC 3.4.24.11

As used herein, the term "subject" refers to an animal. Typically the animal is a mammal. A subject also refers to for example, primates (e.g., humans), cows, sheep, goats, horses, dogs, cats, rabbits, rats, mice, fish, birds and the like. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers in one embodiment, to ameliorating the disease or disorder (i.e., slowing or arresting or reducing the development of the disease or at least one of the clinical symptoms thereof). In another embodiment "treat", "treating" or "treatment" refers to alleviating or ameliorating at least one physical parameter including those which may not be discernible by the patient. In yet another embodiment, "treat", "treating" or "treatment" refers to modulating the disease or disorder, either physically, (e.g., stabilization of a discernible symptom), physiologically, (e.g., stabilization of a physical parameter), or both. In yet another embodiment, "treat", "treating" or "treatment" refers to preventing or delaying the onset or development or progression of the disease or disorder.

As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound, that contain one or more protective groups and are converted to an active form by metabolism or solvolysis. Both the active drug form and any released metabolic products should have acceptably low toxicity. Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Suitable prodrugs are often pharmaceutically acceptable ester derivatives convertible by solvolysis under physiological conditions to the parent carboxylic acid, e.g., lower alkyl esters, cycloalkyl esters, lower alkenyl esters, benzyl esters, mono- or disubstituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization.

General Synthetic Scheme:

The compounds of the invention can be synthesized using the methods described in the following schemes, examples, and by using art recognized techniques. All compounds described herein are included in the invention as compounds.

Compounds of the invention may be synthesized according to at least one of the methods described in schemes 1-3.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999.

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

Typically, the compounds according to of formulae I to VI can be prepared according to the Schemes 1 to 8 provided infra.

The compounds of the invention of Formula I can be prepared wherein X is hydroxy by hydrolysis of intermediate A wherein $R^1$, $R^2$, $R^3$, $R^4$, $R^5$, B, n and m have the definition of Formula I, supra; $P^1$ is an appropriate protecting group selected from, but not limited to, methyl, ethyl, isopropyl, tert-butyl, methoxybenzyl or benzyl.

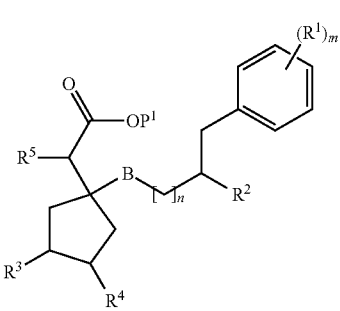

Intermediate A

Standard methods can be applied for the hydrolysis of Intermediate A using a base selected from, but not limited to, NaOH, KOH or LiOH, or an acid selected from, but not limited to, TFA, HCl or $BCl_3$. When $P_1$ is benzyl or methoxybenzyl, preferable method of deprotection is hydrogenation in the presence of a catalyst such as, but not limited to, palladium-on-carbon under hydrogen.

The intermediate A, wherein B is C(O)NH, can be prepared using the following process comprising: condensing an intermediate B wherein $P^1$, $R^3$, $R^4$ and $R^5$ areas previously described:

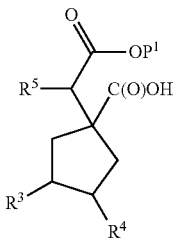

Intermediate B with an intermediate C wherein $R^1$, $R^2$, m and n are previously described.

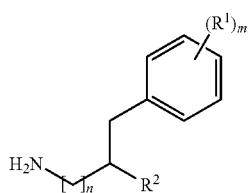

Intermediate C

Known condensation methods may be applied including, but not limited to, conversion of the intermediate B to their corresponding acid halide, using reagents such as thionyl chloride or oxalyl chloride, or conversion of intermediate B to mixed anhydride using reagents such as ClC(O)O-isobutyl or 2,4,6-trichlorobenzoyl chloride followed by reaction of the acid halide or mixed anhydride with the intermediate C in presence or absence of a base such as tertiary amine (e.g. triethylamine, DIPEA, or N-methylmorpholine) or pyridine derivative (e.g. pyridine, 4-(dimethylamino)pyridine, or 4-pyrrolidinopyridine). Alternatively, the intermediate B can be coupled with C using coupling reagents such as DCC, EDCI, PyBOP or BOP in presence or absence of a reagent such as 1-hydroxybenazotriazole, 1-hydroxy-7-azabenzotriazole or pentafluorophenol.

The intermediate A, wherein B is NHC(O), can be prepared using the following process comprising: condensing an intermediate D wherein $P^1$, $R^3$, $R^4$ and $R^5$ are as previously described:

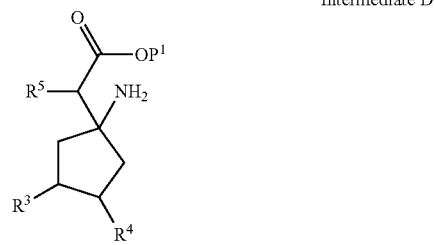

Intermediate D with an intermediate E wherein $R^1$, $R^2$, m and n are previously described.

Intermediate E

Known condensation methods may be applied including, but not limited to, conversion of the intermediate E to their corresponding acid halide, using reagents such as thionyl chloride or oxalyl chloride, or conversion of intermediate E to mixed anhydride using reagents such as ClC(O)O-isobutyl or 2,4,6-trichlorobenzoyl chloride followed by reaction of the acid halide or mixed anhydride with the intermediate D in a presence or absence of a base such as tertiary amine (e.g. triethylamine, DIPEA, or N-methylmorpholine) or pyridine derivative (e.g. pyridine, 4-(dimethylamino)pyridine, or 4-pyrrolidinopyridine). Alternatively, the intermediate D can be coupled with E using coupling reagents such as DCC, EDCI, PyBOP or BOP in presence or absence of a reagent such as 1-hydroxybenazotriazole, 1-hydroxy-7-azabenzotriazole or pentafluorophenol.

The intermediates B and D can be prepared according to the following general procedures described in Scheme 1:

Scheme 1

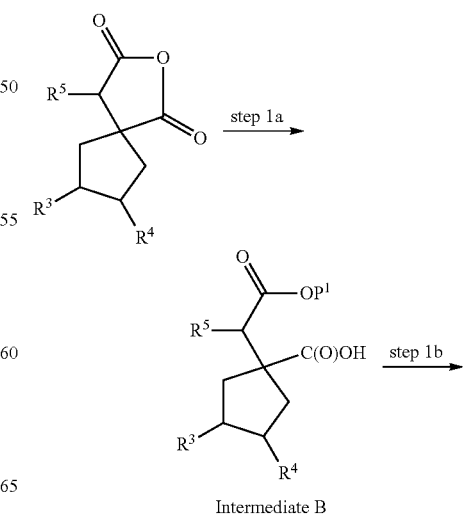

Intermediate B

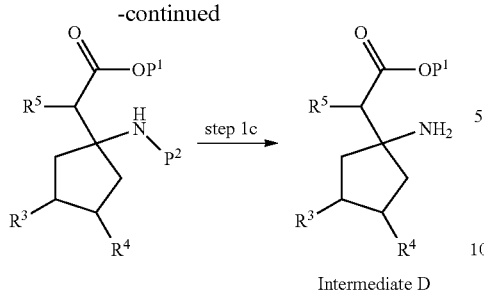

Intermediate D wherein P² is an appropriate protecting group selected from, but not limited to, hydrogen, methyl, ethyl, Bn, t-Bu, allyl, acetyl, formyl, ethoxycarbonyl, Boc, Cbz or Troc.

In step 1a, standard methods for mono-esterification of succinic anhydride analogues can be applied, such as the mix with the corresponding alcohol.

In step 1b, standard methods for introduction of the amine part can be employed, such as using: either simultaneous treatment with or stepwise treatment via the corresponding acyl azide formation by using thionyl chloride (or $ClCO_2R^7$; wherein $R^7$ are defined herein as methyl, ethyl, tert-butyl, allyl, benzyl or 4-methoxybenzyl), $NaN_3$ (or $TMSN_3$) and $R^7OH$ (or water) (wherein $R^7$ is previously described); or either simultaneous treatment with or stepwise treatment via the corresponding acyl azide formation with DPPA and $R^7OH$ (wherein $R^7$ is previously described); or standard methods for conversion to the corresponding carboxamide followed by treatment with $NH_3$ equivalent and either simultaneous treatment with or stepwise treatment with LTA or hypervalent iodine reagents (e.g. PIDA, PIFA, PhI(OH)OTs, PhIO) and $R^7OH$ (or water) (wherein $R^7$ is previously described); or standard methods for conversion to the corresponding carboxamide and either simultaneous treatment with or stepwise treatment with $Br_2$ and MOH (wherein M is defined herein as metal ion: e.g. Na, K, Ba or Ca); or standard methods for conversion to the corresponding carboxamide and treatment with MOZ or $NaBrO_2$ (wherein Z is defined herein e.g. Cl or Br); or standard methods for conversion to the corresponding carboxamide and treatment with $Pb(OAc)_4$ and $R^7OH$ (or water) (wherein $R^7$ is defined as above); or standard methods for conversion to the corresponding hydroxamic acid followed by treatment with $H_2NOH$ or $H_2NOTMS$ and treatment with $Ac_2O$, $Boc_2O$, $R^8COCl$, $R^8SO_2Cl$, $R^8PO_2Cl$ (wherein $R^8$ is defined herein as alkyl group: e.g. Me, Et, tBu or phenyl), thionyl chloride, EDCI, DCC, or 1-chloro-2,4-dinitrobenzene in the presence or absence of a base (e.g. pyridine, $Na_2CO_3$aq, triethylamine, DIPEA) and treatment with $R^7OH$ (or water) in the presence of a base (e.g. DBU, ZOH, DIPEA) (wherein $R^7$ and Z are defined as above).

In step (1c), standard methods for removing $P_2$ protecting groups can be applied, such as base hydrolysis using NaOH, KOH, or LiOH, acid hydrolysis using TFA or HCl, or hydrogenation using palladium-on-carbon under hydrogen.

Alternatively, the intermediate B can be prepared following the synthetic route outlined in WO 2006029153 A2 directly or analogously.

The intermediate C can be prepared using the method in step 1b and step 1c (Scheme 1, vide supra) from intermediate E.

Alternatively, the intermediate C (wherein n is 0 and R2 is $(CH2)_pCOX^1$ [n, p and X1 are defined as above)] can be prepared as intermediate C-1 and intermediate C-2, according to the general procedure described in Scheme 2:

Scheme 2

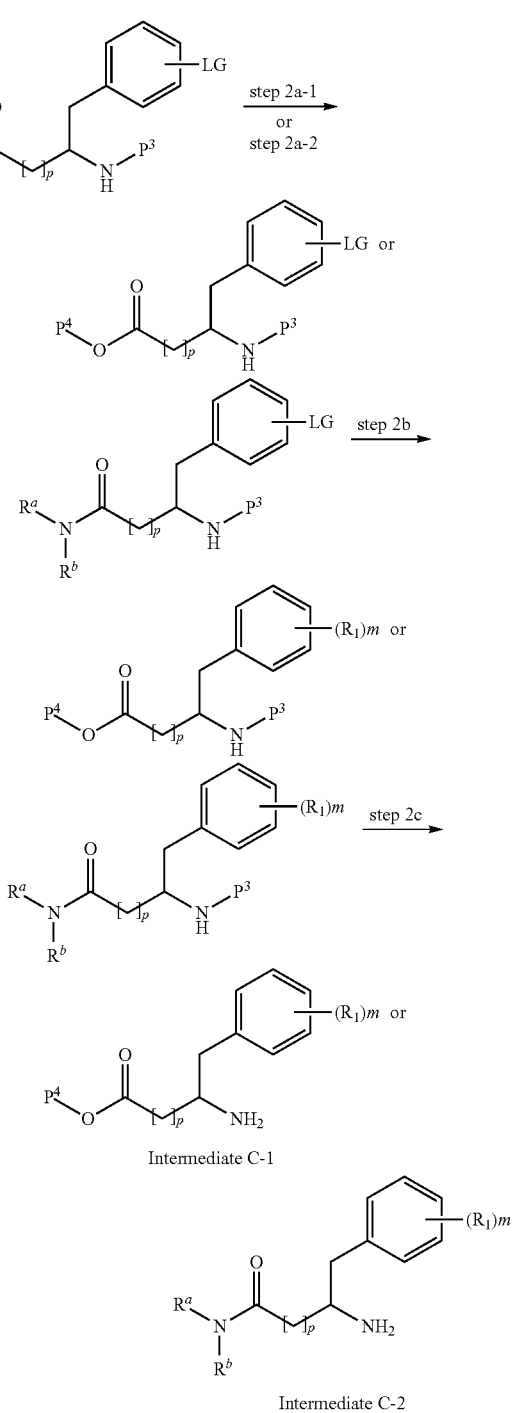

Intermediate C-1

Intermediate C-2 wherein LG is a leaving group selected from, but not limited to, Cl, Br, I, OMs, OTs or OTf; $P_3$ is an appropriate protecting group selected from, but not limited to, Bn, t-Bu, allyl, acetyl, formyl, ethoxycarbonyl, Boc, Cbz or Troc; $P_4$ is an appropriate protecting group selected from, but not limited to, methyl, ethyl, isopropyl, tert-butyl, methoxybenzyl or benzyl.

In step 2a-1, standard methods for esterification of the carboxylic acid can be employed, such as using $TMSCHN_2$ (for methyl ester), $P^4LG$/base (e.g. $K_2CO_3$, $NaHCO_3$, $Cs_2CO_3$ or $K_3PO_4$), thionyl chloride (or oxalyl chloride)/

P⁴OH, DCC (or EDCI)/DMAP/P⁴OH, BOP/P⁴OK (or P⁴ONa), (P⁴O)₂CHNMe₂, CDI/DBU/P⁴OH or isobutylene/ H₂SO₄ (for tert-butyl ester).

In step 2a-2, standard methods for amidation of the carboxylic acid can be employed, using coupling reagents such as DCC, EDCI, PyBOP or BOP in presence or absence of a reagent such as 1-hydroxybenazotriazole, 1-hydroxy-7-azabenzotriazole or pentafluorophenol.

In step 2b, standard methods for transition-metal-mediated coupling reaction can be applied, such as using a palladium (or nickel) species [e.g. Pd(PPh₃)₄, Pd(PPh₃)₂Cl₂, PdCl₂(dppf), Pd(OAc)₂/a phosphine (e.g. PPh₃, dppf, PCy₃, P(tBu)₃, XPhos), Pd/C, Pd₂(dba)₃/a phosphine (e.g. PPh₃, dppf, PCy₃, P(tBu)₃, XPhos), Ni(COD)₂/a phosphine (or dppe, dppb, dppf, PCy₃), Ni(dppf)Cl₂], and a coupling partner [e.g. (R¹)ₘ—B(OH)₂, or (R¹)ₘ—BF₃K, (R¹)ₘ—SnBu₃, (R¹)ₘ—ZnY (whereinY is F, Cl, Br or I), or (R¹)ₘ—MgY (Y is defined above)], in presence or absence of a base (e.g. KF, CsF, K₃PO₄, Na₂CO₃, K₂CO₃, Cs₂CO₃, NaOH, KOH, NaO-t-Bu, KO-t-Bu).

In step 2c, standard methods for removing P³ protecting groups can be applied, such as base hydrolysis using NaOH, KOH, or LiOH, acid hydrolysis using TFA or HCl, or hydrogenation using palladium-on-carbon under hydrogen.

Alternatively, the intermediate C may be prepared be following the synthetic routes outlined in *Tetrahedron Letters*, 2008, Vol. 49, No. 33, pp. 4977-4980 either directly or analogously and converting the obtained boronic acid into a substituted biphenyl by methods outlined in *Organic Letters*, 2002, Vol. 4, No. 22, pp. 3803-3805.

Alternatively, the intermediate C (wherein n is 1) can be prepared as intermediate C-3, according to the general procedure described in Scheme 3:

Scheme 3

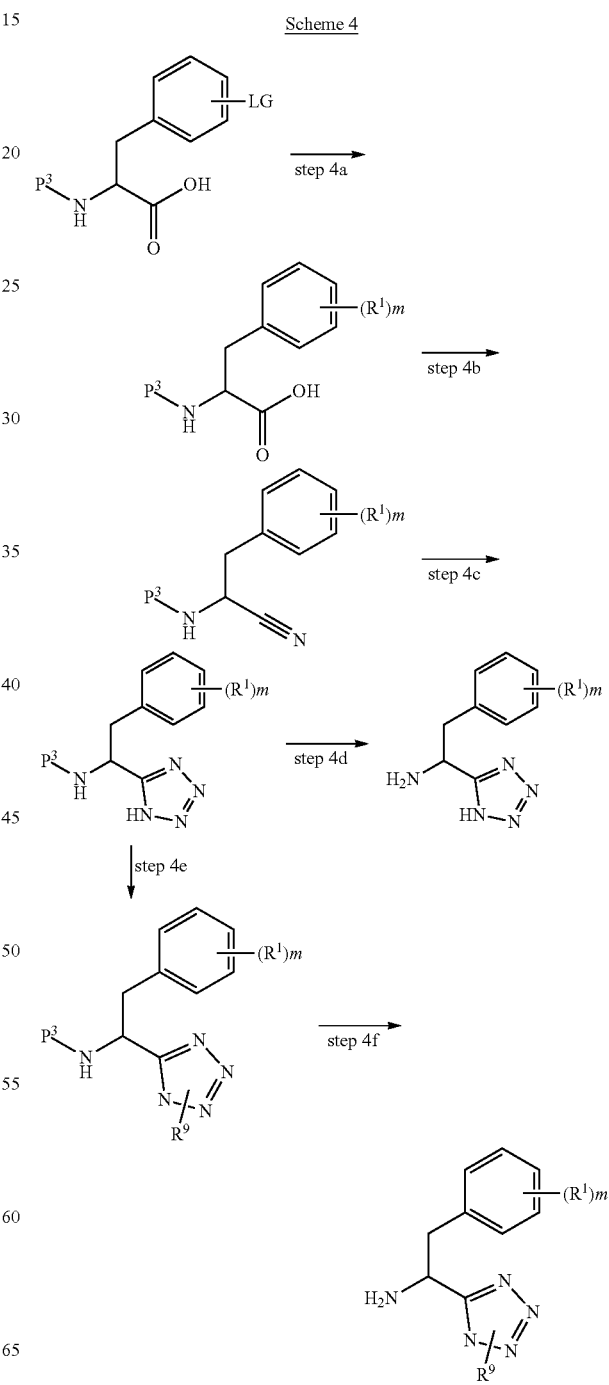

Intermediate C-3 wherein R¹, R² and m are previously described

In step 3a, the standard method of condensation of nitrile and aldehyde can be applied, such as using piperidine, Et₃N, ammonium acetate, KF, TiCl₄/amine, dry alumina (spelling), Zn(OAc)₂, BuLi, NaH or NaOMe.

In step 3b, the standard method of reduction of carbon-carbon double bond can be employed, such as using Pd-on-carbon/H₂, Zn, SmI₂, NiI₂/Li/PPh₃/PhSiH₃, CuCl/PhSiH₃, BiCl₃/NaBH₄, or RhCl₃/AlPO₄/H₂.

In step 3c, the standard method of reduction of nitrile can be employed, such as using Raney-Co/H₂, Raney-Ni/H₂ in presence or absence of Pd/C, CoCl₂/NaBH₄ or BH₃, or i-Pr₂NBH₂/LiBH4.

Alternatively, intermediate C [wherein n is 0 and R² is (CH₂)ₛ-heteroaryl: wherein s is 0 and heteroaryl is 1H-tetrazol-5-yl] can be prepared according to the general procedure described in Scheme 4:

Scheme 4

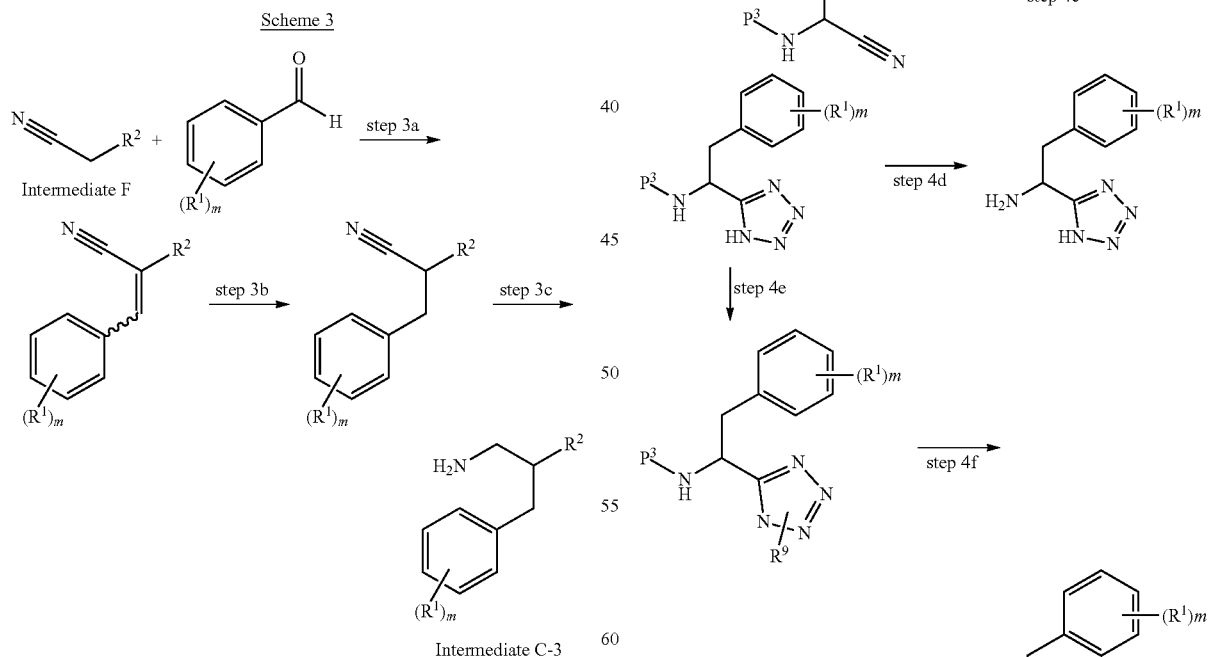

wherein $R^1$, m, $P^3$ and LG are previously described; $R^9$ is $C_1$-$C_6$alkyl group selected from, but not limited to, methyl or ethyl.

In step 4a, standard methods for transition-metal-mediated coupling reaction can be applied, such as using a palladium (or nickel) species [e.g. Pd(PPh$_3$)$_4$, Pd(PPh$_3$)$_2$Cl$_2$, PdCl$_2$ (dppf), Pd(OAc)$_2$/a phosphine (e.g. PPh$_3$, dppf, PCy$_3$, P(tBu)$_3$, XPhos), Pd/C, Pd$_2$(dba)$_3$/a phosphine (e.g. PPh$_3$, dppf, PCy$_3$, P(tBu)$_3$, XPhos), Ni(COD)$_2$/a phosphine (or dppe, dppb, dppf, PCy$_3$), Ni(dppf)Cl$_2$], and a coupling partner [e.g. $(R^1)_m$—B(OH)$_2$, or $(R^1)_m$—BF$_3$K, $(R^1)_m$—SnBu$_3$, $(R^1)_m$—ZnY (wherein Y is F, Cl, Br or I), or $(R^1)_m$—MgY (Y is defined above)], in presence or absence of a base (e.g. KF, CsF, K$_3$PO$_4$, Na$_2$CO$_3$, K$_2$CO$_3$, Cs$_2$CO$_3$, NaOH, KOH, NaO-t-Bu, KO-t-Bu).

In step 4b, standards methods for primary amide formation followed by dehydration can be applied. For the amide formation, a coupling reagent such as DCC, EDCI, PyBOP or BOP in presence or absence of a reagent such as 1-hydroxybenazotriazole, 1-hydroxy-7-azabenzotriazole or pentafluorophenol can be used in combination with ammonium hydroxide or ammonium chloride. Acid chloride formation with a reagent such as thionyl chloride or oxalyl chloride followed by treatment with ammonium hydroxide or ammonium chloride can be also used. For the dehydration, a reagent such as trifluoroacetic anhydride, POCl$_3$ or Burgess reagent can be used.

In step 4c, tetrazole ring formation can be performed with a reagent such as NaN$_3$, TMSN$_3$ or Bu$_3$SnN$_3$ in the presence of or absence of a reagent such as ZnBr$_2$, NH$_4$Cl or Et$_3$N—HCl.

In step 4d, standard methods for removing $P^3$ protecting groups can be applied, such as base hydrolysis using NaOH, KOH, or LiOH, acid hydrolysis using TFA or HCl, or hydrogenation using palladium-on-carbon under hydrogen.

In step 4e, standard alkylation methods can be applied using a reagent such as alkyl halide [e.g. iodomethane, iodoethane] in combination with base [e.g. K$_2$CO$_3$, Na$_2$CO$_3$, Cs$_2$CO$_3$, NaH, Et$_3$N].

In step 4f, standard methods for removing $P^3$ protecting groups can be applied, such as base hydrolysis using NaOH, KOH, or LiOH, acid hydrolysis using TFA or HCl, or hydrogenation using palladium-on-carbon under hydrogen.

Alternatively, intermediate C (wherein n is 0 and $R^2$ is $(CH_2)_s$-heteroaryl; wherein s is 0 and heteroaryl is 1H-tetrazol-5-yl) can be prepared following the synthetic route outlined in *Journal of Medicinal Chemistry*, 1998, pp. 1513-1523, either directly or analogously.

Alternatively, intermediate C (wherein n is 0 and $R^2$ is $(CH_2)$s-heteroaryl; wherein s is 0 and heteroaryl is 3H-imidazo[4,5-c]pyridin-2-yl [$R^1$ and m are defined as above]) can be prepared following the synthetic route outlined in *Bioorganic Medicinal Chemistry*, 2007, pp. 736-740, either directly or analogously.

Alternatively, the intermediate C may be prepared be following the synthetic routes outlined in *Tetrahedron: Asymmetry*, 2006, Vol. 17, No. 2, pp. 205-209, either directly or analogously.

Alternatively, the intermediate C may be prepared by methods of Mannich reaction. Illustrative examples of this chemistry are outlined in "Enantioselective synthesis of β-amino acids, 2$^{nd}$ Edition", John Wiley and Sons, Inc., NJ (2005), either directly or analogously.

Alternatively, the intermediate C may be prepared by methods of aza-Michael reaction. Illustrative examples of this chemistry are outlined in "Enantioselective synthesis of β-amino acids, 2$^{nd}$ Edition", John Wiley and Sons, Inc., NJ (2005), either directly or analogously.

Alternatively, the intermediate C may be prepared following the synthetic route outlined in *Synlett*, 2006, No. 4, pp. 539-542, either directly or analogously.

Alternatively, the intermediate C may be prepared following the synthetic route outlined in *Tetrahedron Letters*, 1993, Vol. 34, No. 12, pp. 1901-1904, either directly or analogously.

Alternatively, the intermediate C may be prepared following the synthetic route outlined in *The Journal of Organic Chemistry*, 1995, Vol. 60, No. 10, pp. 3112-3120, either directly or analogously.

The intermediate E (wherein n is 0 and $R^2$ is $CH_2C(O)X^1$) can be prepared according to the general procedure described in Scheme 5:

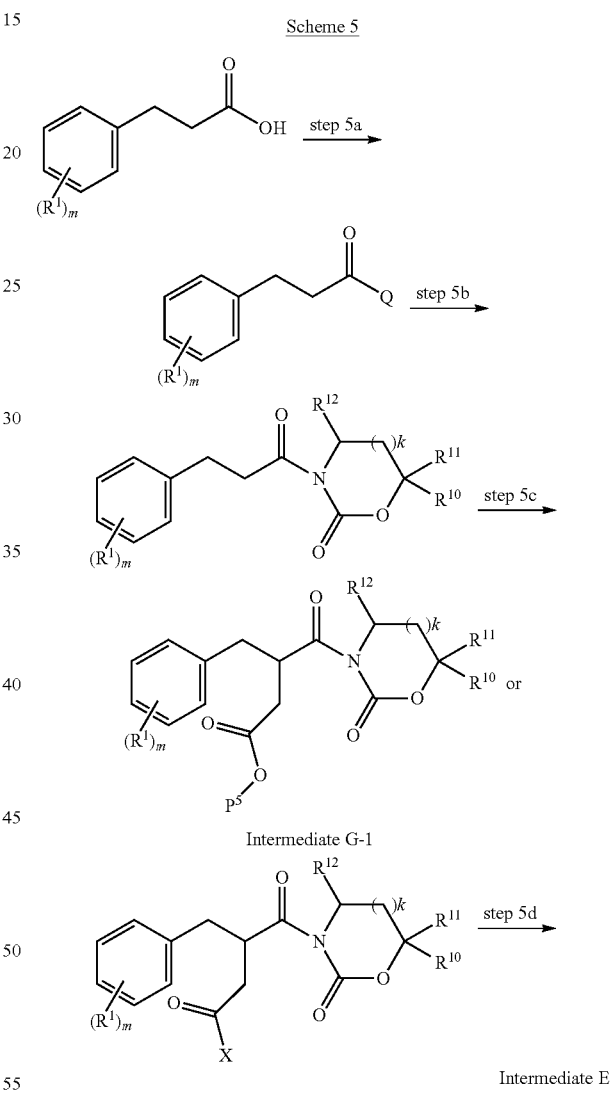

wherein $R^1$ and m are as defined above, and wherein k=0 or 1; $P^5$ is a protecting group selected from, but not limited to, hydrogen, methyl, ethyl, propyl, tert-butyl, methoxymethyl, tert-butyldimethylsilyl, tetrahydrofuranyl, benzyl, allyl or phenyl; $R^{10}$ and $R^{11}$ are independently hydrogen, methyl, ethyl, isopropyl, benzyl or phenyl; $R^{12}$ is for example hydrogen, methyl, ethyl, isopropyl, benzyl or phenyl. Q is selected from, but not limited to, chloro, bromo, iodo, benzotriazoloxy, pyridinium, N,N-dimethylaminopyridinium, pentafluorophenoxy, phenoxy, 4-chlorophenoxy, —OCO$_2$Me, —OCO$_2$Et, tert-butoxycarbonyl or —OCC(O)O-isobutyl.

In step 5a, standard methods can be applied to prepare the corresponding acid halide, such as the use of thionyl chloride, oxalyl chloride; or standard methods to prepare the mixed anhydride or the acyl pyridinium cation can be applied, such as the use of pivaloyl chloride with a tertiary amine (e.g. triethylamine, DIPEA, N-methylmorpholine) in the presence or absence of a pyridine derivative (e.g. pyridine, 4-(dimethylamino)pyridine, 4-pyrrolidinopyridine), 2,4,6-trichlorobenzoyl chloride with a tertiary amine (e.g. triethylamine, DIPEA, N-methylmorpholine) in the presence or absence of a pyridine derivative (e.g. pyridine, 4-(dimethylamino)pyridine, 4-pyrrolidinopyridine), or ClC(O)O-1-Bu with a tertiary amine (e.g. triethylamine, DIPEA, N-methylmorpholine) in the presence or absence of a pyridine derivative (e.g. pyridine, 4-(dimethylamino)pyridine, 4-pyrrolidinopyridine); or standard methods to prepare the activated ester can be applied, such as the use of 1-hydroxybenazotriazole, 1-hydroxy-7-azabenzotriazole or pentafluorophenol in the presence of a coupling reagent (e.g. DCC, EDCI) or BOP.

In step 5b, standard methods to prepare the N-acyloxazolidinones (k=0) can be employed. Illustrative examples of this chemistry are outlined in *Aldrichchimica Acta* 1997, Vol. 30, pp. 3-12 and the references therein; or standard methods to prepare the N-acyloxazinanone (k=1) can be employed. An illustrative example of this chemistry is outlined in *Organic and Biomolecular Chemistry* 2006, Vol. 4, No. 14, pp. 2753-2768.

In step 5c, standard methods for alkylation can be employed. An illustrative example is outlined in *Chemical Reviews* 1996, 96(2), 835-876 and the references therein.

In step 5d, standard methods for cleavage of N-acyloxazolidinone or N-acyloxazinanone can be employed. Illustrative examples of this chemistry are outlined in *Aldrichchimica Acta* 1997, Vo. 30, pp. 3-12 and the references therein.

The intermediate E (wherein n is 0 and $R^2$ is $CH_2C(O)X^1$) can be prepared according to the general procedure described in Scheme 6:

Scheme 6

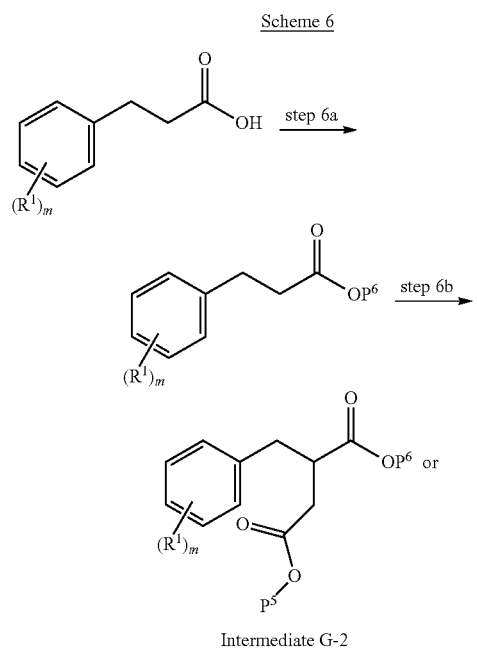

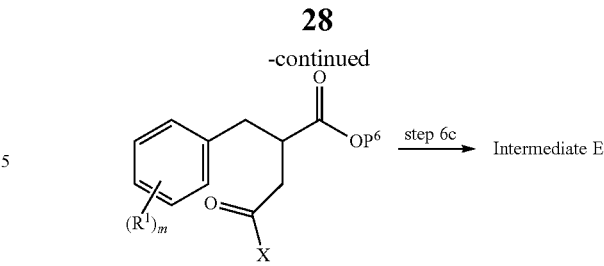

wherein $R^1$, X, $P^4$, $P^5$ and m are defined above; $P^6$ is a protecting group selected from, but not limited to, methyl, ethyl, propyl, Cert-butyl, methoxymethyl, tert-butyldimethylsilyl, tetrahydrofuranyl, benzyl, allyl or phenyl In step 6a, standard methods for esterification of the carboxylic acid can be employed, such as using $TMSCHN_2$ (for methyl ester), $P^6LG$/base (e.g. $K_2CO_3$, $NaHCO_3$, $Cs_2CO_3$ or $K_3PO_4$), thionyl chloride (or oxalyl chloride)/$P^6OH$, DCC (or EDCI)/DMAP/$P^6OH$, BOP/$P^6OK$ (or $P^6ONa$), $(P^6O)_2CHNMe_2$, CDI/DBU/$P^6OH$, or isobutylene/$H_2SO_4$ (for tert-butyl ester).

In step 6b, standard methods for alpha-alkylation of carbonyl group can be applied, using the corresponding $P^5OC(O)CH_2Y$ or $XC(O)CH_2Y$ (Y is defined above) and a base such as NHMDS, LHMDS, KHMDS, tert-BuOK, tert-BuONa, NaH, LDA, n-BuLi, sec-BuLi or tert-BuLi.

In step 6c, standard methods for removing $P^6$ protecting groups can be applied, such as base hydrolysis such as using NaOH, KOH, or LiOH, acid hydrolysis such as using TFA or HCl, or hydrogenation using palladium-on-carbon under hydrogen.

The intermediate E (wherein n is 1 and $C(O)X^1$) can be prepared from intermediate G-1 or intermediate G-2 according to the general procedure described in Scheme 7.

Scheme 7

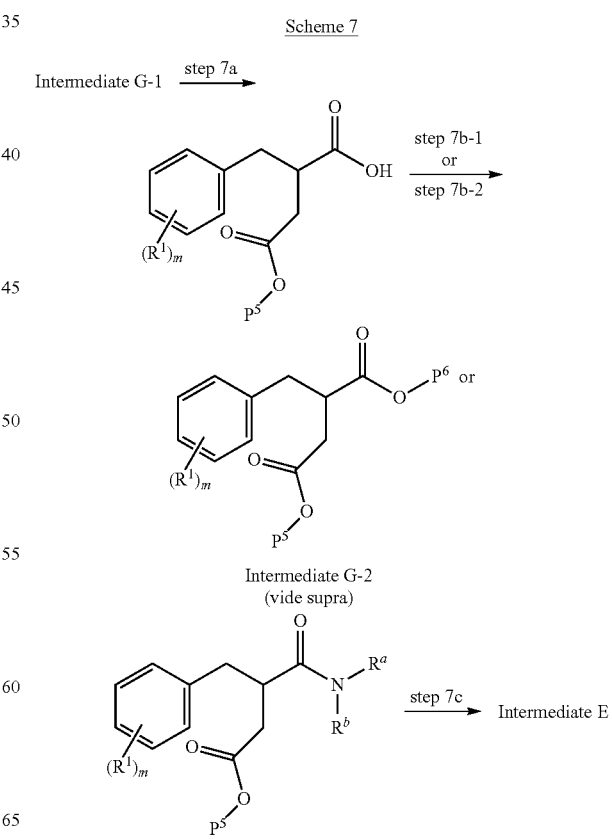

wherein $R^1$, $R^a$, $R^b$, $P^5$, $P^6$ and k are as defined above.

In step 7a, standard methods for cleavage of N-acyloxazolidinone or N-acyloxazinanone of intermediate G-1 can be employed. Illustrative examples of this chemistry are outlined in *Aldrichchimica Acta* 1997, Vo. 30, pp. 3-12 and the references therein.

In step 7b-1, standard methods for esterification of the carboxylic acid can be employed, such as using $TMSCHN_2$ (for methyl ester), $P^6LG$/base (e.g. $K_2CO_3$, $NaHCO_3$, $Cs_2CO_3$ or $K_3PO_4$), thionyl chloride (or oxalyl chloride)/ $P^6OH$, DCC (or EDCI)/DMAP/$P^6OH$, BOP/$P^6OK$ (or $P^6ONa$), $(P^6O)_2CHNMe_2$, CDI/DBU/$P^6OH$, isobutylene/ $H_2SO_4$ (for tert-butyl ester).

In step 7b-2, standard methods for amidation of the carboxylic acid can be employed, using coupling reagents such as DCC, EDCI, PyBOP or BOP in presence or absence of a reagent such as 1-hydroxybenazotriazole, 1-hydroxy-7-azabenzotriazole or pentafluorophenol.

In step 7c, standard methods for removing $P^5$ protecting groups can be applied, such as base hydrolysis using NaOH, KOH, or LiOH, acid hydrolysis using TFA or HCl, or hydrogenation using palladium-on-carbon under hydrogen.

Intermediate F can be prepared following the synthetic route outlined in "March's advanced organic chemistry: reactions, mechanisms, and structure, 5$^{th}$ Edition", John Wiley and Sons, Inc., NY (2001), either directly or analogously.

Alternatively, the compounds of the invention of formula I can be prepared wherein X is hydroxy by an oxidative cleavage reaction of intermediate H wherein $R^1$, $R^2$, $R^3$, $R^4$, $R^5$, B, m, and n have the definition of Formula I, supra; This oxidative cleavage reaction of the intermediate H can be completed with as oxidizing reagent such as ozone, which is generated from an ozone generator, in a solvent such as acetone or MeOH. This oxidative cleavage reaction can be quenched with a suitable reagent such as dimethyl sulfide and water.

Intermediate H

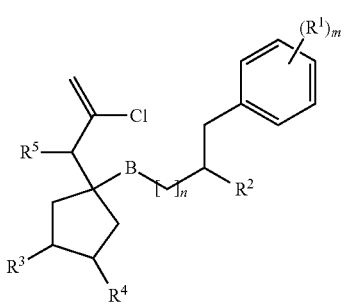

The intermediate H can be prepared using the following process comprising: condensing an intermediate J (wherein $R^3$, $R^4$ and $R^5$ are as previously described) with intermediate C:

Intermediate J

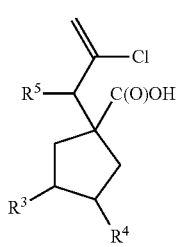

Known condensation methods may be applied including, but not limited to, conversion of the intermediate J to their corresponding acid halide, using reagents such as thionyl chloride or oxalyl chloride, or conversion of intermediate J to mixed anhydride using reagents such as ClC(O)O-isobutyl or 2,4,6-trichlorobenzoyl chloride followed by reaction of the acid halide or mixed anhydride with the intermediate C in presence or absence of a base such as tertiary amine (e.g. triethylamine, DIPEA, or N-methylmorpholine) or pyridine derivative (e.g. pyridine, 4-(dimethylamino)pyridine, or 4-pyrrolidinopyridine). Alternatively, the intermediate J can be coupled with C using coupling reagents such as DCC, EDCI, PyBOP or BOP in presence or absence of a reagent such as 1-hydroxybenazotriazole, 1-hydroxy-7-azabenzotriazole or pentafluorophenol.

Intermediate J can be prepared as according to the following general procedures described in Scheme 8:

Scheme 8

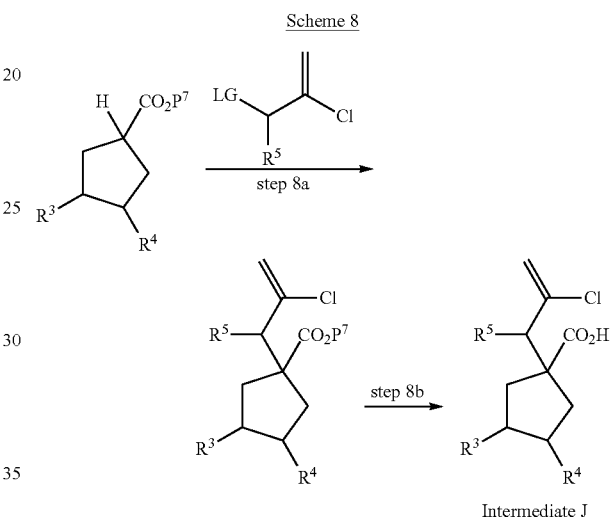

Intermediate J wherein $R^3$, $R^4$, $R^5$ and LG are as previously described and wherein $P^7$ is a protecting group selected from, but not limited to, hydrogen, methyl, ethyl, propyl, tert-butyl, methoxymethyl, tert-butyldimethylsilyl, tetrahydrofuranyl, or phenyl.

In step 8a, standard methods for alpha-allylation of carbonyl group can be applied, using a base such as NHMDS, LHMDS, KHMDS, tert-BuOK, tert-BuONa, NaH, LDA, n-BuLi, sec-BuLi or tert-BuLi.

In step 8b, standard methods for removing $P^7$ protecting groups can be applied, such as base hydrolysis such as using NaOH, KOH or LiOH, or acid hydrolysis such as using TFA or HCl.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known to those skilled in the art.

In another aspect, the present invention provides a pharmaceutical composition comprising a compound of the present invention or a pharmaceutically acceptable salt thereof and one or more pharmaceutically acceptable carriers. The pharmaceutical composition can be formulated for particular routes of administration such as oral administration, parenteral administration, and rectal administration, etc.

In addition, the pharmaceutical compositions of the present invention can be made up in a solid form (including without limitation capsules, tablets, pills, granules, powders or suppositories), or in a liquid form (including without limitation solutions, suspensions or emulsions). The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers, etc.

Typically, the pharmaceutical compositions are tablets or gelatin capsules comprising the active ingredient together with a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets may contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with a suitable carrier. Carriers suitable for transdermal delivery include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They may be conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds according to anyone of formulae I to VI, or a pharmaceutically acceptable salt thereof, in free form or in pharmaceutically acceptable salt form, exhibit valuable pharmacological properties, e.g. neutral endopeptidase EC 3.4.24.11 modulating properties, e.g. as indicated in in vitro and in vivo tests as provided in the next sections and are therefore indicated for therapy.

Compounds of the invention or a pharmaceutically acceptable salt thereof, may be useful in the treatment of an indication selected from hypertension, pulmonary hypertension, pulmonary arterial hypertension, isolated systolic hypertension, resistant hypertension, peripheral vascular disease, heart failure, congestive heart failure, left ventricular hypertrophy, angina, renal insufficiency (diabetic or non-diabetic), renal failure (including edema and salt retention), diabetic nephropathy, non-diabetic nephropathy, contrast induced nephropathy, nephroic syndrome, glomerulonephritis, scleroderma, glomerular sclerosis, proteinurea of primary renal disease, renal vascular hypertention, diabetic retinopathy and end-stage renal disease (ESRD), endothelial dysfunction, diastolic dysfunction, hypertrophic cardiomyopathy, diabetic cardiac myopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), renal failure (including edema and salt retension), cyclical oedema, Menieres disease, hyperaldosteroneism (primary and secondary) and hypercalciuria, ascites, glaucoma, menstrual disorders, preterm labor, pre-eclampsia, endometriosis, and reproductive disorders (especially male and female infertility, polycystic ovarian syndrome, implantation failure), asthma, obstructive sleep apnea, inflammation, leukemia, pain, epilepsy, affective disorders such as depression and psychotic condition such as dementia and geriatric confusion, obesity and gastrointestinal disorders (especially diarrhea and irritable bowel syndrome), wound healing (especially diabetic and venous ulcers and pressure sores), septic shock, gastric acid secretion dysfunctions, hyperreninaemia, cystic fibrosis, restenosis, type-2 diabetes, metabolic syndrome, diabetic complications and atherosclerosis, male and female sexual dysfunction. Thus, as a further embodiment, the present invention provides the use of a compound according to anyone of formulae I to VI, or a pharmaceutically acceptable salt thereof. In a further embodiment, the therapy is selected from a disease which is associated with neutral endopeptidase EC 3.4.24.11 activity. In another embodiment, the disease is selected from the aforementioned list, suitably hypertension, pulmonary hypertension, pulmonary arterial hypertension, isolated systolic hypertension, resistant hypertension, peripheral vascular disease, heart failure, congestive heart failure, left ventricular hypertrophy, angina, renal insufficiency, renal failure (including edema and salt retension), diabetic nephropathy, non-diabetic nephropathy, contrast induced nephropathy, type-2 diabetes, and diabetic complications and most suitably cardiovascular disorders, such as hypertension, renal insufficiency including edema and congestive heart failure.

Thus, as a further embodiment, the present invention provides the use of a compound according to anyone of formulae I to VI, or a pharmaceutically acceptable salt thereof, in therapy. In a further embodiment, the therapy is selected from a disease which may be treated by inhibiting neutral endopeptidase EC. 3.4.24.11. activity.

In another embodiment, the invention provides a method of treating a disease which is associated with neutral endopeptidase EC 3.4.24.11 activity comprising administration of a therapeutically acceptable amount of a compound according to anyone of formulae I to VI, or a pharmaceutically acceptable salt thereof. In a further embodiment, the disease is selected from the afore-mentioned list, suitably hypertension, pulmonary hypertension, pulmonary arterial hypertension, isolated systolic hypertension, resistant hypertension, peripheral vascular disease, heart failure, congestive heart failure, left ventricular hypertrophy, angina, renal insufficiency, renal failure (including edema and salt retension), diabetic nephropathy, non-diabetic nephropathy, contrast induced nephropathy, type-2 diabetes, and diabetic complications and most suitably cardiovascular disorders, such as hypertension, renal insufficiency including edema and congestive heart failure.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods and/or by the following in vitro & in vivo methods well-described in the art. See A fluorescence lifetime-based assay for protease inhibitor profiling on human kallikrein 7 Doering K, Meder G, Hinnenberger M, Woelcke J, Mayr L M, Hassiepen U Biomol Screen. 2009 January; 14(1):1-9.

In particular, the in vitro inhibition of recombinant human neutral endopeptidase (NEP, EC 3.4.24.11) can be determined as follows:

Recombinant human neutral endopeptidase (expressed in insect cells and purified using standard methods, final concentration 7 pM) is pre-incubated with test compounds at various concentrations for 1 hour at room temperature in 10 mM sodium phosphate buffer at pH 7.4, containing 150 mM NaCl and 0.05% (w/v) CHAPS. The enzymatic reaction is started by the addition of a synthetic peptide substrate Cys (PT14)-Arg-Arg-Leu-Trp-OH to a final concentration of 0.7 µM. Substrate hydrolysis leads to an increase fluorescence lifetime (FLT) of PT14 measured by the means of a FLT reader as described by Doering et al. (2009). The effect of the compound on the enzymatic activity was determined after 1 hour (t=60 min) incubation at room temperature. The IC50 values, corresponding to the inhibitor concentration showing 50% reduction of the FLT values measured in absence of inhibitor, are calculated from the plot of percentage of inhibition vs. inhibitor concentration using non-linear regression analysis software.

Using the test assay (as described above) compounds of the invention exhibited inhibitory efficacy in accordance to Table 1, provided infra.

TABLE 1

Inhibitory Activity of Compounds

| Compounds: Example # | Human NEP IC$_{50}$ (nM) |
|---|---|
| Example 1-1 | 12 |
| Example 1-7 | 15 |
| Example 8-1 | 6 |
| Example 9-1 | 40 |
| Example 9-2 | 11 |
| Example 31-2 | 10 |

The compound of the present invention may be administered either simultaneously with, or before or after, one or more other therapeutic agent. The compound of the present invention may be administered separately, by the same or different route of administration, or together in the same pharmaceutical composition as the other agents.

In one embodiment, the invention provides a product comprising a compound according to anyone of formulae I to VI, or a pharmaceutically acceptable salt thereof, and at least one other therapeutic agent as a combined preparation for simultaneous, separate or sequential use in therapy. In one embodiment, the therapy is the treatment of a disease or condition associated with neutral endopeptidase EC 3.4.24.11 activity.

Products provided as a combined preparation include a composition comprising the compound according to anyone of formulae I to VI, or a pharmaceutically acceptable salt thereof, and the other therapeutic agent(s) together in the same pharmaceutical composition, or the compound according to anyone of formulae I to VI, or a pharmaceutically acceptable salt thereof, and the other therapeutic agent(s) in separate form, e.g. in the form of a kit.

In one embodiment, the invention provides a pharmaceutical composition comprising a compound according to anyone of formulae I to VI, or a pharmaceutically acceptable salt thereof, and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound according to anyone of formulae I to VI, or a pharmaceutically acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (ii) in the patient themselves, e.g. during sequential administration of the compound of the invention and the other therapeutic agent. Accordingly, the invention provides the use of a compound according to anyone of formulae I to VI, or a pharmaceutically acceptable salt thereof, for treating a disease or condition associated with neutral endopeptidase EC 3.4.24.11 activity, wherein the medicament is prepared for administration with another therapeutic agent. The invention also provides the use of another therapeutic agent for treating a disease or condition associated with neutral endopeptidase EC 3.4.24.11 activity, wherein the medicament is administered with a compound according to anyone of formulae I to VI, or a pharmaceutically acceptable salt thereof.

The invention also provides a compound according to anyone of formulae I to VI, or a pharmaceutically acceptable salt thereof, for use in a method of treating a disease or condition associated with neutral endopeptidase EC 3.4.24.11 activity, wherein the compound according to anyone of formulae I to VI, or a pharmaceutically acceptable salt thereof, is prepared for administration with another therapeutic agent. The invention also provides another therapeutic agent for use in a method of treating a disease or condition associated with neutral endopeptidase EC 3.4.24.11 activity, wherein the other therapeutic agent is prepared for administration with a compound according to anyone of formulae I to VI, or a pharmaceutically acceptable salt thereof. The invention also provides a compound according to anyone of formulae I to VI, or a pharmaceutically acceptable salt thereof, for use in a method of treating a disease or condition associated with neutral endopeptidase EC 3.4. 24.11 activity, wherein the compound according to anyone of formulae I to VI or a pharmaceutically acceptable salt thereof, is administered with another therapeutic agent. The invention also provides another therapeutic agent for use in a method of treating a disease or condition associated with neutral endopeptidase EC 3.4.24.11 activity, wherein the other therapeutic agent is administered with a compound according to anyone of formulae I to VI, or a pharmaceutically acceptable salt thereof.

The invention also provides the use of a compound according to anyone of formulae I to VI or a pharmaceutically acceptable salt thereof, for treating a disease or condition associated with neutral endopeptidase EC 3.4.24.11 activity, wherein the patient has previously (e.g. within 24 hours) been treated with another therapeutic agent. The invention also provides the use of another therapeutic agent for treating a disease or condition associated with neutral endopeptidase EC 3.4.24.11 activity, wherein the patient has previously (e.g. within 24 hours) been treated with a compound according to anyone of formulae I to VI, or a pharmaceutically acceptable salt thereof.

In one embodiment, the other therapeutic agent is selected from:

In one embodiment, the other therapeutic agent is selected from: HMG-Co-A reductase inhibitor, an anigiotensin receptor blocker (ARBs, angiotensin II receptor antagonist), angiotensin converting enzyme (ACE) Inhibitor, a calcium channel blocker (CCB), an endothelin antagonist, a renin inhibitor, a diuretic, an ApoA-I mimic, an anti-diabetic agent, an obesity-reducing agent, an aldosterone receptor blocker, an endothelin receptor blocker, an aldosterone synthase inhibitors (ASI), a CETP inhibitor and a phophodiesterase type 5 (PDE5) inhibitor.

The term "in combination with" a second agent or treatment includes co-administration of the compound of the invention (e.g., a compound according to anyone of Formulae I-VI or a compound otherwise described herein) with the second agent or treatment, administration of the compound of the invention first, followed by the second agent or treatment and administration of the second agent or treatment first, followed by the compound of the invention.

The term "second agent" includes any agent which is known in the art to treat, prevent, or reduce the symptoms of a disease or disorder described herein, e.g. a disorder or disease responsive to the inhibition of neutral endopeptidase, such as for example, hypertension, pulmonary hypertension, pulmonary arterial hypertension, isolated systolic hypertension, resistant hypertension, peripheral vascular disease, heart failure, congestive heart failure, left ventricular hypertrophy, angina, renal insufficiency (diabetic or non-diabetic), renal failure (including edema and salt retension), diabetic nephropathy, non-diabetic nephropathy, contrast induced nephropathy, nephroic syndrome, glomerulonephritis, scleroderma, glomerular sclerosis, proteinurea of primary renal disease, renal vascular hypertention, diabetic retinopathy and end-stage renal disease (ESRD), endothelial dysfunction, diastolic dysfunction, hypertrophic cardiomyopathy, diabetic cardiac myopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), renal failure (including edema and salt retension), cyclical oedema, Menieres disease, hyperaldosteroneism (primary and secondary) and hypercalciuria, ascites, glaucoma, menstrual disorders, preterm labor, pre-eclampsia, endometriosis, and reproductive disorders (especially male and female infertility, polycystic ovarian syndrome, implantation failure), asthma, obstructive sleep apnea, inflammation, leukemia, pain, epilepsy, affective disorders such as depression and psychotic condition such as dementia and geriatric confusion, obesity and gastrointestinal disorders (especially diarrhea and irritable bowel syndrome), wound healing (especially diabetic and venous ulcers and pressure sores), septic shock, the modulation of gastric acid secretion, the treatment of hyperreninaemia, cystic fibrosis, restenosis, type-2 diabetes, metabolic syndrome, diabetic complications and atherosclerosis, male and female sexual dysfunction.

Examples of second agents include HMG-Co-A reductase inhibitors, angiotensin II receptor antagonists, angiotensin converting enzyme (ACE) Inhibitors, calcium channel blockers (CCB), endothelin antagonists, renin inhibitors, diuretics, ApoA-I mimics, anti-diabetic agents, obesity-reducing agents, aldosterone receptor blockers, endothelin receptor blockers, aldosterone synthase inhibitors (ASI) and CETP inhibitors.

The term "HMG-Co-A reductase inhibitor" (also called beta-hydroxy-beta-methylglutaryl-co-enzyme-A reductase inhibitors) includes active agents that may be used to lower the lipid levels including cholesterol in blood. Examples include atorvastatin, cerivastatin, compactin, dalvastatin, dihydrocompactin, fluindostatin, fluvastatin, lovastatin, pitavastatin, mevastatin, pravastatin, rivastatin, simvastatin, and velostatin, or, pharmaceutically acceptable salts thereof.

The term "ACE-inhibitor" (also called angiotensin converting enzyme inhibitors) includes molecules that interrupt the enzymatic degradation of angiotensin I to angiotensin II. Such compounds may be used for the regulation of blood pressure and for the treatment of congestive heart failure. Examples include alacepril, benazepril, benazeprilat, captopril, ceronapril, cilazapril, delapril, enalapril, enaprilat, fosinopril, imidapril, lisinopril, moveltopril, perindopril, quinapril, ramipril, spirapril, temocapril, and trandolapril, or, pharmaceutically acceptables salt thereof.

The term "endothelin antagonist" includes bosentan (cf. EP 526708 A), tezosentan (cf. WO 96/19459), or, pharmaceutically acceptable salts thereof.

The term "renin inhibitor" includes ditekiren (chemical name: [1S-[1R*,2R*,4R*(1R*,2R*)]]-1-[(1,1-dimethylethoxy)carbonyl]-L-proly l-L-phenylalanyl-N-[2-hydroxy-5-methyl-1-(2-methylpropyl)-4-[[[2-methyl-1-[[(2-pyridinylmethyl)amino]carbonyl]butyl]amino]carbonyl]hexyl]-N-alfa-methyl-L-histidinamide); terlakiren (chemical name: [R—(R*,S*)]-N-(4-morpholinylcarbonyl)-L-phenylalanyl-N-[1-(cyclohexylmethyl)-2-hydroxy-3-(1-methylethoxy)-3-oxopropyl]-S-methyl-L-cysteineamide); Aliskiren (chemical name: (2S,4S,5S,7S)-5-amino-N-(2-carbamoyl-2,2-dimethylethyl)-4-hydroxy-7-{[4-methoxy-3-(3-methoxypropoxy)phenyl]methyl}-8-methyl-2-(propan-2-yl)nonanamide) and zankiren (chemical name: [1S-[1R*[R*(R*)],2S*,3R*]]—N-[1-(cyclohexylmethyl)-2,3-dihydroxy-5-methylhexyl]-alfa-[[2-[[(4-methyl-1-piperazinypsulfonyl]methyl]-1-oxo-3-phenylpropyl]amino]-4-thiazolepropanamide), or, hydrochloride salts thereof, or, SPP630, SPP635 and SPP800 as developed by Speedel, or RO 66-1132 and RO 66-1168 of Formula (A) and (B):

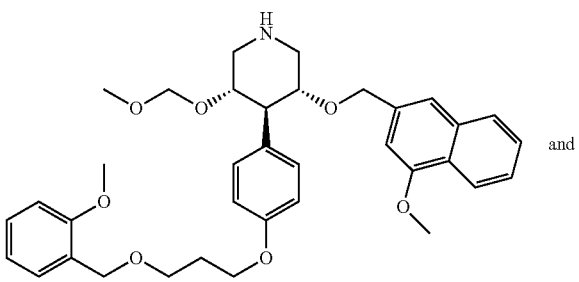

(A)

and

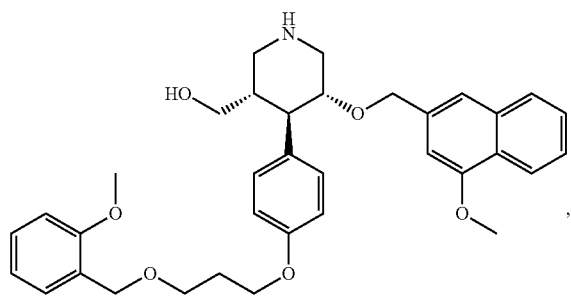

(B)

or, pharmaceutically acceptable salts thereof.

The term "aliskiren", if not defined specifically, is to be understood both as the free base and as a salt thereof, especially a pharmaceutically acceptable salt thereof, most preferably a hemi-fumarate salt thereof.

An angiotensin II receptor antagonist or a pharmaceutically acceptable salt thereof is understood to be an active ingredient which bind to the $AT_1$-receptor subtype of angiotensin II receptor but do not result in activation of the receptor. As a consequence of the inhibition of the $AT_1$ receptor, these antagonists can, for example, be employed as antihypertensives or for treating congestive heart failure.

The class of $AT_1$ receptor antagonists comprises compounds having differing structural features, essentially preferred are the non-peptidic ones. For example, mention may be made of the compounds which are selected from the group consisting of valsartan, losartan, candesartan, eprosartan, irbesartan, saprisartan, tasosartan, telmisartan, the compound with the designation E-1477 of the following formula

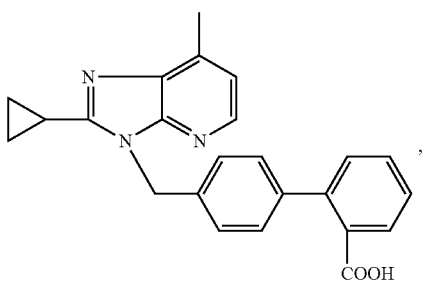 [SMILES: Cc1ccnc2c1nc(C1CC1)n2Cc1ccc(-c2ccccc2C(=O)O)cc1]

the compound with the designation SC-52458 of the following formula

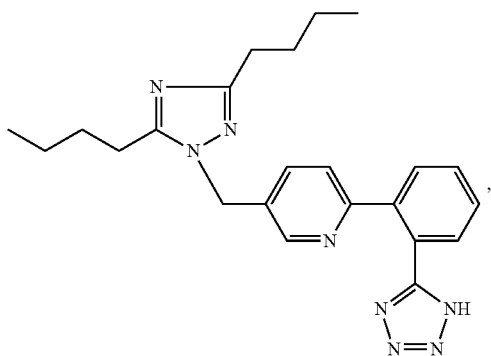 [SMILES: CCCCc1nc(CCCC)n(Cc2ccc(-c3ccccc3-c3nnn[nH]3)nc2)n1]

and the compound with the designation ZD-8731 of the following formula

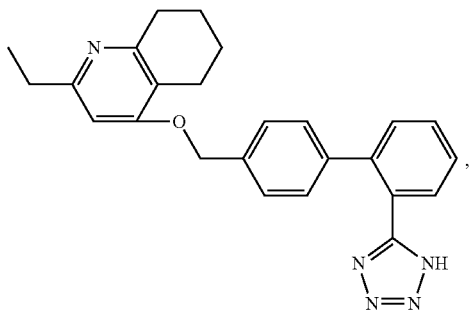 [SMILES: CCc1cc(OCc2ccc(-c3ccccc3-c3nnn[nH]3)cc2)c2c(n1)CCCC2]

or, in each case, a pharmaceutically acceptable salt thereof.

Preferred $AT_1$-receptor antagonist are those agents which have been marketed, most preferred is valsartan or a pharmaceutically acceptable salt thereof.

The term "calcium channel blocker (CCB)" includes dihydropyridines (DHPs) and non-DHPs (e.g., diltiazem-type and verapamil-type CCBs). Examples include amlodipine, felodipine, ryosidine, isradipine, lacidipine, nicardipine, nifedipine, niguldipine, niludipine, nimodipine, nisoldipine, nitrendipine, and nivaldipine, and is preferably a non-DHP representative selected from the group consisting of flunarizine, prenylamine, diltiazem, fendiline, gallopamil, mibefradil, anipamil, tiapamil and verapamil, or, pharmaceutically acceptable salts thereof. CCBs may be used as anti-hypertensive, anti-angina pectoris, or anti-arrhythmic drugs.

The term "diuretic" includes thiazide derivatives (e.g., chlorothiazide, hydrochlorothiazide, methylclothiazide, and chlorothalidon).

The term "ApoA-I mimic" includes D4F peptides (e.g., formula D-W-F-K-A-F-Y-D-K-V-A-E-K-F-K-E-A-F)

The term "anti-diabetic agent" includes insulin secretion enhancers that promote the secretion of insulin from pancreatic β-cells. Examples include biguanide derivatives (e.g., metformin), sulfonylureas (SU) (e.g., tolbutamide, chlorpropamide, tolazamide, acetohexamide, 4-chloro-N-[(1-pyrrolidinylamino)carbonyl]-benzensulfonamide (glycopyramide), glibenclamide (glyburide), gliclazide, 1-butyl-3-metanilylurea, carbutamide, glibonuride, glipizide, gliquidone, glisoxepid, glybuthiazole, glibuzole, glyhexamide, glymidine, glypinamide, phenbutamide, and tolylcyclamide), or pharmaceutically acceptable salts thereof. Further examples include phenylalanine derivatives (e.g., nateglinide [N-(trans-4-isopropylcyclohexylcarbonyl)-D-phenylalanine] (cf. EP 196222 and EP 526171) of the formula

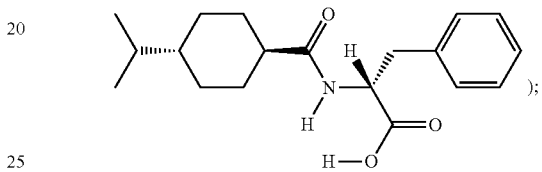

repaglinide [(S)-2-ethoxy-4-{2-[[3-methyl-1-[2-(1-piperidinyl)phenyl]butyl]amino]-2-oxoethyl}benzoic acid] (cf. EP 589874, EP 147850A2, in particular Example 11 on page 61, and EP 207331 A1); calcium (2S)-2-benzyl-3-(cis-hexahydro-2-isoindolinlycarbonyl)-propionate dihydrate (e.g., mitiglinide (cf. EP 507534)); and glimepiride (cf. EP 31058). Further examples include DPP-IV inhibitors, GLP-1 and GLP-1 agonists.

DPP-IV is responsible for inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal.

The DPP-IV inhibitor can be peptidic or, preferably, non-peptidic. DPP-IV inhibitors are in each case generically and specifically disclosed e.g. in WO 98/19998, DE 196 16 486 A1, WO 00/34241 and WO 95/15309, in each case in particular in the compound claims and the final products of the working examples, the subject-matter of the final products, the pharmaceutical preparations and the claims are hereby incorporated into the present application by reference to these publications. Preferred are those compounds that are specifically disclosed in Example 3 of WO 98/19998 and Example 1 of WO 00/34241, respectively.

GLP-1 is an insulinotropic protein which is described, e.g., by W. E. Schmidt et al. in *Diabetologia*, 28, 1985, 704-707 and in U.S. Pat. No. 5,705,483.

The term "GLP-1 agonists" includes variants and analogs of GLP-1(7-36)$NH_2$ which are disclosed in particular in U.S. Pat. No. 5,120,712, U.S. Pat. No. 5,118,666, U.S. Pat. No. 5,512,549, WO 91/11457 and by C. Orskov et al in J. Biol. Chem. 264 (1989) 12826. Further examples include GLP-1 (7-37), in which compound the carboxy-terminal amide functionality of $Arg^{36}$ is displaced with Gly at the $37^{th}$ position of the GLP-1(7-36)$NH_2$ molecule and variants and analogs thereof including $GLN^9$-GLP-1(7-37), D-$GLN^9$-GLP-1(7-37), acetyl $LYS^9$-GLP-1(7-37), $LYS^{18}$-GLP-1(7-37) and, in particular, GLP-1(7-37)OH, $VAL^8$-GLP-1(7-37), $GLY^8$-GLP-1(7-37), $THR^8$-GLP-1(7-37), $MET^8$-GLP-1(7-37) and 4-imidazopropionyl-GLP-1. Special preference is also given to the GLP agonist analog exendin-4, described by Greig et al. in Diabetologia 1999, 42, 45-50.

Also included in the definition "anti-diabetic agent" are insulin sensitivity enhancers which restore impaired insulin receptor function to reduce insulin resistance and consequently enhance the insulin sensitivity. Examples include hypoglycemic thiazolidinedione derivatives (e.g., glitazone, (S)-((3,4-dihydro-2-(phenyl-methyl)-2H-1-benzopyran-6-yl)methyl-thiazolidine-2,4-dione (englitazone), 5-{[4-(3-(5-methyl-2-phenyl-4-oxazolyl)-1-oxopropyl)-phenyl]-methyl}-thiazolidine-2,4-dione (darglitazone), 5-{[4-(1-methyl-cyclohexyl)methoxy)-phenyl]methyl}-thiazolidine-2,4-dione (ciglitazone), 5-{[4-(2-(1-indolyl)ethoxy)phenyl]methyl}-thiazolidine-2,4-dione (DRF2189), 5-{4-[2-(5-methyl-2-phenyl-4-oxazolyl)-ethoxy)]benzyl}-thiazolidine-2,4-dione (BM-13.1246), 5-(2-naphthylsulfonyl)-thiazolidine-2,4-dione (AY-31637), bis{4-[(2,4-dioxo-5-thiazolidinypmethyl]phenyl}methane (YM268), 5-{4-[2-(5-methyl-2-phenyl-4-oxazolyl)-2-hydroxyethoxy]benzyl}-thiazolidine-2,4-dione (AD-5075), 5-[4-(1-phenyl-1-cyclopropanecarbonylamino)-benzyl]thiazolidine-2,4-dione (DN-108) 5-{[4-(2-(2,3-dihydroindol-1-yl)ethoxy)phenyl] methyl}-thiazolidine-2,4-dione, 5-[3-(4-chloro-phenyl])-2-propynyl]-5-phenylsulfonyl)thiazolidine-2,4-dione, 5-[3-(4-chlorophenyl])-2-propynyl]-5-(4-fluorophenyl-sulfonyl) thiazolidine-2,4-dione, 5-{[4-(2-(methyl-2-pyridinyl-amino)-ethoxy)phenyl]methyl}-thiazolidine-2,4-dione (rosiglitazone), 5-{[4-(2-(5-ethyl-2-pyridyl)ethoxy)phenyl] methyl}thiazolidine-2,4-dione (pioglitazone), 5-{[4-((3,4-dihydro-6-hydroxy-2,5,7,8-tetramethyl-2H-1-benzopyran-2-yl)methoxy)-phenyl]-methyl}-thiazolidine-2,4-dione (troglitazone), 5-[6-(2-fluoro-benzyloxy)naphthalen-2-ylmethyl]-thiazolidine-2,4-dione (MCC555), 5-{[2-(2-naphthyl)-benzoxazol-5-yl]-methyl}thiazolidine-2,4-dione (T-174) and 5-(2,4-dioxothiazolidin-5-ylmethyl)-2-methoxy-N-(4-trifluoromethyl-benzyl)benzamide (KRP297)).

Further anti-diabetic agents include, insulin signalling pathway modulators, like inhibitors of protein tyrosine phosphatases (PTPases), antidiabetic non-small molecule mimetic compounds and inhibitors of glutamine-fructose-6-phosphate amidotransferase (GFAT); compounds influencing a dysregulated hepatic glucose production, like inhibitors of glucose-6-phosphatase (G6Pase), inhibitors of fructose-1,6-bisphosphatase (F-1,6-Bpase), inhibitors of glycogen phosphorylase (GP), glucagon receptor antagonists and inhibitors of phosphoenolpyruvate carboxykinase (PEPCK); pyruvate dehydrogenase kinase (PDHK) inhibitors; inhibitors of gastric emptying; insulin; inhibitors of GSK-3; retinoid X receptor (RXR) agonists; agonists of Beta-3 AR; agonists of uncoupling proteins (UCPs); non-glitazone type PPARγ agonists; dual PPARα/PPARγ agonists; antidiabetic vanadium containing compounds; incretin hormones, like glucagon-like peptide-1 (GLP-1) and GLP-1 agonists; beta-cell imidazoline receptor antagonists; miglitol; $α_2$-adrenergic antagonists; and pharmaceutically acceptable salts thereof.

The term "obesity-reducing agent" includes lipase inhibitors (e.g., orlistat) and appetite suppressants (e.g., sibutramine and phentermine).

An aldosterone synthase inhibitor or a pharmaceutically acceptable salt thereof is understood to be an active ingredient that has the property to inhibit the production of aldosterone. Aldosterone synthase (CYP11B2) is a mitochondrial cytochrome P450 enzyme catalyzing the last step of aldosterone production in the adrenal cortex, i.e., the conversion of 11-deoxycorticosterone to aldosterone. The inhibition of the aldosterone production with so-called aldosterone synthase inhibitors is known to be a successful variant to treatment of hypokalemia, hypertension, congestive heart failure, atrial fibrillation or renal failure. Such aldosterone synthase inhibition activity is readily determined by those skilled in the art according to standard assays (e.g., US 2007/0049616).

The class of aldosterone synthase inhibitors comprises both steroidal and non-steroidal aldosterone synthase inhibitors, the later being most preferred.

Preference is given to commercially available aldosterone synthase inhibitors or those aldosterone synthase inhibitors that have been approved by the health authorities.

The class of aldosterone synthase inhibitors comprises compounds having differing structural features. For example, mention may be made of the compounds which are selected from the group consisting of the non-steroidal aromatase inhibitors anastrozole, fadrozole (including the (+)-enantiomer thereof), as well as the steroidal aromatase inhibitor exemestane, or, in each case where applicable, a pharmaceutically acceptable salt thereof.

The most preferred non-steroidal aldosterone synthase inhibitor is the (+)-enantiomer of the hydrochloride of fadrozole (U.S. Pat. Nos. 4,617,307 and 4,889,861) of formula

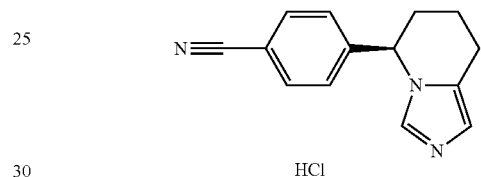

or, if appropriable, a pharmaceutically acceptable salt thereof.

A preferred steroidal aldosterone antagonist is eplerenone (cf. EP 122232 A) of the formula

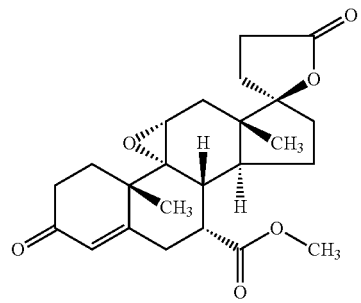

or Spironolactone; or, in each case, if appropriable, a pharmaceutically acceptable salt thereof.

Aldosterone synthase inhibitors useful in said combination are compounds and analogs generically and specifically disclosed e.g. in US2007/0049616, in particular in the compound claims and the final products of the working examples, the subject-matter of the final products, the pharmaceutical preparations and the claims are hereby incorporated into the present application by reference to this publication. Preferred aldosterone synthase inhibitors suitable for use in the present invention include, without limitation 4-(6,7-dihydro-5H-pyrrolo[1,2-c]imidazol-5-yl)-3-methylbenzonitrile; 5-(2-chloro-4-cyanophenyl)-6,7-dihydro-5H-pyrrolo[1,2-c]imidazole-5-carboxylic acid (4-methoxybenzyl)methylamide; 4'-fluoro-6-(6,7,8,9-tetrahydro-5H-imidazo[1,5-a]azepin-5-yl)biphenyl-3-carbonitrile; 5-(4-Cyano-2-methoxyphenyl)-6,7-dihydro-5H-pyrrolo[1,2-c]imidazole-5-carboxylic acid butyl ester; 4-(6,7-Dihydro-5H-pyrrolo[1,2-c]imidazol-5-yl)-2-methoxybenzonitrile; 5-(2-Chloro-4-cyanophenyl)-6,7-dihydro-5H-pyrrolo[1,2-c]imidazole-5-carboxylic acid 4-fluorobenzyl ester; 5-(4-Cyano-2-trifluoromethoxyphenyl)-6,7-dihydro-5H-pyrrolo[1,2-c]imidazole-5-carboxylic acid methyl ester; 5-(4-Cyano-2-methoxyphenyl)-6,7-dihydro-5H-pyrrolo[1,2-c]imidazole-5-carboxylic acid 2-isopropoxyethyl ester; 4-(6,7-Dihydro-5H-pyrrolo[1,2-c]imidazol-5-yl)-2-methylbenzonitrile; 4-(6,7-dihydro-5H-pyrrolo[1,2-c]imidazol-5-yl)-3-fluorobenzonitrile; 4-(6,7-Dihydro-5H-pyrrolo[1,2-c]imidazol-5-yl)-2-nnethoxybenzonitrile; 3-Fluoro-4-(7-methylene-6,7-dihydro-5H-pyrrolo[1,2-c]imidazol-5-yl)benzonitrile; cis-3-Fluoro-4-[7-(4-fluoro-benzyl)-5,6,7,8-tetrahydro-imidazo[1,5-a]pyridin-5-yl]benzonitrile; 4'-Fluoro-6-(9-methyl-6,7,8,9-tetrahydro-5H-imidazo[1,5-a]azepin-5-yl)biphenyl-3-carbonitrile; 4'-Fluoro-6-(9-methyl-6,7,8,9-tetrahydro-5H-imidazo[1,5-a]azepin-5-yl)biphenyl-3-carbonitrile or in each case, the (R) or (S) enantiomer thereof; or if appropriable, a pharmaceutically acceptable salt thereof.

The term aldosterone synthase inhibitors also include compounds and analogs disclosed in WO2008/076860, WO2008/076336, WO2008/076862, WO2008/027284, WO2004/046145, WO2004/014914, WO2001/076574.

Furthermore Aldosterone synthase inhibitors also include compounds and analogs disclosed in U.S. patent applications US2007/0225232, US2007/0208035, US2008/0318978, US2008/0076794, US2009/0012068, US20090048241 and in PCT applications WO2006/005726, WO2006/128853, WO2006128851, WO2006/128852, WO2007065942, WO2007/116099, WO2007/116908, WO2008/119744 and in European patent application EP 1886695. Preferred aldosterone synthase inhibitors suitable for use in the present invention include, without limitation 8-(4-Fluorophenyl)-5,6-dihydro-8H-imidazo[5,1-c1[1,41oxazine; 4-(5,6-Dihydro-8H-imidazo[5,1-c][1,4]oxazin-8-yl)-2-fluorobenzonitrile; 4-(5,6-Dihydro-8H-imidazo[5,1-c][1,4]oxazin-8-yl)-2,6-difluorobenzonitrile; 4-(5,6-Dihydro-8H-imidazo[5,1-c][1,4]oxazin-8-yl)-2-methoxybenzonitrile; 3-(5,6-Dihydro-8H-imidazo[5,1-c][1,4]oxazin-8-yl)benzonitrile; 4-(5,6-Dihydro-8H-imidazo[5,1-c][1,4]oxazin-8-yl)phthalonitrile; 4-(8-(4-Cyanophenyl)-5,6-dihydro-8H-imidazo[5,1-c][1,4]oxazin-8-yl)benzonitrile; 4-(5,6-Dihydro-8H-imidazo[5,1-c][1,4]oxazin-8-yl)benzonitrile; 4-(5,6-Dihydro-8H-imidazo[5,1-c][1,4]oxazin-8-yl)naphthalene-1-carbonitrile; 8-[4-(1H-Tetrazol-5-yl)phenyl]-5,6-dihydro-8H-imidazo[5,1-c][1,4]oxazine as developed by Speedel or in each case, the (R) or (S) enantiomer thereof; or if appropriable, a pharmaceutically acceptable salt thereof.

Preferred Aldosterone Synthase inhibitors suitable for combination in the present invention include, 3-(6-Fluoro-3-methyl-2-pyridin-3-yl-1H-indol-1-ylmethyl)-benzonitrile hydrochloride, 1-(4-Methanesulfonyl-benzyl)-3-methyl-2-pyridin-3-yl-1H-indole, 2-(5-Benzyloxy-pyridin-3-yl)-6-chloro-1-methyl-1H-indole, 5-(3-Cyano-1-methyl-1H-indol-2-yl)-nicotinic acid ethyl ester, N-[5-(6-chloro-3-cyano-1-methyl-1H-indol-2-yl)-pyridin-3-ylmethyl]-ethanesulfonamide, Pyrrolidine-1-sulfonic acid 5-(6-chloro-3-cyano-1-methyl-1H-indol-2-yl)-pyridin-3-yl ester, N-Methyl-N-[5-(1-methyl-1H-indol-2-yl)-pyridin-3-ylmethyl]-methanesulfonamide, 6-Chloro-1-methyl-2-{5-[(2-pyrrolidin-1-yl-ethylamino)-methyl]-pyridin-3-yl}-1H-indole-3-carbonitrile, 6-Chloro-2-[5-(4-methanesulfonyl-piperazin-1-ylmethyl)-pyridin-3-yl]-1-methyl-1H-indole-3-carbonitrile, 6-Chloro-1-methyl-2-{5-[(1-methyl-piperidin-4-ylamino)-methyl]-pyridin-3-}-1H-indole-3-carbonitrile, Morpholine-4-carboxylic acid [5-(6-chloro-3-cyano-1-methyl-1H-indol-2-yl)-pyridin-3-ylmethyl]-amide, N-[5-(6-Chloro-1-methyl-1H-1-indol-2-yl)-pyridin-3-ylmethyl]-ethanesulfonamide, C,C,C-Trifluoro-N-[5-(1-methyl-1H-indol-2-yl)-pyridin-3-ylmethyl]-methanesulfonamide, N-[5-(3-Chloro-4-cyano-phenyl)-pyridin-3-yl]-4-trifluoromethyl-benzenesulfonamide, N-[5-(3-Chloro-4-cyano-phenyl)-pyridin-3-yl]-1-phenyl-methanesulfonamide, N-(5-(3-chloro-4-cyanophenyl)pyridin-3-yl)butane-1-sulfonamide, N-(1-(5-(4-cyano-3-methoxyphenyl)pyridin-3-yl)ethyl) ethanesulfonamide N-((5-(3-chloro-4-cyanophenyl)pyridin-3-cyclopropyl)methy)ethanesulfonamide, N-(cyclopropyl(5-(1H-indol-5-yl)pyridin-3-yl)methyl)ethanesulfonamide, N-(cyclopropyl(5-naphtalen-1-yl-pyridin-3-yl)methyl) ethanesulfonamide, Ethanesulfonic acid [5-(6-chloro-1-methyl-1H-pyrrolo[2,3-b]pyridin-2-yl)-pyridin-3-ylmethyl]-amide and Ethanesulfonic acid {[5-(3-chloro-4-cyanophenyl)-pyridin-3-yl]-cyclopropyl-methyl}-ethyl-amide, The term "endothelin receptor blocker" includes bosentan.

The term "CETP inhibitor" refers to a compound that inhibits the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). Examples include compounds disclosed in U.S. Pat. No. 6,140,343 and U.S. Pat. No. 6,197,786 (e.g., [2R,4S]4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester (torcetrapib); compounds disclosed in U.S. Pat. No. 6,723,752 (e.g., (2R)-3-{[3-(4-Chloro-3-ethyl-phenoxy)-phenyl]-[[3-(1,1,2,2-tetrafluoro-ethoxy)-phenyl]-methyl]-amino}-1,1,1-trifluoro-2-propanol); compounds disclosed in U.S. patent application Ser. No. 10/807,838; polypeptide derivatives disclosed in U.S. Pat. No. 5,512,548; rosenonolactone derivatives and phosphate-containing analogs of cholesteryl ester disclosed in *J. Antibiot,* 49(8): 815-816 (1996), and *Bioorg. Med. Chem. Lett;* 6:1951-1954 (1996), respectively. Furthermore, the CETP inhibitors also include those disclosed in WO2000/017165, WO2005/095409 and WO2005/097806.

CETP inhibitors useful in said combination are compounds and analogs generically and specifically disclosed e.g. in WO 2008/009435, WO 2009/059943 and kNO 2009/071509, in particular in the compound claims and the final products of the working examples, the subject-matter of the final products, the pharmaceutical preparations and the claims.

A preferred PDE5 inhibitor is Sildenafil.

Second agent of particular interest include Endothelin antagonists, renin inhibitors, angiotensin II receptor antagonists, calcium channel blockers, diuretics, antidiabetic agents such as DPPIV inhibitors, and aldosterone synthase inhibitors.

In one embodiment, the invention provides a combination, in particular a pharmaceutical combination, comprising a therapeutically effective amount of the compound according to the definition of formula I, II, III, IV, V or VI or a pharmaceutically acceptable salt thereof, and one or more therapeutically active agents selected from HMG-Co-A reductase inhibitors, angiotensin II receptor antagonists, angiotensin converting enzyme (ACE) Inhibitors, calcium channel blockers (CCB), endothelin antagonists, renin inhibitors, diuretics, ApoA-I mimics, anti-diabetic agents, obesity-reducing agents, aldosterone receptor blockers, endothelin receptor blockers, aldosterone synthase inhibitors (ASI) and CETP inhibitors.

In one embodiment, the invention provides a method of inhibiting neutral endopeptidase EC 3.4.24.11 activity in a subject, wherein the method comprises administering to the subject a therapeutically effective amount of the compound according to the definition of formula I, II, III, IV, V or VI or a pharmaceutically acceptable salt thereof.

In one embodiment, the invention provides a method of treating a disorder or a disease in a subject associated with neutral endopeptidase EC 3.4.24.11 activity, wherein the method comprises administering to the subject a therapeutically effective amount of the compound according to the definition of formula I, II, III, IV, V or VI or a pharmaceutically acceptable salt thereof.

In one embodiment, the invention provides a method of treating a disorder or a disease in a subject associated with neutral endopeptidase EC 3.4.24.11 activity, wherein the disorder or the disease is selected from hypertension, pulmonary hypertension, pulmonary arterial hypertension, isolated systolic hypertension, resistant hypertension, peripheral vascular disease, heart failure, congestive heart failure, left ventricular hypertrophy, angina, renal insufficiency (diabetic or non-diabetic), renal failure (including edema and salt retension), diabetic nephropathy, non-diabetic nephropathy, contrast induced nephropathy, nephroic syndrome, glomerulonephritis, scleroderma, glomerular sclerosis, proteinurea of primary renal disease, renal vascular hypertension, diabetic retinopathy and end-stage renal disease (ESRD), endothelial dysfunction, diastolic dysfunction, hypertrophic cardiomyopathy, diabetic cardiac myopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), renal failure (including edema and salt retension), cyclical oedema, Menieres disease, hyperaldosteroneism (primary and secondary) and hypercalciuria, ascites, glaucoma, menstrual disorders, preterm labor, pre-eclampsia, endometriosis, and reproductive disorders (especially male and female infertility, polycystic ovarian syndrome, implantation failure), asthma, obstructive sleep apnea, inflammation, leukemia, pain, epilepsy, affective disorders such as depression and psychotic condition such as dementia and geriatric confusion, obesity and gastrointestinal disorders (especially diarrhea and irritable bowel syndrome), wound healing (especially diabetic and venous ulcers and pressure sores), septic shock, gastric acid secretion dysfunction, hyperreninaemia, cystic fibrosis, restenosis, type-2 diabetes, metabolic syndrome, diabetic complications and atherosclerosis, male and female sexual dysfunction.

In one embodiment, the invention provides a compound according to the definition of formula I, II, III, IV, V or VI, for use as a medicament.

In one embodiment, the invention provides the use of a compound according to the definition of formula I, II, III, IV, V or VI or a pharmaceutically acceptable salt thereof, for the treatment of a disorder or disease in a subject associated with neutral endopeptidase EC 3.4. 24.11 activity.

In one embodiment, the invention provides the use of a compound according to the definition of formula I, II, III, IV, V or VI, in the manufacture of a medicament for the treatment of a disorder or disease in a subject characterized by an activity of neutral endopeptidase EC 3.4.24.11, wherein said disorder or disease is in particular selected from hypertension, pulmonary hypertension, pulmonary arterial hypertension, isolated systolic hypertension, resistant hypertension, peripheral vascular disease, heart failure, congestive heart failure, left ventricular hypertrophy, angina, renal insufficiency (diabetic or non-diabetic), renal failure (including edema and salt retension), diabetic nephropathy, non-diabetic nephropathy, contrast induced nephropathy, nephroic syndrome, glomerulonephritis, scleroderma, glomerular sclerosis, proteinurea of primary renal disease, renal vascular hypertention, diabetic retinopathy and end-stage renal disease (ESRD), endothelial dysfunction, diastolic dysfunction, hypertrophic cardiomyopathy, diabetic cardiac myopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), renal failure (including edema and salt retension), cyclical oedema, Menieres disease, hyperaldosteroneism (primary and secondary) and hypercalciuria, ascites, glaucoma, menstrual disorders, preterm labor, pre-eclampsia, endometriosis, and reproductive disorders (especially male and female infertility, polycystic ovarian syndrome, implantation failure), asthma, obstructive sleep apnea, inflammation, leukemia, pain, epilepsy, affective disorders such as depression and psychotic condition such as dementia and geriatric confusion, obesity and gastrointestinal disorders (especially diarrhea and irritable bowel syndrome), wound healing (especially diabetic and venous ulcers and pressure sores), septic shock, gastric acid secretion dysfunction, hyperreninaemia, cystic fibrosis, restenosis, type-2 diabetes, metabolic syndrome, diabetic complications and atherosclerosis, male and female sexual dysfunction In one embodiment, the invention provides the use of a compound according to the definition of formula I, II, III, IV, V or VI, for the treatment of a disorder or disease in a subject characterized by an activity of neutral endopeptidase EC 3.4.24.11, wherein the disorder or disease is selected from hypertension, pulmonary hypertension, pulmonary arterial hypertension, isolated systolic hypertension, resistant hypertension, peripheral vascular disease, heart failure, congestive heart failure, left ventricular hypertrophy, angina, renal insufficiency (diabetic or non-diabetic), renal failure (including edema and salt retension), diabetic nephropathy, non-diabetic nephropathy, contrast induced nephropathy, nephroic syndrome, glomerulonephritis, scleroderma, glomerular sclerosis, proteinurea of primary renal disease, renal vascular hypertention, diabetic retinopathy and end-stage renal disease (ESRD), endothelial dysfunction, diastolic dysfunction, hypertrophic cardiomyopathy, diabetic cardiac myopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), renal failure (including edema and salt retension), cyclical oedema, Menieres disease, hyperaldosteroneism (primary and secondary) and hypercalciuria, ascites, glaucoma, menstrual disorders, preterm labor, pre-eclampsia, endometriosis, and reproductive disorders (especially male and female infertility, polycystic ovarian syndrome, implantation failure), asthma, obstructive sleep apnea, inflammation, leukemia, pain, epilepsy, affective disorders such as depression and psychotic condition such as dementia and geriatric confusion, obesity and gastrointestinal disorders (especially diarrhea and irritable bowel syndrome), wound healing (especially diabetic and venous ulcers and pressure sores), septic shock, gastric acid secretion dysfunction, hyperreninaemia, cystic fibrosis, restenosis, type-2 diabetes, metabolic syndrome, diabetic complications and atherosclerosis, male and female sexual dysfunction

EXEMPLIFICATION OF THE INVENTION

The following examples are intended to illustrate the invention and are not to be construed as being limitations thereon. Temperatures are given in degrees centigrade. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

Exemplification of the Invention

Abbreviations

| | |
|---|---|
| ATP: adenosine 5'-triphosphate | AS: Aldosterone Synthase |
| Alloc: allyloxycarbonyl | BOC: tertiary butyl carboxy |
| BOP: benzotriazole1-yloxy)tris(dimethylamino) phosphonium hexafluorophosphate | BINAP: racemic 2,2'-bis(diphenyl phosphino)-1,1'-binaphthyl |
| br: broad | bs: broad singlet |
| ACN: acetonitrile | HEP: heptane |
| Ac: Acetyl | Atm: atmosphere |
| Aq: aqueous | calcd: calculated |
| Bn: benzyl | Cbz: benzyloxycarbonyl |
| Bu, i-bu and t-Bu: butyl, isobutyl and t-butyl | Pr and i-Pr: propyl and isopropyl |
| CDI: 1,1'-carbonyldiimidazole | COD: 1,5-cyclooctadiene |
| DBU: 1,8-diazabicyclo[5.4.0]undec-7-ene | DCC: 1,3-dicyclohexylcarbodiimide |
| DIAD: diisopropyl azodicarboxylate | DAST: (diethylamino)sulfur trifluoride |
| d: doublet dd: doublet of doublets | DCM: dichloromethane |
| DIEA: diethylisopropylamine | DME: 1,4-dimethoxyethane |
| DMF: N,N-dimethylformamide | DMSO: dimethylsulfoxide |
| DIPEA: N,N-diisopropylethylamine | DMAP: N,N-dimethylaminopyridine |
| Dppb: 1,2-bis(diphenylphosphino)butane | Dppe: 1,2-bis(diphenylphosphino) ethane |
| DAD: diode array detector | DTT: dithiothreitol |
| DPPA: diphenylphosphorylazide | EDCI, EDIC: N-Ethyl-N'-(3-dimethylaminopropyl)carbodiimide hydrochloride |
| EDTA: ethylenediamine tetraacetic acid | ESI: electrospray ionization |
| Et and EtOAc: ethyl and ethyl acetate | EDC: N-Ethyl-N'-(3-dimethylaminopropyl)carbodiimide |
| HATU: O-(7-azobenzotriazol-1-yl)-1,1,3,3-tetramethyluroniumhexafluorophosphate | HOBt: 1-hydroxy-7-azabenzotriazole |
| HPLC: high pressure liquid chromatography | LC and LCMS: liquid chromatography and liquid chromatography and mass spectrometry |
| H: Hour(s) | HOAt: 1-hydroxy-7-azabezotriazole |
| IR: infrared | LDA: lithium diisopropylamide |
| KHMDS: potassium bis(trimethylsilyl)amide | LHMDS: lithium bis(trimethylsilyl)amide |
| LTA: lead tetraacetate | NHMDS: sodium bis(trimethylsilyl)amide |
| MeOD: methanol-d4 | MeOH: methanol |
| MS and HRMS: mass spectrometry and high resolution mass spectrometry | m: multiplet |
| min: minutes | m/z: mass to charge ratio |
| Ms: mesyl | Me: methyl |
| M and mM: Molar and millimolar | Mg: milligram |
| n.d.: not determined | NMR: nuclear magnetic resonance |
| ppm: parts per million | Pr and iPr: propyl and isopropyl |
| Ph: Phenyl | Pd/C: Palladium on Carbom |
| PyBOP: benzotriazol-1-yloxy Tripyrrolidinophosphoniumhexafluorophosphate | RT: room temperature |
| PIDA: iodobenzene bis(trifluoroacetate) | PIFA: iodobenzene diacetate |
| PS: polymer supported | RP: reverse phase |
| s: singlet adn t: triplet | Ts tosyl |
| TEA: trimethylamine | TFAA: trifluoroacetic anhydride |
| TFA: trifluoroacetic acid | THF: tetrahydrofuran |
| Tf: triflate | tBu: tert-butyl |
| TLC: thin layer chromatography | Tris•HCl: aminotris(hydroxymethyl) methane hydrochloride |
| µL, mL and L: microlitre, millilitre and litre | TMS: Trimethylsilyl |
| WSC: water soluble carbodiimide (N-Ethyl-N'-(3-dimethylaminopropyl)carbodiimide | UV: ultraviolet |
| Troc: 2,2,2-trichloroethoxy | |

The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

The compounds in the examples 1-1 to 1-3, 1-6 to 1-12, 2-1 to 15-1 and 31-2 have been found to have $IC_{50}$ values in the range of about 0.001 nM to about 10,000 nM for NEP.

The conditions for measuring the retention times are as follows:

HPLC condition A:
Column: INERTSIL C8-3, 3 μm×33 mm×3.0 mm at 50° C.
Flow rate: 2 ml/min
Mobile phase: A) 5 mM aqueous $HCOONH_4$, B) MeOH/$CH_3CN$ (1/1, v/v)
Gradient: linear gradient from 5% B to 95% B in 2 min
Detection: DAD-UV at 210-400 nm
HPLC condition B:
Column: INERTSIL C8-3, 3 μm×33 mm×3.0 mm at 50° C.
Flow rate: 2 ml/min
Mobile phase: A) 5 mM aqueous $HCOONH_4$, B) MeOH/$CH_3CN$ (1/1, v/v)
Gradient: linear gradient from 40% B to 95% B in 2 min
Detection: DAD-UV at 210-400 nm
HPLC condition C:
Column: INERTSIL C8-3, 3 μm×33 mm×3.0 mm at 50° C.
Flow rate: 2 ml/min
Mobile phase: A) (5 mM $NH_4^+HCOO^-$)/water, B) MeOH/$CH_3CN$ (1/1, v/v)
Gradient: linear gradient from 5% B to 95% B in 2 min
Detection: DAD-UV at 210-400 nm
HPLC condition D:
Column: INERTSIL C8-3, 3 μm×33 mm×3.0 mm at 50° C.
Flow rate: 2 ml/min
Mobile phase: A) 0.1% aqueous Formic acid, B) MeOH/$CH_3CN$ (1/1, v/v)
Gradient: linear gradient from 5% B to 95% B in 2 min
Detection: DAD-UV at 210-400 nm
HPLC condition E:
Column: Inertsil C8-3, 3 μm×33 mm×3.0 mm at 50° C.
Flow rate: 2 ml/min
Mobile phase: A) methanol/acetonitrile (1/1, v/v), B) 5 mM aquesous $HCOONH_4$
Gradient: linear gradient from 40% A to 95% A in 2 min
Detection: UV at 214 nm
HPLC condition F:
Column: INERTSIL C8-3, 3 μm×33 mm×3.0 mm at 50° C.
Flow rate: 2 ml/min
Mobile phase: A) 0.1% aqueous Formic acid, B) MeOH/$CH_3CN$ (1/1, v/v)
Gradient: linear gradient from 40% B to 95% B in 2 min
Detection: DAD-UV at 210-400 nm HPLC condition G:
Column: INERTSIL C8-3, 3 μm×33 mm×3.0 mm at 50° C.
Flow rate: 2 ml/min
Mobile phase: A) 5 mM aqueous $HCOONH_4$, B) MeOH/$CH_3CN$ (1/1, v/v)
Gradient: linear gradient from 70% B to 95% B in 2 min
Detection: DAD-UV at 210-400 nm
HPLC condition H:
Column: INERTSIL C8-3, 3 μm×33 mm×3.0 mm at 50° C.
Flow rate: 2 ml/min
Mobile phase: A) 5 mM aqueous $HCOONH_4$, B) $CH_3CN$
Gradient: linear gradient from 5% B to 95% B in 2 min
Detection: DAD-UV at 210-400 nm Example 1-1

Synthesis of (S)-1-((S)-3-(biphenyl-4-yl)-2-(1-(carboxymethyl)cyclopentanecarboxamido)propanoyl)pyrrolidine-2-carboxylicacid

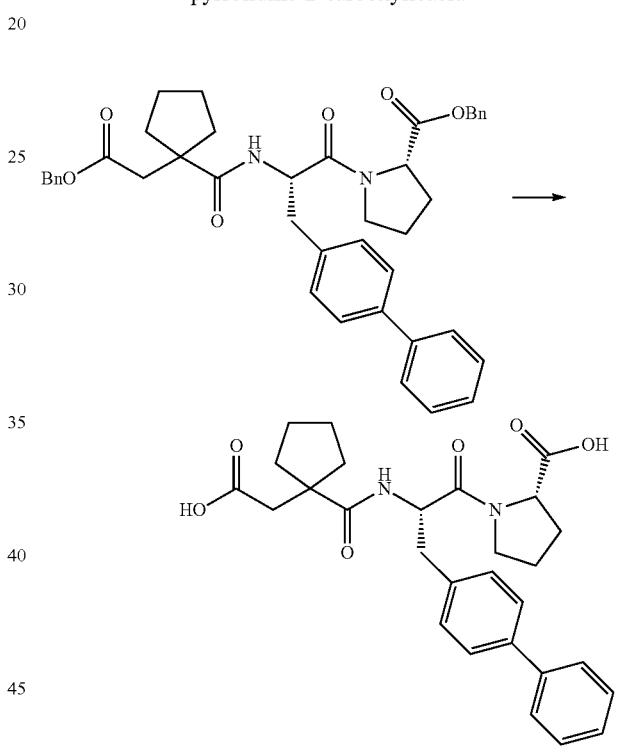

A suspension of (5)-benzyl 14(S)-2-(1-(2-(benzyloxy)-2-oxoethyl)cyclopentanecarboxamido)-3-(biphenyl-4-yl)propanoyl)pyrrolidine-2-carboxylate (445 mg, 0.661 mmol) and Pd/C (141 mg, 0.066 mmol) in EtOH (10 ml) was allowed to stir under hydrogen (1 atm) for 11 hr. The reaction mixture was filtered and the filter cake was washed with MeOH. The filtrate was concentrated, and the obtained residue was purified by RP-HPLC (SunFire C18, $H_2O$ (0.1% TFA)/$CH_3CN$ to give (S)-14(S)-3-(biphenyl-4-yl)-2-(1-(carboxymethyl)cyclopentanecarboxamido)propanoyl)pyrrolidine-2-carboxylic acid (321 mg); Retention time=1.77 minutes (condition B); MS (m+1)=493.2; $^1$H NMR (400 MHz, DMSO-d6, data for major rotamer) δ ppm 1.38-1.57 (m, 6H) 1.81-1.99 (m, 5H) 2.12-2.20 (m, 1H) 2.58 (s, 2H) 2.86-3.03 (m, 2H) 3.51-3.57 (m, 1H) 3.67-3.72 (m, 1H) 4.24-4.26 (m, 1H) 4.73-4.78 (m, 1H) 7.34-7.37 (m, 2H) 7.43-7.47 (m, 2H) 7.52 (d, J=8.1 Hz, 2H) 7.61-7.66 (m, 3H) 12.15 (br s, 2H); HRMS (ES+) m/z for $C_{28}H_{33}N_2O_6$ [M+H]+ calcd 493.2339. found 493.2334.

Following compounds were prepared using similar procedure as described in example 1-1:

| Example # | Product | Reagents |
|---|---|---|
| Example 1-2 | (R)-1-((S)-3-(biphenyl-4-yl)-2-(1-(carboxymethyl)cyclopentanecarboxamido)propanoyl)pyrrolidine-2-carboxylic acid | Pd on carbon, H$_2$ gas, EtOH |
| Example 1-3 | (S)-2-(1-(3-(biphenyl-4-yl)-1-oxo-1-(pyrrolidin-1-yl)propan-2-ylcarbamoyl)cyclopentyl)acetic acid | Pd on carbon, H$_2$ gas, EtOH |
| Example 1-4 | (S)-1-((S)-3-(biphenyl-4-yl)-2-(1-(2-ethoxy-2-oxoethyl)cyclopentanecarboxamido)propanoyl)pyrrolidine-2-carboxylic acid | Pd on carbon, H$_2$ gas, EtOH |
| Example 1-5 | (S)-3-(biphenyl-4-yl)-2-(1-(2-ethoxy-2-oxoethyl)cyclopentanecarboxamido)propanoic acid | Pd on carbon, H$_2$ gas, EtOH |

| Example 1-6 | 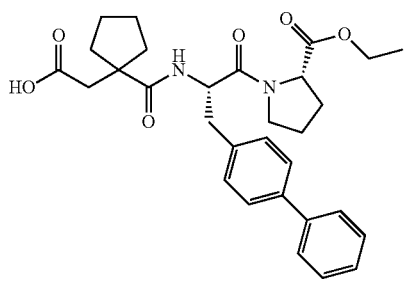 2-(1-(((S)-3-(biphenyl-4-yl)-1-((S)-2-(ethoxycarbonyl)pyrrolidin-1-yl)-1-oxopropan-2-yl)carbamoyl)cyclopentyl)acetic acid | 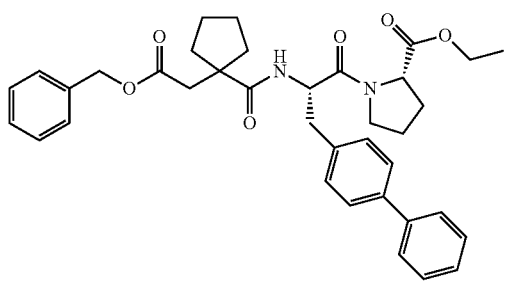 Pd on carbon, H₂ gas, EtOH |
|---|---|---|
| Example 1-7 | 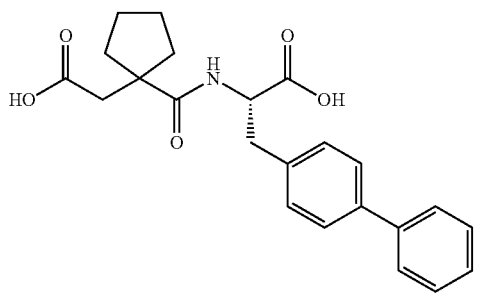 (S)-3-(biphenyl-4-yl)-2-(1-(carboxymethyl)cyclopentanecarboxamido)propanoic acid | 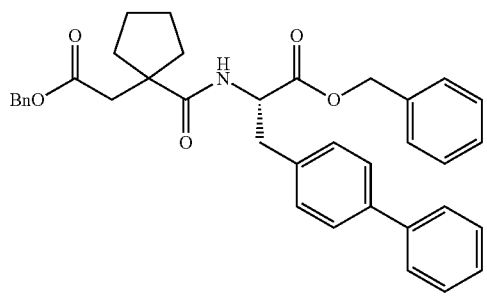 Pd on carbon, H₂ gas, THF |
| Example 1-8 | 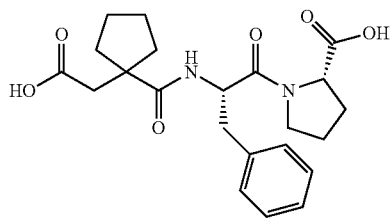 (S)-1-((S)-2-(1-(carboxymethyl)cyclopentanecarboxamido)-3-phenylpropanoyl)pyrrolidine-2-carboxylic acid | 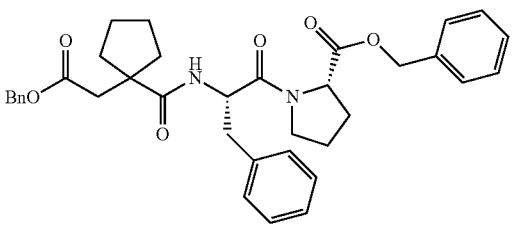 Pd on carbon, H₂ gas, EtOH |
| Example 1-9 | 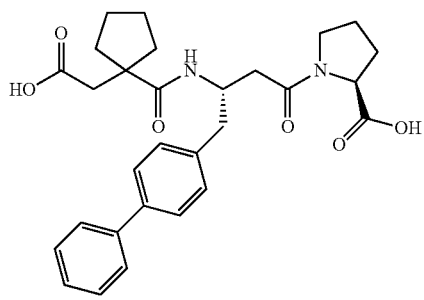 (S)-1-((S)-4-(biphenyl-4-yl)-3-(1-(carboxymethyl)cyclopentanecarboxamido)butanoyl)pyrrolidine-2-carboxylic acid | 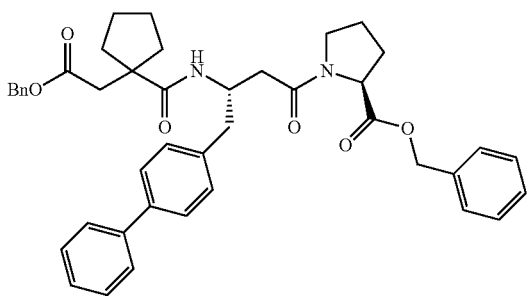 Pd on carbon, H₂ gas, EtOH |

-continued

Example 1-10

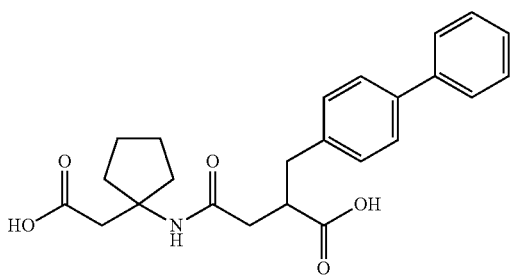

2-(biphenyl-4-ylmethyl)-4-(1-(carboxymethyl)cyclopentylamino)-4-oxobutanoic acid

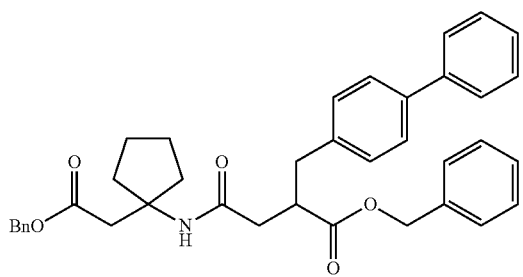

Pd on carbon, H₂ gas, EtOH

Example 1-11

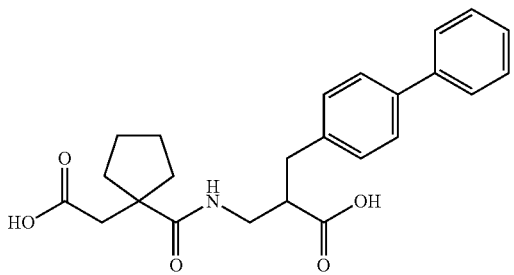

3-(biphenyl-4-yl)-2-((1-(carboxymethyl)cyclopentanecarboxamido)methyl)propanoic acid

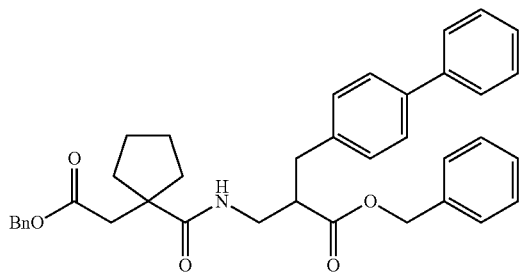

Pd on carbon, H₂ gas, EtOH

Example 1-12

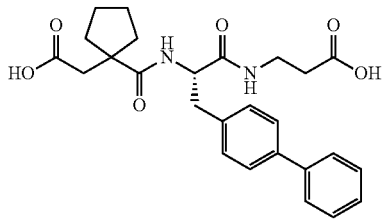

(S)-3-(3-(biphenyl-4-yl)-2-(1-(carboxymethyl)cyclopentanecarboxamido)propanamido)propanoic acid

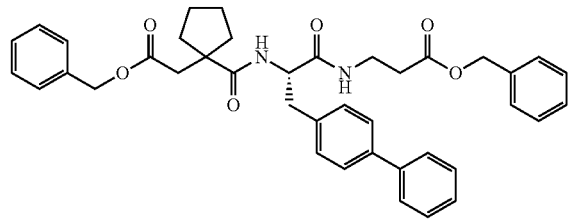

Pd on carbon, H₂ gas, EtOH

| Example # | HPLC-RT (condition) | MS (M + 1) |
|---|---|---|
| Example 1-2 | 1.66 min. (D) | 493.3 |
| Example 1-3 | 1.35 min. (B) | 449.2 |
| Example 1-4 | 1.65 min. (B) | 521.2 |
| Example 1-5 | 1.64 min. (B) | 424.0 |
| Example 1-6 | 1.36 min. (B) | 521.1 |
| Example 1-7 | 1.06 min. (B) | 306.1 |
| Example 1-8 | 0.58 min. (B) | 417.0 |
| Example 1-9 | 1.21 min. (B) | 507.3 |
| Example 1-10 | 1.33 min. (A) | 410.3 |
| Example 1-11 | 1.49 min. (A) | 410.1 |
| Example 1-12 | 0.94 min. (H) | 467.3 |

Example 1-2

¹H NMR (400 MHz, DMSO-d6, mixture of rotamers) δ ppm 1.24-1.51 (m, 6H) 1.67-2.24 (m, 6H) 2.48-2.68 (m, 2H) 2.84-3.03 (m, 2H) 3.26-3.43 (m, 1.5H) 3.59-3.73 (m, 0.5H) 4.13-4.16 (m, 0.5H) 4.53-4.58 (m, 0.5H) 4.82-4.89 (m, 1H) 7.27-7.36 (m, 3H) 7.42-7.47 (m, 2H) 7.50 (d, J=8.1 Hz, 1H) 7.53-7.56 (m, 1.5H) 7.60-7.64 (m, 2H) 7.90 (d, J=8.6 Hz, 0.5H) 12.07 (br s, 2H); HRMS (ES+) m/z for C28H33N2O6 [M+H]+ calcd 493.2339. found 493.2330.

Example 1-3

¹H NMR (400 MHz, DMSO-d6) δ ppm 1.45-1.82 (m, 10H) 1.90-2.07 (m, 2H) 2.59 (s, 2H) 2.87-3.01 (m, 2H) 3.14-3.31 (m, 3H) 3.46-3.52 (m, 1H) 4.69-4.74 (m, 1H) 7.30-7.36 (m, 3H) 7.43-7.46 (m, 2H) 7.54 (d, J=8.1 Hz, 2H), 7.61-7.63 (m, 2H) 7.67 (d, J=8.1 Hz, 1H) 11.90 (br s, 1H); HRMS (ES+) m/z for C27H33N2O4 [M+H]+ calcd 449.2440. found 449.2437.

Example 1-4

¹H NMR (400 MHz, DMSO-d6, mixture of rotamers) δ ppm 1.00-1.13 (m, 3H) 1.24-1.53 (m, 6H) 1.73-2.21 (m, 6H) 2.49-3.03 (m, 4H) 3.32-4.28 (m, 5H) 4.48-4.92 (m, 1H) 7.26-8.23 (m, 10H); HRMS (ES+) m/z for C30H36N2NaO6 [M+Na]+ calcd 543.24711. found 543.2466.

Example 1-5

¹H NMR (400 MHz, CDCl₃, data for major rotamer) δ ppm 1.20 (t, J=7.1 Hz, 3H) 1.52-1.66 (m, 6H) 1.91-2.00 (m, 2H) 2.57 (A of AB, J=16.5 Hz, 1H) 2.70 (B of AB, J=16.5 Hz, 1H) 3.17-3.36 (m, 2H) 4.07 (q, J=7.1 Hz, 2H) 4.81-4.86 (m, 1H) 6.66 (br d, J=7.0 Hz, 1H) 7.29-7.37 (m, 3H) 7.42-7.46 (m, 2H) 7.54-7.58 (m, 4H); HRMS (ES+) m/z for C25H29NO5Na [M+Na]+ calcd 446.19434. found 446.1940.

Example 1-6

¹H NMR (400 MHz, DMSO-d6, mixture of rotamers) δ ppm 1.13-1.19 (m, 3H) 1.42-1.49 (m, 6H) 1.78-1.94 (m, 5H) 2.14-2.23 (m, 1H) 2.58 (s, 2H for major rotamer) 2.90-3.02 (m, 2H) 3.53-3.57 (m, 1H) 3.67-3.73 (m, 1H) 4.05-4.10 (m, 2H) 4.28-4.31 (m, 1H) 4.60-4.78 (m, 1H) 7.27-7.69 (m, 10H) 11.90 (br s, 1H); HRMS (ES+) m/z for C30H37N2O6 [M+H]+ calcd 521.2652. found 521.2646.

Example 1-7

¹H NMR (400 MHz, DMSO-d6, mixture of rotamers) δ ppm 1.42-1.50 (m, 6H) 1.89-2.03 (m, 2H) 2.40-2.63 (m, 2H) 2.84-3.12 (m, 2H) 4.41-4.47 (m, 1H) 7.30-7.36 (m, 3H) 7.43-7.47 (m, 2H) 7.54-7.58 (m, 2H) 7.62-8.15 (m, 3H); HRMS (ES+) m/z for C23H26NO3 [M+H]+ calcd 396.1811. found 396.1804.

Example 1-8

¹H NMR (400 MHz, DMSO-d6, mixture of rotamers) δ ppm 1.35-1.54 (m, 6H) 1.79-1.95 (m, 5H) 2.11-2.19 (m, 1H) 2.50-2.60 (m, 2H) 2.84-2.98 (m, 2H) 3.46-3.51 (m, 1H) 3.64-3.70 (m, 1H) 3.84-4.24 (m, 1H) 4.56-4.74 (m, 1H) 7.15-7.64 (m, 6H) 12.18 (br s, 2H); HRMS (ES+) m/z for C22H29N2O6 [M+H]+ calcd 417.2026. found 417.2020.

Example 1-9

¹H NMR (400 MHz, CDCl₃, mixture of rotamers) δ ppm 1.39-1.65 (m, 6H) 1.86-2.07 (m, 4H) 2.15-2.40 (m, 3H) 2.49-2.97 (m, 4H) 3.06-3.18 (m, 1H) 3.27-3.71 (m, 2H) 4.14-4.58 (m, 2H) 7.23-7.71 (m, 10H); HRMS (ES+) m/z for C29H35N2O6 [M+H]+ calcd 507.2495. found 507.2490.

Example 1-10

¹H NMR (400 MHz, DMSO-d6) δ ppm 1.57-1.59 (m, 6H) 1.96-2.09 (m, 2H) 2.14-2.38 (m, 2H) 2.63-2.99 (m, 5H) 7.22-7.65 (m, 10H) 12.01 (br s, 2H); HRMS (ES+) m/z for C24H28NO5 [M+H]+ calcd 410.1968. found 410.1961.

Example 1-11

¹H NMR (400 MHz, CDCl₃, mixture of rotamers) δ ppm 1.26-2.12 (m, 8H) 2.58-2.78 (m, 2H) 2.80-2.88 (m, 1H) 3.06-3.13 (m, 2H) 3.28-3.36 (m, 1H) 3.54-3.59 (m, 1H) 6.48-6.51 (app t, 1H) 7.26-7.57 (m, 9H); HRMS (ES+) m/z for C24H28NO5 [M+H]+ calcd 410.1968. found 410.1960.

Example 1-12

HRMS (ES+) m/z for C26H31N2O6 [M+H]+ calcd 467.2182. found 467.2180.

Example 2-1

Synthesis of (R)-3-(biphenyl-4-yl)-2-(1-(carboxymethyl)cyclopentanecarboxamido)propanoic acid

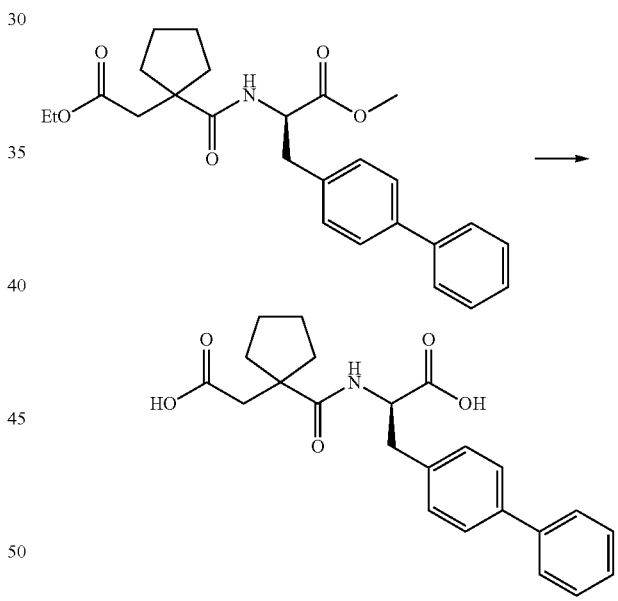

To a solution of (R)-methyl 3-(biphenyl-4-yl)-2-(1-(2-ethoxy-2-oxoethyl)cyclopentanecarboxamido)propanoate (135.5 mg, 0.310 mmol) in toluene (3.1 ml), bis(tributyltin) oxide (1.578 ml, 3.10 mmol) was added at room temperature under nitrogen. The reaction mixture was allowed to stir at 90° C. for 15 hr and then 100° C. for 26 hr. The reaction mixture was cooled to room temperature, 10% KFaq (2 ml) was added. The suspension was vigorously stirred for 1 hr, the solution was filtered, and the organic layer and the aqueous layer were separated. To the aqueous layer, 10% citric acid aq was added. The aqueous layer was extracted with EtOAc. The combined organic layer was washed with brine. The organic layer was dried over MgSO₄, filtered and concentrated under reduced pressure. The obtained residue was purified by RP-HPLC (SunFire C18, H₂O (0.1% TFA)/CH₃CN), and the obtained product was treated with 1M LiOH (0.5 ml) in THF (0.5 ml) and MeOH (0.1 ml) for 17 hr. The reaction mixture was acidified with 1M HCl to pH 3. The product was extracted with EtOAc, dried over $Na_2SO_4$, filtered, and concentrated under reduced pressure. The obtained residue was purified twice by RP-HPLC (SunFire C18, $H_2O$ (0.1% TFA)/$CH_3CN$) and then solidified in DCM/heptane to give (R)-3-(biphenyl-4-yl)-2-(1-(carboxymethyl)cyclopentanecarboxamido)propanoic acid (12.4 mg); Retention time=1.63 minutes (condition A); MS (m+1)=396.0; $^1$H NMR (400 MHz, DMSO-d6, mixture of rotamers) δ ppm 1.45-1.50 (m, 6H) 1.95-2.00 (m, 2H) 2.39-2.62 (m, 2H) 2.84-3.12 (m, 2H) 4.40-4.46 (m, 1H) 7.30-8.15 (m, 10H) 12.25 (br s, 2H); HRMS (ES+) m/z for C23H25NNaO5 [M+Na]+ calcd 418.16304. found 418.1632.

Example 3-1

Synthesis of 3-(1-(carboxymethyl)cyclopentanecarboxamido)-2-(3,5-dichlorobenzyl)propanoic acid To a solution of tert-butyl 3-(1-(2-(benzyloxy)-2-oxoethyl)cyclopentanecarboxamido)-2-(3,5-dichlorobenzyl)propanoate (130 mg, 0.237 mmol) in TFA (1.5 ml), pentamethylbenzene (351 mg, 2.370 mmol) was added at room temperature. After stirred for 2 hr, the reaction mixture was concentrated under reduced pressure. The obtained crude material was hydrogenated under hydrogen atmosphere (1 atm) with Pd/C in EtOAc for 0.5 hr at room temperature. The reaction mixture was filtered, and the filtered cake was washed with MeOH. The combined filtrate was concentrated under reduced pressure. The obtained residue was purified by RP-HPLC (SunFire, H2O (0.1% TFA)/$CH_3CN$) to give 341-(carboxymethyl)cyclopentanecarboxamido)-2-(3,5-dichlorobenzyl)propanoic acid (62.5 mg); Retention time=0.71 minutes (condition B); MS (m+1)=402.0; $^1$H NMR (400 MHz, DMSO-6, mixture of rotamers) δ ppm 1.47-1.58 (m, 6H) 1.95-2.05 (m, 2H) 2.54-2.63 (m, 2H) 2.68-2.85 (m, 3H) 3.13-3.29 (m, 2H) 7.24 (d, J=1.8 Hz, 2H) 7.42-7.43 (m, 1H) 7.60-7.63 (m, 1H); HRMS (ES+) m/z for C18H22Cl2NO5 [M+H]+ calcd 402.0875. found 402.0854

Example 4-1

Synthesis of 3-(1-(carboxymethyl)cyclopentanecarboxamido)-2-(3,4-dichlorobenzyl)propanoic acid

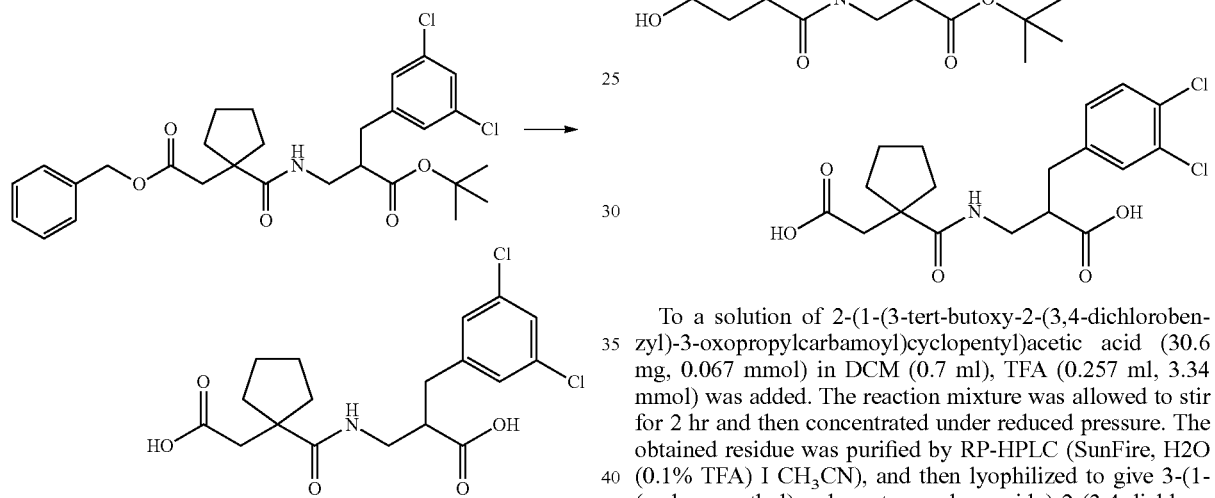

To a solution of 2-(1-(3-tert-butoxy-2-(3,4-dichlorobenzyl)-3-oxopropylcarbamoyl)cyclopentyl)acetic acid (30.6 mg, 0.067 mmol) in DCM (0.7 ml), TFA (0.257 ml, 3.34 mmol) was added. The reaction mixture was allowed to stir for 2 hr and then concentrated under reduced pressure. The obtained residue was purified by RP-HPLC (SunFire, H2O (0.1% TFA) I $CH_3CN$), and then lyophilized to give 3-(1-(carboxymethyl)cyclopentanecarboxamido)-2-(3,4-dichlorobenzyl)propanoic acid (10.5 mg); Retention time=0.67 minutes (condition B); MS (m+1)=402.0; $^1$H NMR (400 MHz, DMSO-d6, mixture of rotamers) δ ppm 1.47-1.58 (m, 6H) 1.97-2.04 (m, 2H) 2.54-2.63 (m, 2H) 2.68-2.84 (m, 3H) 3.13-3.28 (m, 2H) 7.17-7.19 (m, 1H) 7.43 (d, J=2.0 Hz, 1H) 7.52-7.54 (m, 1H) 7.61-7.63 (app t, 1H) 12.14 (br s, 2H); HRMS (ES+) m/z for C18H22Cl2NO5 [M+H]+ calcd 402.0875. found 402.0855.

Following compound was prepared using similar procedure as described in example 4-1:

| Example # | Product | Reagents | HPLC-RT (condition) | MS (M + 1) |
|---|---|---|---|---|
| Example 4-2 | 3-(1-(carboxymethyl)cyclopentanecarboxamido)-2-(4-methoxybenzyl)propanoic acid | TFA, DCM, rt | 1.18 min. (A) | 364.1 |

Example 4-2

¹H NMR (400 MHz, DMSO-d6, mixture of rotamers) δ ppm 1.47-1.58 (m, 6H) 1.97-2.04 (m, 2H) 2.51-2.78 (m, 5H) 3.10-3.26 (m, 2H) 3.71 (s, 3H) 6.80-6.83 (m, 2H) 7.06-7.10 (m, 2H) 7.56-7.59 (m, 1H) 12.03 (br s, 2H); HRMS (ES+) m/z for C38H50N2NaO12 [2M+Na]+ calcd 749.3262. found 749.3235.

Example 5-1

Synthesis of 2-(1-(3-tert-butoxy-2-(3,4-dichlorobenzyl)-3-oxopropylcarbamoyl)cyclopentyl)acetic acid

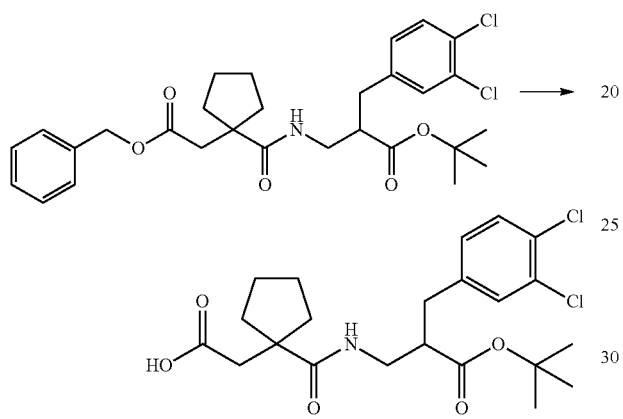

A suspension of tert-butyl 3-(1-(2-(benzyloxy)-2-oxoethyl)cyclopentanecarboxamido)-2-(3,4-dichlorobenzyl)propanoate (81.2 mg, 0.148 mmol) and Pd/C (31.5 mg, 0.015 mmol) in EtOH (1 ml) was allowed to stir under hydrogen atmosphere (1 atm) for 6.5 hr. The reaction mixture was filtered, and the filter cake was washed with MeOH. The combined filtrate was concentrated under reduced pressure. The obtained residue was purified by RP-HPLC (X-Bridge C18, H₂O (0.1% NH₄OH)/CH₃CN) to give 2-(1-(3-tert-butoxy-2-(3,4-dichlorobenzyl)-3-oxopropylcarbamoyl)cyclopentyl)acetic acid (30.6 mg); Retention time=1.30 minutes (condition B); MS (m+1)=458.2; ¹H NMR (400 MHz, CDCl₃, data for major rotamer) δ ppm 1.37 (s, 9H) 1.70-1.98 (m, 8H) 2.64-2.88 (m, 5H) 3.34-3.53 (m, 2H) 6.53-6.56 (m, 1H) 7.02-7.04 (m, 1H) 7.28 (d, J=2.0 Hz, 1H) 7.36 (d, J=8.0 Hz, 1H).

Following compound was prepared using similar procedure as described in example 5-1:

Example 5-2

¹H NMR (400 MHz, CDCl₃, data for major rotamer) δ ppm 1.39 (s, 9H) 1.71-1.92 (m, 8H) 2.63-2.90 (m, 5H) 3.33-3.50 (m, 2H) 3.79 (s, 3H) 6.58-6.60 (m, 1H) 6.81-6.85 (m, 2H) 7.07-7.10 (m, 2H).

Example 6-1

Synthesis of 3-(Biphenyl-4-ylmethyl)-4-(1-(carboxymethyl)cyclopentylamino)-4-oxobutanoic acid

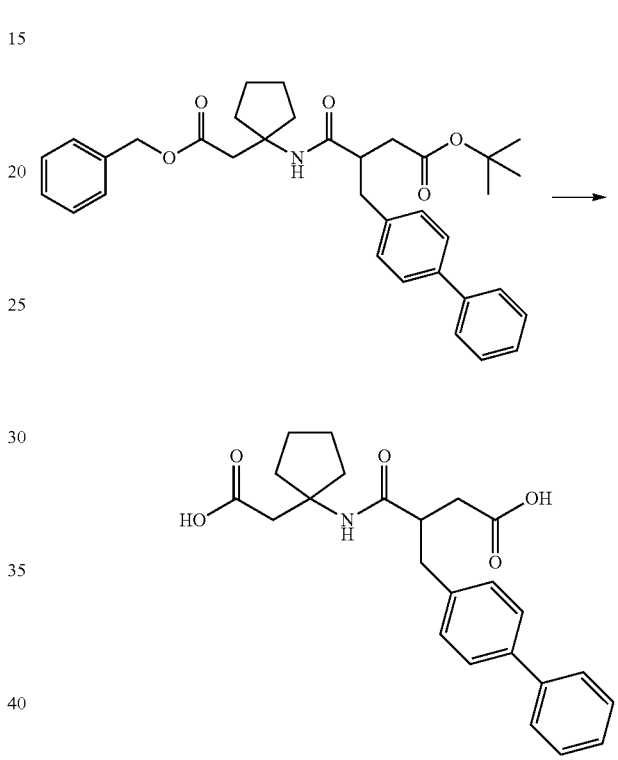

Tert-butyl 4-(1-(2-(benzyloxy)-2-oxoethyl)cyclopentylamino)-3-(biphenyl-4-ylmethyl)-4-oxobutanoate was dissolved in EtOAc (6 mL) and hydrogenated with 10% Pd/C at room temperature under hydrogen. After 2 hr, the reaction mixture was concentrated under reduced pressure. The obtained residue was dissolved in DCM, and to the mixture was added TFA. After stirred at room temperature for 1.5 hr,

| Example # | Product | Reagent | HPLC-RT (condition) | MS (M + 1) |
|---|---|---|---|---|
| Example 5-2 | 2-(1-(3-tert-butoxy-2-(4-methoxybenzyl)-3-oxopropylcarbamoyl)cyclopentyl)acetic acid | Pd/C, H2 gas, EtOH, rt | 1.11 min. (A) | 420.3 | the reaction mixture was concentrated under reduced pressure. The obtained residue was purified by reverse phase HPLC [40 to 75% ACN-water (0.1% TFA) over 10 min by Sunfire C18 column] to give the title compound (23 mg). LCMS (condition B): 410.1 (M+1); retention time=0.99 min. $^1$H NMR (400 MHz, DMSO-d$_6$) δ ppm 1.38-1.61 (m, 6H), 1.95-2.05 (m, 2H), 2.10 (dd, J=16.4, 5.8 Hz, 1H), 2.41-2.49 (m, 1H), 2.57 (dd, J=12.9, 7.1 Hz, 1H), 2.73 (dd, J=35.4, 14.7 Hz, 2H), 2.82-2.99 (m, 2H), 7.29 (d, J=8.1 Hz, 2H), 7.34 (t, J=7.3 Hz, 1H), 7.45 (t, J=7.7 Hz, 2H), 7.56 (d, J=8.3 Hz, 2H), 7.63 (d, J=7.1 Hz, 3H), 11.97 (br. s., 2H).

Example 7-1

Synthesis of 3-(1-(Carboxymethyl)cyclopentanecarboxamido)-2-(4-(pyridin-2-yl)benzyl)propanoic acid

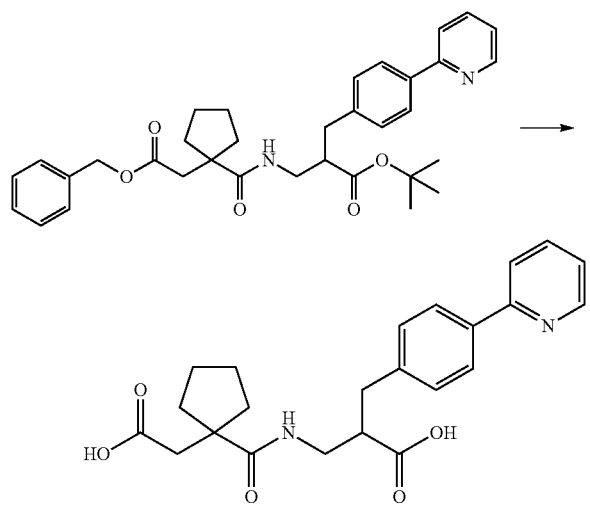

Tert-Butyl 3-(1-(2-(benzyloxy)-2-oxoethyl)cyclopentanecarboxamido)-2-(4-(pyridin-2-yl)benzyl)propanoate was dissolved in EtOAc (5 ml) and hydrogenated with 10% Pd/C under H$_2$ at room temperature. After 3 hours, the reaction mixture was filtered and concentrated under reduced pressure. To the obtained residue in DCM (1.00 ml) at room temperature was added TFA, and the reaction mixture was stirred at room temperature for 1 hr. The reaction mixture was concentrated under reduced pressure. The obtained residue was purified by reverse phase HPLC [5 to 35% ACN-water (0.1%/oTFA) over 10 min by X-bridge phenyl column] to give the title compound (48 mg). LCMS (condition A): 411.3 (M+1); retention time=1.24 min. $^1$H NMR (400 MHz, DMSO-d$_6$) δ ppm 1.44-1.62 (m, 6H), 1.96-2.06 (m, 2H), 2.59 (dd, J=18.7, 16.4 Hz, 2H), 2.74-2.91 (m, 3H), 3.14-3.24 (m, 1H), 3.24-3.33 (m, 1H), 7.34 (d, J=8.3 Hz, 2H), 7.47-7.53 (m, 1H), 7.68 (t, J=5.6 Hz, 1H), 7.96 (d, J=8.3 Hz, 2H), 8.03-8.11 (m, 2H), 8.68-8.74 (m, 1H).

Example 8-1

Synthesis of (S)-2-(1-(2-q-Chlorobiphenyl-4-yl)-1-(1H-tetrazol-5-yl)ethylcarbamoyl)cyclopentyl)acetic acid

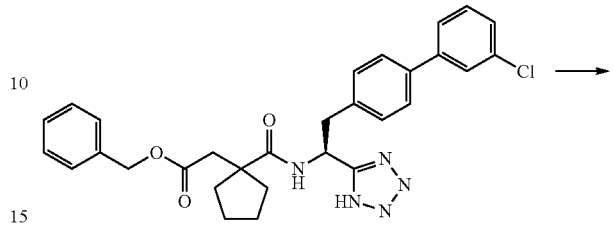

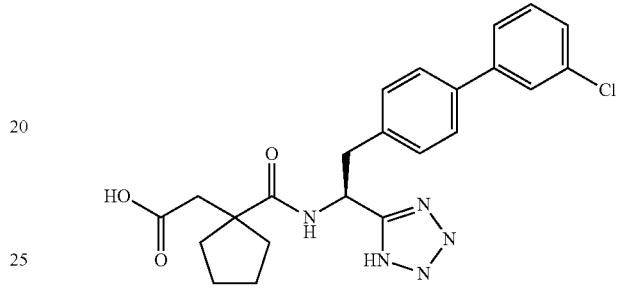

(S)-Benzyl 2-(1-(2-(3'-chlorobiphenyl-4-yl)-1-(1H-tetrazol-5-yl)ethylcarbamoyl)cyclopentyl)acetate was dissolved in EtOAc and hydrogenated at room temperature under H$_2$ with 10% Pd/C for 20 minutes. The reaction mixture was concentrated under reduced pressure, and the obtained residue was purified by reverse phase HPLC [35 to 100% ACN-water (0.1° ADTFA) over 10 min by Sunfire C18 column] to give the title compound: LCMS (condition B): 454.3 (M+1); retention time=0.95 min. $^1$H NMR (400 MHz, DMSO-d6) δ ppm 1.33-1.54 (m, 4H), 1.83-1.99 (m, 1H), 2.59 (s, 1H), 3.24-3.33 (m, 2H), 5.44 (dd, J=14.9, 8.3 Hz, 1H), 7.33 (d, J=8.1 Hz, 2H), 7.37-7.43 (m, 1H), 7.47 (t, J=7.8 Hz, 1H), 7.55-7.62 (m, 3H), 7.68 (t, J=1.8 Hz, 1H), 8.17 (d, J=8.1 Hz, 1H), 12.08 (br. s., 1H), 15.88 (br. s., 1H).

Example 9-1

Synthesis of (S)-2-(1-(2-(3'-methylbiphenyl-4-yl)-1-(1H-tetrazol-5-yl)ethylcarbamoyl)cyclopentyl)acetic acid

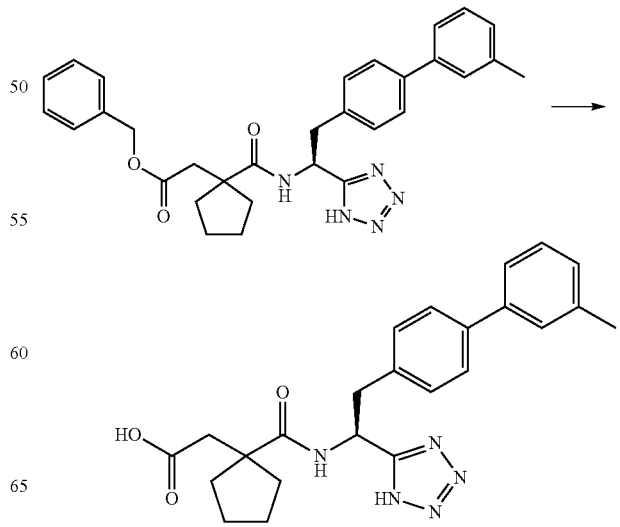

(S)-benzyl 2-(1-(2-(3'-methylbiphenyl-4-yl)-1-(1H-tetrazol-5-yl)ethylcarbamoyl)cyclopentyl)acetate (175 mg, 0.334 mmol) was hydrogenated with 5% Pd—C (35.6 mg) in MeOH at room temperature for 0.5 hours. The reaction mixture was filtered through celite pad, and the filtrate was concentrated under reduced pressure. The residue was purified by reverse phase HPLC (Waters SunFire C-18 column, 0.1% TFA in H$_2$O/CH$_3$CN) to give (S)-2-(1-(2-(3'-methylbiphenyl-4-yl)-1-(1H-tetrazol-5-yl)ethylcarbamoyl)cyclopentyl) acetic acid. Retention time=0.76 minutes (condition B); MS (m+1)=434; $^1$H NMR (400 MHz, DMSO-d6) δ ppm 1.33-1.54 (m, 6H), 1.87-2.01 (m, 2H), 2.36 (s, 3H), 2.59 (s, 2H), 3.22-3.77 (m, 2H), 5.43 (dd, J=8.34, 14.91 Hz, 1H), 7.15 (d, J=7.33 Hz, 1H), 7.27-7.35 (m, 3H), 7.38-7.45 (m, 2H), 7.53 (d, J=8.08 Hz, 2H), 8.16 (d, J=7.83 Hz, 1H); HRMS (ES+) m/z for C24H27N5O3 [M+H]+ calcd 433.2. found 433.2

Following compounds were prepared using similar procedure as described in example 9-1:

| Example # | Product | Reactant | HPLC-RT (condition) | MS (M + 1) |
|---|---|---|---|---|
| Example 9-2 | 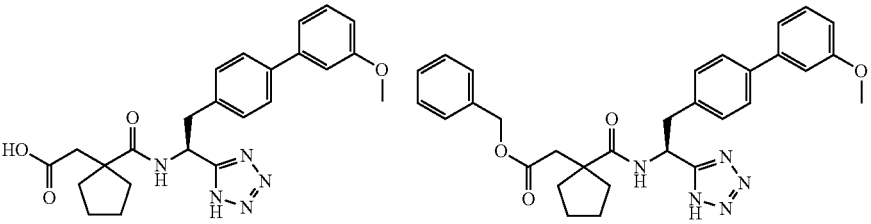<br>{1-[(S)-2-(3'-Methoxy-biphenyl-4-yl)-1-(1H-tetrazol-5-yl)-ethylcarbamoyl]-cyclopentyl}-acetic acid | 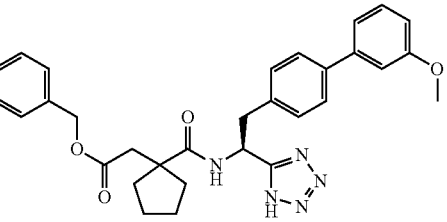 | 1.26 min. (A) | 450 |
| Example 9-3 | 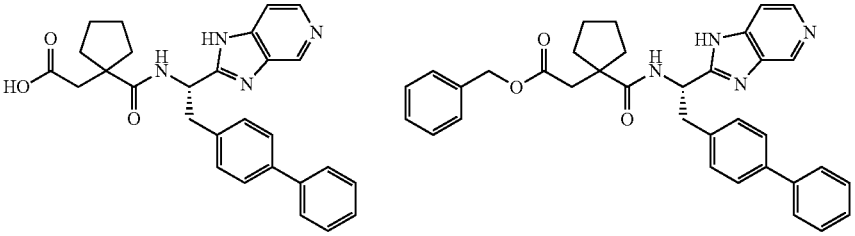<br>(S)-2-(1-(2-(biphenyl-4-yl)-1-(1H-imidazo[4,5-c]pyridin-2-yl)ethylcarbamoyl)cyclopentyl)acetic acid | 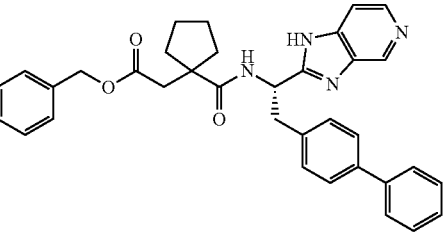 [SMILES: O=C(CC1(C(=O)N[C@@H](Cc2ccc(-c3ccccc3)cc2)c2nc3cnccc3[nH]2)CCCC1)OCc1ccccc1] | 1.14 min. (B) | 469 |

Example 9-2

$^1$H NMR (400 MHz, DMSO-d6) δ ppm 1.36-1.54 (m, 6H), 1.85-2.01 (m, 2H), 2.59 (s, 2H), 3.22-3.35 (m, 2H), 3.81 (s, 3H), 5.43 (dd, J=8.34, 14.91 Hz, 1H), 6.89-6.94 (m, 1H), 7.13 (t, J=1.77 Hz, 1H), 7.18 (d, J=8.34 Hz, 1H), 7.30 (d, J=8.34 Hz, 2H), 7.36 (1, J=8.08 Hz, 1H), 7.55 (d, J=8.34 Hz, 2H), 8.16 (d, J=7.83 Hz, 1H); HRMS (ES+) m/z for C24H27N5O4 [M+H]+ calcd 449.2. found 449.2.

Example 9-3

$^1$H NMR (400 MHz, DMSO-d6) δ ppm 1.35-1.56 (m, 6H), 1.87-2.00 (m, 2H), 2.61 (s, 2H), 3.29-3.64 (m, 2H), 5.42-5.50 (m, 1H), 7.31-7.39 (m, 3H), 7.45 (t, J=7.83 Hz, 2H), 7.56 (d, J=8.34 Hz, 2H), 7.59-7.64 (m, 2H), 8.06 (bd, J=6.57 Hz, 1H), 8.23 (d, J=7.83 Hz, 1H), 8.56 (d, J=6.57 Hz, 1H), 9.38 (bs, 1H); HRMS (ES+) m/z for C28H28N4O3 [M+H]+ calcd 468.2. found 468.2.

Example 10-1

Synthesis of (S)-1-((S)-3-(Biphenyl-4-yl)-2-(2-(carboxymethyl)-2,3-dihydro-1H-indene-2-carboxamido)propanoyl)pyrrolidine-2-carboxylic acid

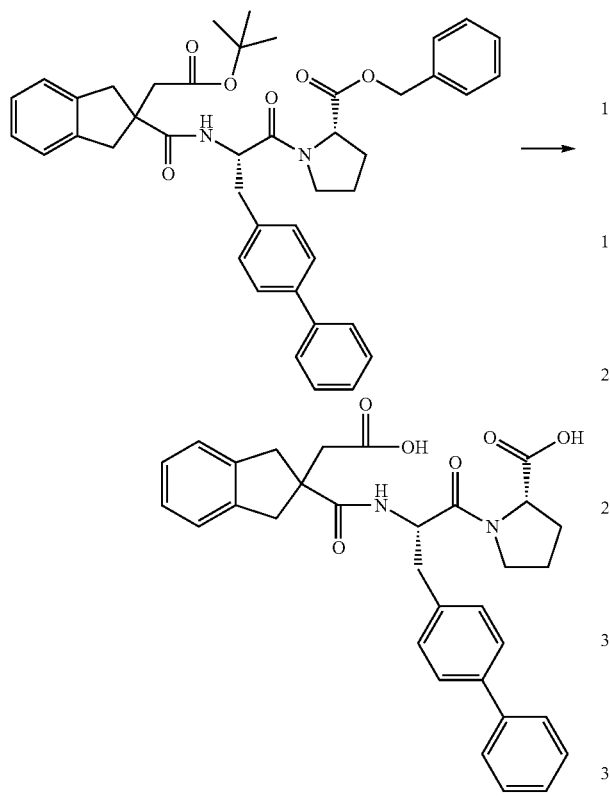

A solution of (S)-benzyl 14(S)-3-(biphenyl-4-yl)-2-(2-(2-tert-butoxy-2-oxoethyl)-2,3-dihydro-1H-indene-2-carboxamido) propanoyl)pyrrolidine-2-carboxylate (98 mg, 0.143 mmol) in EtOAc (10 ml) at room temperature was hydrogenated with 10% Pd/C for 1 hr. The mixture was filtered and concentrated under reduced pressure. To the obtained residue was added TFA (0.452 ml, 5.87 mmol) in DCM. After stirred for 2.5 hr, the reaction mixture was concentrated under reduced pressure. The obtained residue was purified by reverse phase HPLC [40 to 70% ACN-water (0.1% TFA) over 10 min by Sunfire C18 column] to give the title compound. LCMS (condition B): 541.2 (M+1); retention time=1.30 min.

Example 11-1

Synthesis of (S)-1-((S)-2-(2-(carboxymethyl)-2,3-dihydro-1H-indene-2-carboxamido)-3-phenylpropanoyl)pyrrolidine-2-carboxylic acid

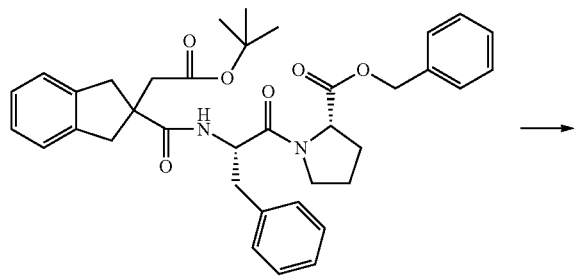

-continued

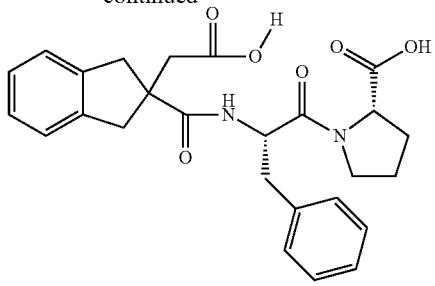

(S)-Benzyl 14(S)-2-(2-(2-tert-butoxy-2-oxoethyl)-2,3-dihydro-1H-indene-2-carboxamido)-3-phenylpropanoyl)pyrrolidine-2-carboxylate in EtOAc at room temperature was hydrogenated with 10% Pd/C for 1 hr. The mixture was filtered and concentrated under reduced pressure. To the obtained residue in DCM was added 1 mL TFA, and stirred for 1 hr. The reaction mixture was concentrated under reduced pressure, and the obtained residue was purified by reverse phase HPLC [30 to 80% ACN-water (0.1% TFA) over 10 min by Sunfire C18 column] to give the title compound. LCMS (condition A): 465.2 (M+1); retention time=1.29 min. $^1$H NMR (400 MHz, DMSO-d$_6$) δ ppm 1.76-1.96 (m, 3H), 2.04-2.20 (m, 1H), 2.56-2.75 (m, 2H), 2.78-3.00 (m, 4H), 3.17-3.36 (m, 2H), 3.40-3.53 (m, 1H), 3.57-3.68 (m, 1H), 4.22 (dd, J=8.7, 4.7 Hz, 1H), 4.63-4.75 (m, 1H), 7.06-7.29 (m, 9H), 7.83 (d, J=8.1 Hz, 1H), 12.23 (br. s., 2H).

Example 12-1

Synthesis of (S)-2-(1-(3-(biphenyl-4-yl)-1-(dimethylamino)-1-oxopropan-2-ylcarbamoyl)cyclopentyl) acetic acid

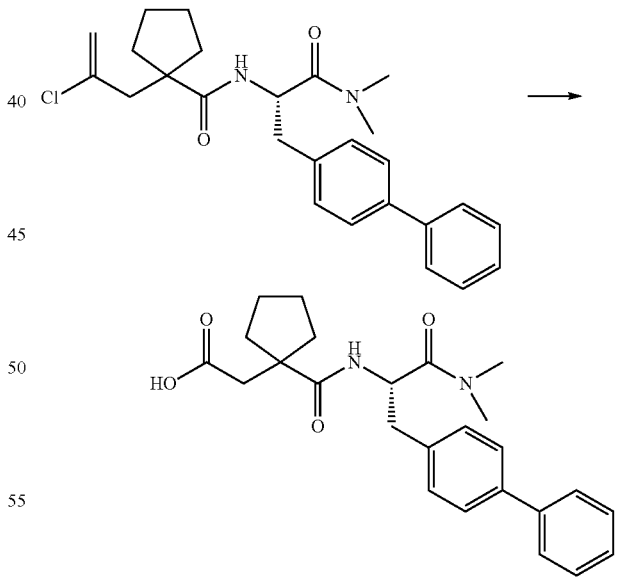

To a solution of (S)—N-(3-(biphenyl-4-yl)-1-(dimethylamino)-1-oxopropan-2-yl)-1-(2-chloroallyl)cyclopentanecarboxamide (78 mg, 0.18 mmol) in acetone (5 mL) at −78° C. was bubbled ozone for 1 minutes with a persistent pale blue color. The mixture was stirred at −78° C. for 5 minutes. To the mixture was bubbled oxygen for 10 minutes then added dimethyl sulfide (0.5 mL) followed by 1 mL of water. The mixture was stirred for 1 hr at room temperature and concentrated under reduced pressure. The obtained mixture was diluted in EtOAc and acidified with 1 M HCl. The organic layer was washed with water, brine, dried over MgSO₄, filtered and concentrated under reduced pressure. The obtained residue was purified by RP-HPLC (SunFire C18, H₂O (0.1% TFA)/ CH₃CN) to give (S)-2-(1-(3-(biphenyl-4-yl)-1-(dimethylamino)-1-oxopropan-2-ylcarbamoyl)cyclopentyl)acetic acid (62 mg). HPLC retention time=1.54 minutes (condition D); MS (m+1)=423.1; ¹H NMR (400 MHz, ACETONITRILE-d₃) δ ppm 1.50-1.76 (m, 6H), 1.86-2.09 (m, 2H), 2.63 (s, 2H), 2.89 (s, 3H), 2.96-3.01 (m, 1H), 2.99 (s, 3H), 3.10 (dd, 1H), 5.00-5.20 (m, 1H), 6.95 (br. s., 1H), 7.31 (d, J=8.1 Hz, 2H), 7.35-7.44 (m, 1H), 7.48 (t, J=7.6 Hz, 2H), 7.58 (d, J=8.3 Hz, 2H), 7.62-7.72 (m, 2H).

Example 13-1

Synthesis of (S)-2-(1-(3-(biphenyl-4-yl)-1-(methylamino)-1-oxopropan-2-ylcarbamoyl)cyclopentyl) acetic acid

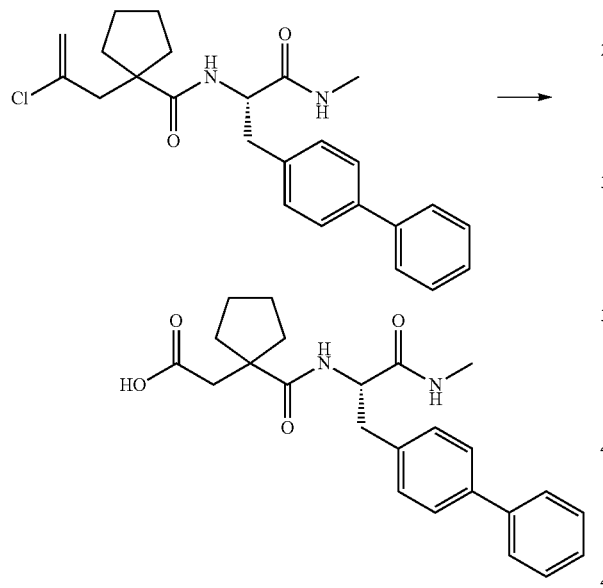

To a solution of (S)—N-(3-(biphenyl-4-yl)-1-(methylamino)-1-oxopropan-2-yl)-1-(2-chloroallyl)cyclopentanecarboxamide (38 mg, 0.09 mmol) in acetone (5 mL) at −78° C. was bubbled ozone for 1 minute with a persistent pale blue color. The mixture was stirred at −78° C. for 5 minutes. To the mixture was bubbled oxygen for 10 minutes then added dimethyl sulfide (0.5 mL) followed by 1 mL of water. The mixture was stirred for 1 hr at room temperature and concentrated under reduced pressure. The obtained mixture was diluted in EtOAc and acidified with 1 M HCl. The organic layer was washed with water, brine, dried over MgSO₄, filtered and concentrated under reduced pressure. The obtained residue was purified with RP-HPLC (SunFire C8, H₂O (0.1% TFA)/CH₃CN) to give (S)-2-(1-(3-(biphenyl-4-yl)-1-(methylamino)-1-oxopropan-2-ylcarbamoyl)cyclopentyl)acetic acid (27 mg). HPLC retention time=1.44 minutes (condition B); MS (m+1)=409.0; ¹H NMR (400 MHz, ACETONITRILE-d₃) δ ppm 1.33-1.63 (m, 6H), 1.72-1.94 (m, 2H), 2.60 (d, J=16.4 Hz, 1H), 2.73 (d, J=4.8 Hz, 3H), 2.73 (d, J=16.4 Hz, 1H), 2.97 (dd, J=14.1, 10.4 Hz, 1H), 3.39 (dd, J=14.1, 4.5 Hz, 1H), 4.58-4.76 (m, 1H), 6.70 (d, J=7.6 Hz, 1H), 7.09 (br. s., 1H), 7.34 (d, J=8.3 Hz, 2H), 7.38 (t, J=7.3 Hz, 1H), 7.43-7.51 (m, 2H), 7.59 (d, J=8.1 Hz, 2H), 7.62-7.67 (m, 2H).

Example 14-1

Synthesis of (S)-2-(1-(3-(biphenyl-4-yl)-1-((carboxymethyl)(methyl)amino)-1-oxopropan-2-ylcarbamoyl)cyclopentyl)acetic acid

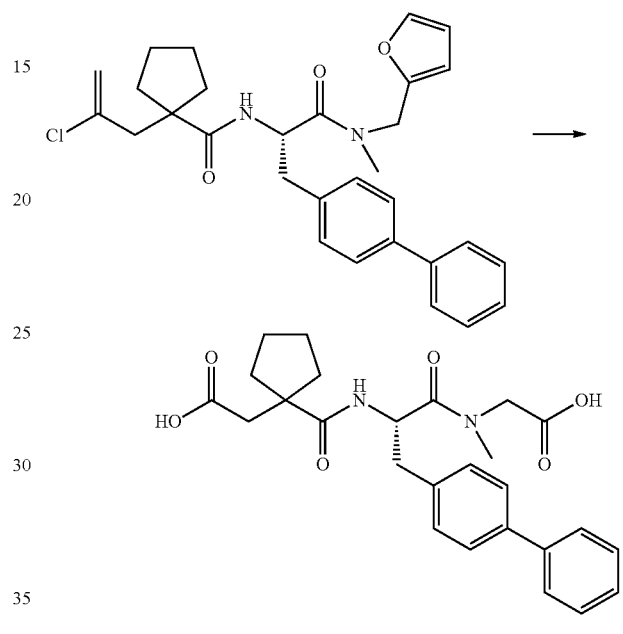

To a solution of (S)—N-(3-(biphenyl-4-yl)-1-((furan-2-ylmethyl)(methyl)amino)-1-oxopropan-2-yl)-1-(2-chloroallyl)cyclopentanecarboxamide (70 mg, 0.14 mmol) in acetone (10 ml) cooled in a dry ice acetone bath was bubbled ozone via ozone generator for 5 minutes. The crude mixture color was blue. The crude mixture was allowed to stir at −78° C. for 25 minutes. To the mixture was bubbled oxygen for 10 minutes and was added dimethyl sulfide (0.5 mL) followed by water (1 mL). The reaction mixture was removed from dry ice acetone bath and was warmed to room temperature for 2 hours. The mixture was concentrated under reduced pressure and was purified by RP-HPLC (SunFire C18, H₂O (0.1% TFA)/CH₃CN gradient) to give (S)-2-(1-(3-(biphenyl-4-yl)-1-((carboxymethyl)(methyl)amino)-1-oxopropan-2-ylcarbamoyl)cyclopentyl)acetic acid (14.1 mg). HPLC retention time=1.62 minutes (condition D); MS (m+1)=467.2. ¹H NMR (400 MHz, ACETONITRILE-d₃) δ ppm 1.51-1.64 (m, 12H), 1.72-1.90 (m, 4H), 2.93 (s, 3H, minor rotamer), 2.97-3.06 (m, 2H), 3.06-3.24 (m, 6H), 3.13 (s, 3H, major rotamer), 4.04 (d, J=17.2 Hz, 1H, major rotamer), 4.11 (d, J=18.7 Hz, 1H, minor rotamer), 4.14 (d, J=17.4 Hz, 1H, major rotamer), 4.33 (d, J=18.7 Hz, 1H, minor rotamer), 5.01 (td, J=8.0, 5.6 Hz, 1H, minor rotamer), 5.20 (td, J=7.8, 5.7 Hz, 1H, major rotamer), 6.87 (d, J=7.8 Hz, 1H, major rotamer), 6.94 (d, J=8.1 Hz, 1H, minor rotamer), 7.25-7.74 (m, 18H).

Following compounds was prepared using similar procedure as described in example 14-1:

Example 14-2 HRMS (ES+) m/z for C25H29N2O6 [M+H]+ calcd 453.2026. found 453.2025.

Example 15-1

Synthesis of (S)-2-(1-(2-(biphenyl-4-yl)-1-(1-methyl-1H-tetrazol-5-yl)ethylcarbamoyl)cyclopentyl)acetic acid and (S)-2-(1-(2-(biphenyl-4-yl)-1-(2-methyl-2H-tetrazol-5-yl)ethylcarbamoyl)cyclopentyl)acetic acid

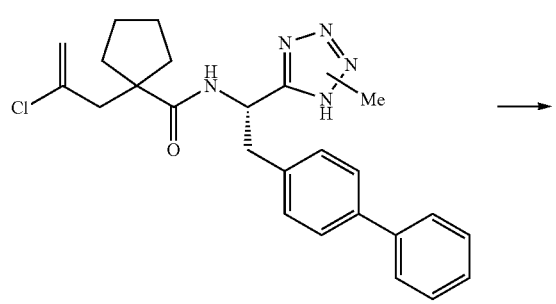

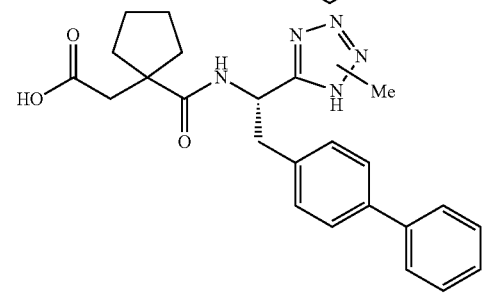

To a mixture of (S)—N-(2-(biphenyl-4-yl)-1-(1-methyl-1H-tetrazol-5-yl)ethyl)-1-(2-chloroallyl)cyclopentanecarboxamide and (S)—N-(2-(biphenyl-4-yl)-1-(2-methyl-2H-tetrazol-5-yl)ethyl)-1-(2-chloroallyl)cyclopentanecarboxamide in acetone at −7° C. was bubbled ozone for 30 seconds using ozone generator. The mixture became a persistent pale blue color. The mixture was stirred at −78° C. for 1 minute. To the mixture was bubbled oxygen gas for 10 minutes and was added dimethyl sulfide (0.5 mL) followed by water (1 mL). The cooling bath was removed and stirred for 1 hour at room temperature. The mixture was concentrated under reduced pressure and diluted in EtOAc. The mixture was acidified with 1 M HCl until pH=1. The organic layer was washed with water, brine, dried over MgSO₄, filtered and concentrated under reduced pressure. The obtained residue was purified by RP-HPLC (SunFire C18, H₂O (0.1% TFA)/CH₃CN gradient) to give two isomers, (S)-2-(1-(2-(biphenyl-4-yl)-1-(1-methyl-1H-tetrazol-5-yl)ethylcarbamoyl)cyclopentyl)acetic acid and (S)-2-(1-(2-(biphenyl-4-yl)-1-(2-methyl-2H-tetrazol-5-yl)ethylcarbamoyl)cyclopentyl)acetic acid (11 mg, regioisomer 1, 7.6 mg regioisomer 2). Regioisomer 1: HPLC retention time=1.57 minutes (condition D); MS (m+1)=434.1. ¹H NMR (400 MHz, CHLOROFORM-d) δ ppm 1.57-1.85 (m, 6H), 1.89-2.19 (m, 2H), 2.73 (q, J=16.4 Hz, 2H), 3.18-3.41 (m, 1H), 3.48 (dd, J=13.3, 6.4 Hz, 1H), 3.69 (s, 3H), 5.42-5.65 (m, 1H), 7.03 (br. s., 1H), 7.08-7.24 (m, 2H), 7.34-7.41 (m, 1H), 7.42-7.65 (m, 6H). Regioisomer 2: HPLC retention time=1.66 minutes (condition D); MS (m+1)=434.3. ¹H NMR (400 MHz, CHLOROFORM-d) δ ppm 1.44-1.73 (m, 6H), 1.73-1.99 (m, 2H), 2.59 (s, 2H), 3.15-3.38 (m, 2H), 4.24 (s, 3H), 5.50-5.79 (m, 1H), 6.60 (br. s., 1H), 7.06 (d, J=8.1 Hz, 2H), 7.19 (s, 2H), 7.22-7.30 (m, 1H), 7.30-7.56 (m, 4H).

Example 16-1

Synthesis of (S)-benzyl 1-((S)-2-(1-(2-(benzyloxy)-2-oxoethyl)cyclopentanecarboxamido)-3-(biphenyl-4-yl)propanoyl)pyrrolidine-2-carboxylate

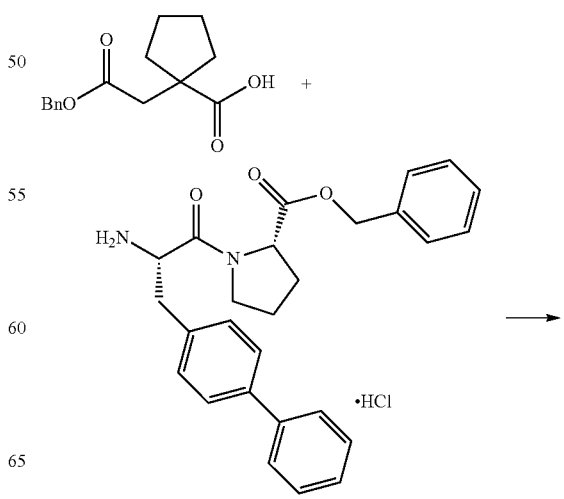

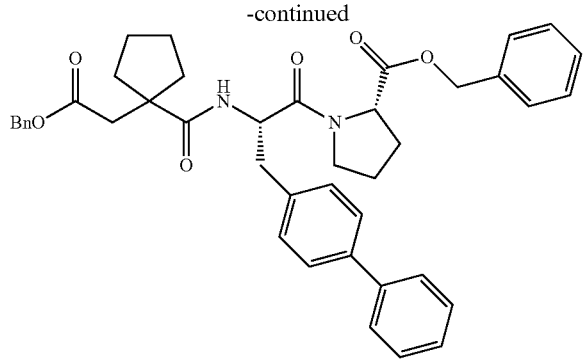

To a suspension of 1-(2-(benzyloxy)-2-oxoethyl)cyclopentanecarboxylic acid (177 mg, 0.674 mmol), (S)-benzyl 1-((S)-2-amino-3-(biphenyl-4-yl)propanoyl)pyrrolidine-2-carboxylate hydrochloride (396 mg, 0.809 mmol), EDCl (194 mg, 1.011 mmol) and 1-hydroxy-7-azabenzotriazole (138 mg, 1.011 mmol) in DMF (3.5 ml), DIPEA (0.177 ml, 1.011 mmol) was added under nitrogen at room temperature. After stirred for 1.5 hour, the reaction was quenched with $H_2O$. The products were extracted with EtOAc, washed with brine, dried over MgSO4, filtered, and concentrated under reduced pressure. The obtained residue was purified by flash column chromatography on silica gel (eluent: heptane/EtOAc=100:0 to 0:100) to give (S)-benzyl 14(S)-2-(1-(2-(benzyloxy)-2-oxoethyl)cyclopentanecarboxamido)-3-(biphenyl-4-yl)propanoyl)pyrrolidine-2-carboxylate (445 mg); Retention time=1.86 minutes (condition B); MS (m+1)=673.4; $^1H$ NMR (400 MHz, $CDCl_3$, mixture of rotamers) δ ppm 1.43-2.20 (m, 12H) 2.62-3.64 (m, 6H) 4.52-5.28 (m, 6H) 6.67-6.74 (m, 1H) 7.27-7.56 (m, 19H).

Following compounds were prepared using similar procedure as described in example 16-1:

| Example # | Product | | Condition | HPLC-RT (condition) | MS (M + 1) |
|---|---|---|---|---|---|
| Example 16-2 | (R)-benzyl 1-((S)-2-(1-(2-(benzyloxy)-2-oxoethyl)cyclopentanecarboxamido)-3-(biphenyl-4-yl)propanoyl)pyrrolidine-2-carboxylate | | EDCl, HOAt, DIPEA, DMF, rt | 1.86 min. (B) | 673.2 |
| Example 16-3 | (S)-benzyl 2-(1-(3-(biphenyl-4-yl)-1-oxo-1-(pyrrolidin-1-yl)propan-2-ylcarbamoyl)cyclopentyl)acetate | | EDCl, HOAt, DIPEA, DMF, rt | 1.70 min. (B) | 539.2 |
| Example 16-4 | (S)-ethyl 1-((S)-2-(1-(2-(benzyloxy)-2-oxoethyl)cyclopentanecarboxamido)-3-(biphenyl-4-yl)propanoyl)pyrrolidine-2-carboxylate | | EDCl, HOAt, DIPEA, DMF, rt | 1.75 min. (B) | 611.4 |

-continued

| Example # | Product | Condition | HPLC-RT (condition) | MS (M + 1) |
|---|---|---|---|---|
| Example 16-5 | (S)-benzyl 2-(1-(2-(benzyloxy)-2-oxoethyl)cyclopentanecarboxamido)-3-(biphenyl-4-yl)propanoate | EDCl, HOAt, DIPEA, DMF, rt | 1.86 min. (B) | 576.2 |
| Example 16-6 | (S)-benzyl 1-((S)-2-(1-(2-(benzyloxy)-2-oxoethyl)cyclopentanecarboxamido)-3-(phenylpropanoyl)pyrrolidine-2-carboxylate | EDCl, HOAt, DIPEA, DMF, rt | 1.70 min. (B) | 597.2 |
| Example 16-7 | (S)-benzyl 1-((S)-3-(1-(2-(benzyloxy)-2-oxoethyl)cyclopentanecarboxamido)-4-(biphenyl-4-yl)butanoyl)pyrrolidine-2-carboxylate | EDCl, HOAt, DIPEA, DMF, rt | 1.85 min. (B) | 687.4 |

Example 16-2

$^1$H NMR (400 MHz, CDCl$_3$, mixture of rotamers) δ ppm 1.46-2.28 (m, 12H) 2.50-3.11 (m, 5H) 3.49-3.78 (m, 1H) 4.38-5.17 (m, 6H) 6.41-6.65 (m, 1H) 7.12-7.56 (m, 19H).

Example 16-3

$^1$H NMR (400 MHz, CDCl$_3$) δ ppm 1.49-2.10 (m, 12H) 2.59-2.65 (m, 1H) 2.73 (A of AB, J=16.2 Hz, 1H) 2.75 (B of AB, J=16.2 Hz, 1H) 2.92-3.09 (m, 2H) 3.30-3.45 (m, 3H) 4.87-4.92 (m, 1H) 5.09 (s, 2H) 6.75 (br d, J=7.8 Hz, 1H) 7.26-7.35 (m, 8H) 7.40-7.44 (m, 2H) 7.48-7.50 (m, 2H) 7.55-7.57 (m, 2H).

Example 16-4

$^1$H NMR (400 MHz, CDCl$_3$, mixture of rotamers) δ ppm 1.18-1.32 (m, 3H) 1.43-2.20 (m, 12H) 2.62-2.87 (m, 2H) 3.00-3.78 (m, 4H) 4.07-5.29 (m, 6H) 6.67-6.76 (m, 1H) 7.27-7.58 (m, 14H).

Example 16-5

$^1$H NMR (400 MHz, CDCl$_3$, mixture of rotamers) δ ppm 1.58-1.78 (m, 6H) 2.01-2.24 (m, 2H) 2.58-2.77 (m, 2H) 3.03-3.17 (m, 2H) 4.87-4.94 (m, 1H) 5.06-5.24 (m, 4H) 6.22-6.51 (m, 1H) 7.03-7.55 (m, 19H).

Example 16-6

$^1$H NMR (400 MHz, CDCl$_3$, mixture of rotamers) δ ppm 1.61-2.19 (m, 12H) 2.63-2.84 (m, 2H) 2.93-3.57 (m, 4H) 4.49-5.24 (m, 6H) 6.63-6.71 (m, 1H) 7.19-7.37 (m, 15H).

Example 16-7

$^1$H NMR (400 MHz, CDCl$_3$, mixture of rotamers) δ ppm 1.57-2.44 (m, 15H) 2.65-3.07 (m, 4H) 3.25-4.59 (m, 4H) 5.07-5.29 (m, 4H) 7.19-7.61 (m, 19H).

Example 17-1

Synthesis of (S)-benzyl 1-((S)-3-(bi phenyl-4-yl)-2-(1-(2-ethoxy-2-oxoethyl)cyclopentanecarboxamido)propanoyl)pyrrolidine-2-carboxylate

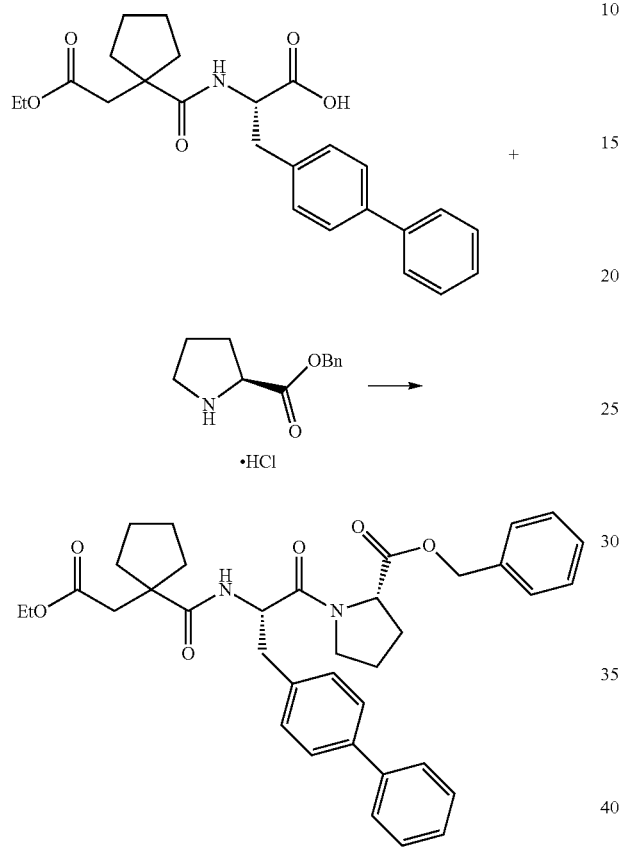

A solution of (S)-3-(biphenyl-4-yl)-2-(1-(2-ethoxy-2-oxoethyl)cyclopentanecarboxamido)propanoic acid (201.7 mg, 0.476 mmol), (S)-benzyl pyrrolidine-2-carboxylate hydrochloride (138 mg, 0.572 mmol), WSC.HCl (137 mg, 0.714 mmol), DIPEA (0.125 ml, 0.714 mmol) and 1-hydroxy-7-azabenzotriazole (97 mg, 0.714 mmol) in DMF (2 ml) was allowed to stir at room temperature under nitrogen for 14 hours. The reaction was quenched with H2O. The products were extracted with EtOAc. The organic layer was washed with NH4Claq, 0.1 M HCl (twice) and then brine, dried over MgSO4, filtered, and concentrated under reduced pressure. The obtained residue was purified by flash column chromatography on silica gel (heptane/EtOAc=100:0 to 0:100) to give (S)-benzyl 1-((S)-3-(biphenyl-4-yl)-2-(1-(2-ethoxy-2-oxoethyl)cyclopentanecarboxamido)propanoyl)pyrrolidine-2-carboxylate (243 mg); Retention time=1.74 minutes (condition B); MS (m+1)=611.2; $^1$H NMR (400 MHz, CD$_3$CN, mixture of rotamers) δ ppm 0.91-1.06 (m, 3H) 1.33-1.42 (m, 6H) 1.55-2.09 (m, 6H) 2.25-2.42 (m, 2H) 2.57-2.93 (m, 2H) 3.06-3.59 (m, 2H) 3.75-3.91 (m, 2H) 4.14-4.61 (m, 2H) 4.68-5.09 (m, 3H) 6.40-6.52 (m, 1H) 7.00-7.45 (m, 14H).

Example 18-1

Synthesis of (S)-benzyl 3-(biphenyl-4-yl)-2-(1-(2-ethoxy-2-oxoethyl)cyclopentanecarboxamido)propanoate

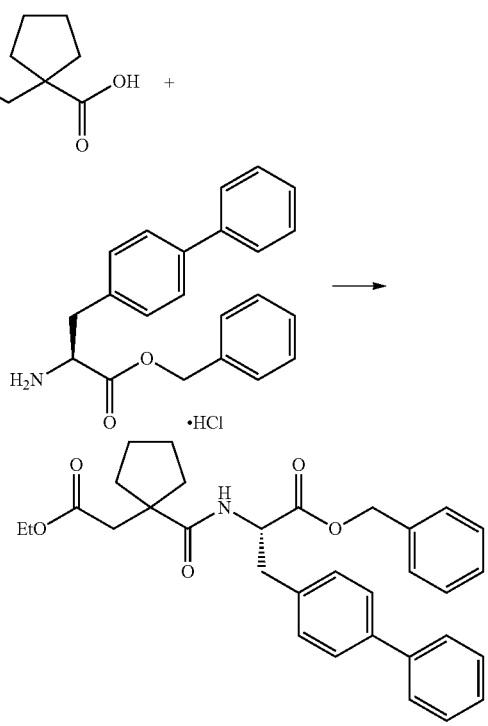

A solution of 1-(2-ethoxy-2-oxoethyl)cyclopentanecarboxylic acid (672 mg, 3.36 mmol), (S)-benzyl 2-amino-3-(biphenyl-4-yl)propanoate hydrochloride (957 mg, 2.60 mmol), WSC.HCl (833 mg, 4.34 mmol), 1-hydroxy-7-azabenzotriazole (591 mg, 4.34 mmol) and DIPEA (0.759 ml, 4.34 mmol) in DMF (15 ml) was allowed to stir at room temperature for 2 hours. The reaction was quenched with H$_2$O (10 ml) and 35% NH$_4$OH aqueous (2 ml). The mixture was stirred for 30 minutes. The product was extracted with EtOAc, washed twice with 1 M HCl aqueous, once with H$_2$O, and then once with brine. The organic layer was dried over MgSO$_4$, filtered, and concentrated under reduced pressure. The obtained residue was purified by flash column chromatography on silica gel (heptane/EtOAc=100:0 to 60:40) to give (S)-benzyl 3-(biphenyl-4-yl)-2-(1-(2-ethoxy-2-oxoethyl)cyclopentanecarboxamido)propanoate (1.143 g).

Retention time=1.74 minutes (condition B); MS (m+1)= 514.3; $^1$H NMR (400 MHz, CDCl$_3$, mixture of rotamers) δ ppm 1.17-1.21 (m, 3H) 1.58-1.76 (m, 6H) 2.03-2.11 (m, 2H) 2.56-2.70 (m, 2H) 3.11-3.17 (m, 2H) 4.04-4.11 (m, 2H) 4.90-4.97 (m, 1H) 5.08-5.21 (m, 2H) 6.28-6.60 (m, 1H) 7.07-7.56 (m, 14H).

Following compound was prepared using similar procedure as described in example 18-1:

| Example # | Product | Condition | HPLC-RT (condition) | MS (M + 1) |
|---|---|---|---|---|
| Example 18-2 | 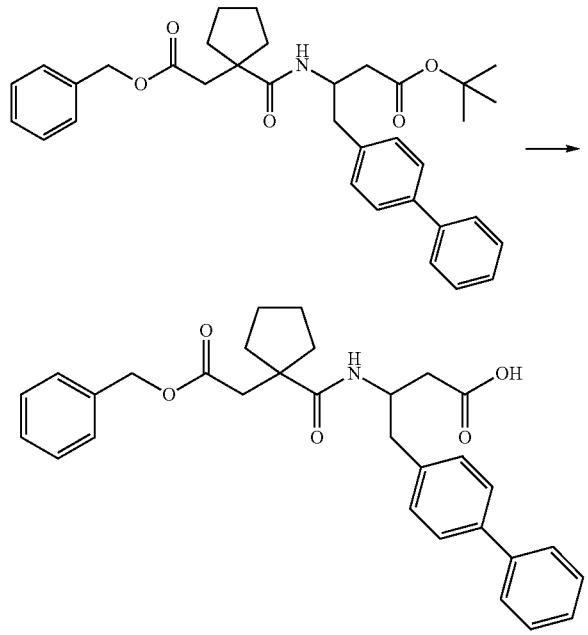(R)-methyl 3-(biphenyl-4-yl)-2-(1-(2-ethoxy-2-oxoethyl)cyclopentanecarboxamido)propanoate | EDCl, HOAt, DIPEA, DMF, rt | 1.82 min. (A) | 438.2 |

Example 18-2

¹H NMR (400 MHz, CDCl₃, mixture of rotamers) δ ppm 1.18-1.23 (m, 3H) 1.60-1.66 (m, 6H) 2.02-2.09 (m, 2H) 2.56-2.69 (m, 2H) 3.06-3.23 (m, 2H) 3.73-3.74 (m, 3H) 4.06-4.13 (m, 2H) 4.86-4.93 (m, 1H) 6.26-6.58 (m, 1H) 7.16-7.58 (m, 9H).

Example 19-1

Synthesis of 3-(1-(2-(benzyloxy)-2-oxoethyl)cyclopentanecarboxamido)-4-(biphenyl-4-yl)butanoic acid

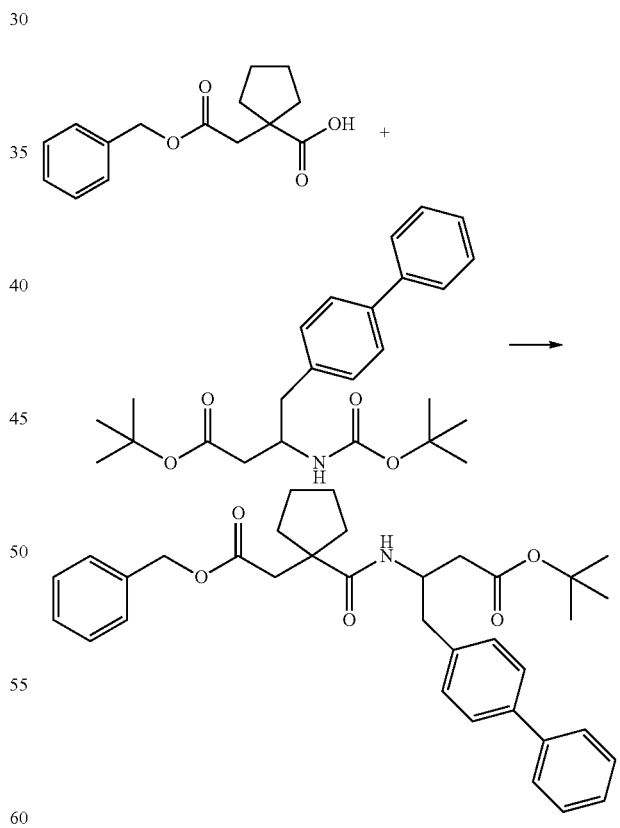

To a solution of tert-butyl 3-(1-(2-(benzyloxy)-2-oxoethyl)cyclopentanecarboxamido)-4-(biphenyl-4-yl)butanoate (38 mg, 0.068 mmol) in DCM (0.7 ml), TFA (0.263 ml, 3.42 mmol) was added. After stirred for 1 hour, the reaction mixture was concentrated to give 3-(1-(2-(benzyloxy)-2-oxoethyl)cyclopentanecarboxamido)-4-(biphenyl-4-yl)butanoic acid (39 mg); Retention time=1.73 minutes (condition B); MS (m+1)=500.4;

Example 20-1

Synthesis of tert-butyl 3-(1-(2-(benzyloxy)-2-oxoethyl)cyclopentanecarboxamido)-4-(biphenyl-4-yl)butanoate A mixture of tert-butyl 4-(biphenyl-4-yl)-3-(tert-butoxycarbonylamino)butanoate (110 mg, 0.267 mmol) and HCl in 1,4-dioxane (0.668 ml, 2.67 mmol) was stirred for 2 hours, and the reaction mixture was concentrated under reduced pressure. To a solution of 1-(2-(benzyloxy)-2-oxoethyl)cyclopentanecarboxylic acid (65.6 mg, 0.214 mmol, 86% purity), EDC.HCl (51.2 mg, 0.267 mmol) and 1-hydroxy-7-azabenzotriazole (36.4 mg, 0.267 mmol) in DMF (1 ml) stirred for 1.5 hour, the obtained residue and DIPEA (0.093 ml, 0.535 mmol) were added. After stirred for 2.5 hours, the reaction was diluted with water. The products were extracted with EtOAc, washed with brine, dried over Na$_2$SO$_4$, filtered, and concentrated under reduced pressure. The obtained residue was purified by flash column chromatography on silica gel (eluent: heptane/EtOAc=100:0 to 0:100) to give tert-butyl 3-(1-(2-(benzyloxy)-2-oxoethyl)cyclopentanecarboxamido)-4-(biphenyl-4-yl)butanoate (38 mg); Retention time=1.89 minutes (condition B); MS (m+1)=556.3.

Following compound was prepared using similar procedure as described in example 20-1:

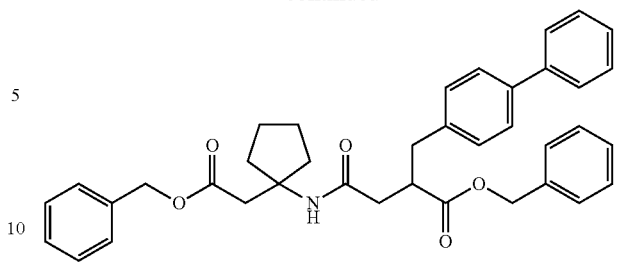

To a solution of benzyl 2-(1-aminocyclopentyl)acetate hydrochloride (66 mg, 0.245 mmol), 4-(benzyloxy)-3-(bi-

| Example # | Product | Condition | HPLC-RT (condition) | MS (M + 1) |
|---|---|---|---|---|
| Example 20-2 | benzyl 3-(1-(2-(benzyloxy)-2-oxoethyl)cyclopentanecarboxamido-2-(biphenyl-4-ylmethyl)propanoate | 1) HCl in 1,4-dioxane 2) EDCl, HOAt, DIPEA, DMF, rt | 1.81 min. (B) | 590.2 |

Example 20-2

$^1$H NMR (400 MHz, CDCl$_3$, mixture of rotamers) δ ppm 1.57-1.64 (m, 6H) 1.92-2.00 (m, 2H) 2.62-2.73 (m, 2H) 2.85-3.07 (m, 3H) 3.34-3.57 (m, 2H) 5.04-5.12 (m, 4H) 6.37-6.39 (m, 1H) 7.19-7.57 (m, 19H).

Example 21-1

Synthesis of benzyl 4-(1-(2-(benzyloxy)-2-oxoethyl)cyclopentylamino)-2-(biphenyl-4-ylmethyl)-4-oxobutanoate

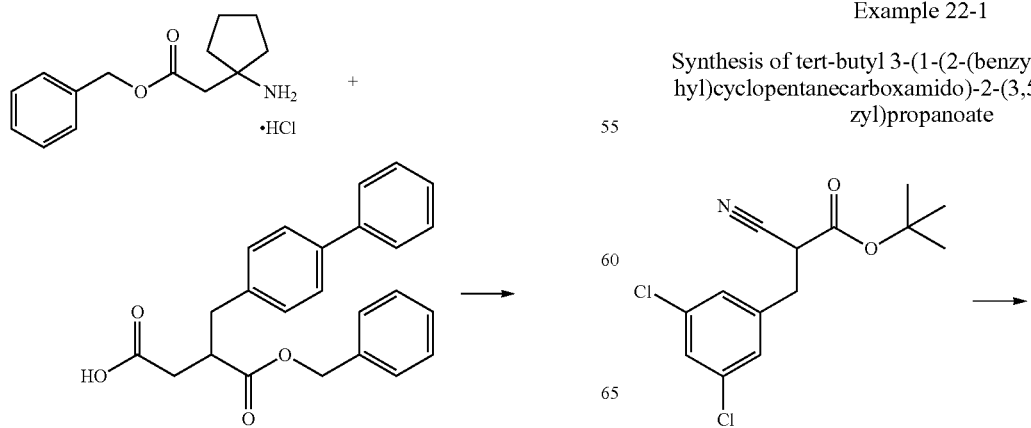

phenyl-4-ylmethyl)-4-oxobutanoic acid (78 mg, 0.209 mmol), WSC.HCl (60.1 mg, 0.314 mmol) and 1-hydroxy-7-azabenzotriazole (42.7 mg, 0.314 mmol) in DMF (2 ml) was added DIPEA (0.055 ml, 0.314 mmol) at room temperature. After stirred for 4 hours, the reaction was quenched with H$_2$O. The product was extracted with EtOAc, and the organic layer was washed with brine, dried over MgSO$_4$, filtered, and concentrated under reduced pressure. The obtained residue was purified by flash column chromatography on silica gel (eluent: heptane/EtOAc=100:0 to 0:100) to give benzyl 4-(1-(2-(benzyloxy)-2-oxoethyl)cyclopentylamino)-2-(biphenyl-4-ylmethyl)-4-oxobutanoate (93 mg); Retention time=1.85 minutes (condition B); MS (m+1)=590.3; $^1$H NMR (400 MHz, CDCl3, mixture of rotamers) δ ppm 1.61-1.72 (m, 6H) 1.96-2.06 (m, 2H) 2.17-2.46 (m, 2H) 2.81-3.00 (m, 4H) 3.22-3.29 (m, 1H) 5.02-5.12 (m, 4H) 5.62 (br s, 1H) 7.15-7.57 (m, 19H).

Example 22-1

Synthesis of tert-butyl 3-(1-(2-(benzyloxy)-2-oxoethyl)cyclopentanecarboxamido)-2-(3,5-dichlorobenzyl)propanoate

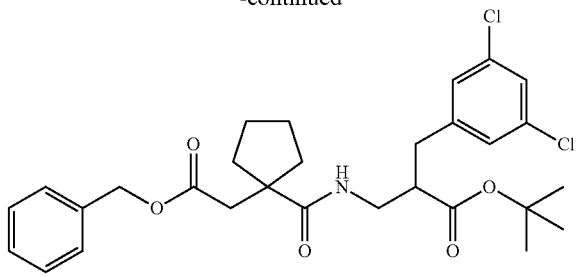

A suspension of tert-butyl 2-cyano-3-(3,5-dichlorophenyl) propanoate (100 mg, 0.333 mmol), Raney 2800 nickel (slurry in water) (185 mg, 3.14 mmol) and NH₄OH (1531 ml, 39.3 mmol) in EtOH (3 ml) was allowed to stir under hydrogen (1 atm) at 50° C. for 19 hours. The reaction mixture was cooled to room temperature and filtered. The filtrate was concentrated under reduced pressure to give a crude material (184 mg). A solution of the crude material, 1-(2-(benzyloxy)-2-oxoethyl)cyclopentanecarboxylic acid (103 mg, 0.393 mmol), EDC (98 mg, 0.511 mmol) and HOAt (69.6 mg, 0.511 mmol) in DMF (3 ml) was allowed to stir at room temperature for 2 hours. The reaction was quenched with H₂O and NH₄OH, and the product was extracted with EtOAc and washed with brine, dried over MgSO₄, filtered, and concentrated under reduced pressure. The residue was purified by flash column chromatography on silica gel (eluent: heptane/EtOAc=100:0 to 20:80) to give tert-butyl 341-(2-(benzyloxy)-2-oxoethyl)cyclopentanecarboxamido)-2-(3,5-dichlorobenzyl)propanoate (130 mg); Retention time=1.75 minutes (condition B); MS (m+1)=548.2; ¹H NMR (400 MHz, CDCl3, data for major rotamer) δ ppm 1.36 (s, 9H) 1.62-1.70 (m, 6H) 2.00-2.11 (m, 2H) 2.66-2.81 (m, 5H) 3.28-3.35 (m, 1H) 3.41-3.48 (m, 1H) 5.09 (s, 2H) 6.43-6.46 (m, 1H) 7.08 (d, J=2.0 Hz, 2H) 7.21 (t, J=2.0 Hz, 1H) 7.30-7.35 (m, 5H).

Example 23-1

Synthesis of tert-butyl 3-(1-(2-(benzyloxy)-2-oxoethyl)cyclopentanecarboxamido)-2-(3,4-dichlorobenzyl)propanoate

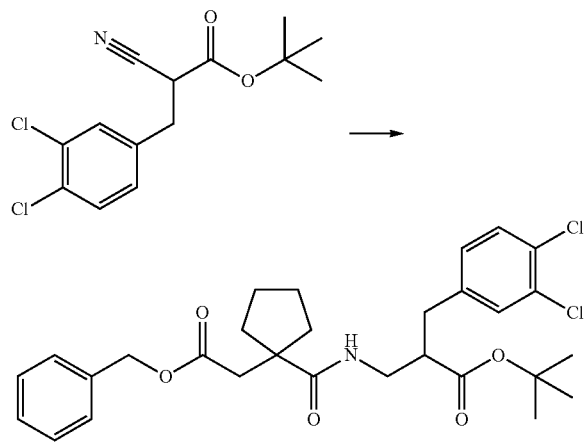

A suspension of tert-butyl 2-cyano-3-(3,4-dichlorophenyl) propanoate (100 mg, 0.333 mmol), Raney 2800 nickel (slurry in water) (156 mg, 2.67 mmol) and NH4OH (1.297 ml, 33.3 mmol) in EtOH (3 ml) was allowed to stir under hydrogen at room temperature for 14 hours. The reaction mixture was filtered and concentrated under reduced pressure to give a crude material (93 mg). A solution of the crude material, 1-(2-(benzyloxy)-2-oxoethyl)cyclopentanecarboxylic acid (87 mg, 0.333 mmol), EDC (83 mg, 0.433 mmol) and HOAt (58.9 mg, 0.433 mmol) in DMF (1 ml) was allowed to stir at room temperature for 2 hours. The reaction was quenched with H₂O, and the product was extracted with EtOAc and washed with brine, dried over MgSO4, filtered, and concentrated under reduced pressure. The obtained residue was purified by flash column chromatography on silica gel (eluent: heptane/EtOAc=100:0 to 20:80) to give tert-butyl 3-(1-(2-(benzyloxy)-2-oxoethyl)cyclopentanecarboxamido)-2-(3,4-dichlorobenzyl)propanoate (84.5 mg); Retention time=1.70 minutes (condition B); MS (m+1)=548.2; ¹H NMR (400 MHz, CDCl₃, data for major rotamer) δ ppm 1.37 (s, 9H) 1.61-1.70 (m, 6H) 2.00-2.07 (m, 2H) 2.66-2.84 (m, 5H) 3.26-3.48 (m, 2H) 5.08 (s, 2H) 6.43-6.46 (app t, 1H) 7.02-7.05 (m, 1H) 7.29-7.36 (m, 7H).

Example 24-1

Synthesis of tert-butyl 3-(1-(2-(benzyloxy)-2-oxoethyl)cyclopentanecarboxamido)-2-(4-methoxybenzyl)propanoate

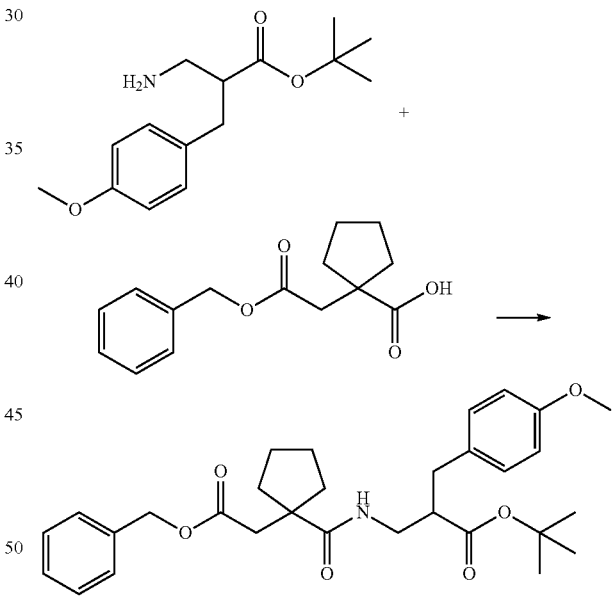

A solution of tert-butyl 3-amino-2-(4-methoxybenzyl)propanoate (50 mg, 0.188 mmol), 1-(2-(benzyloxy)-2-oxoethyl) cyclopentanecarboxylic acid (49.4 mg, 0.188 mmol), EDC (47.0 mg, 0.245 mmol) and HOAt (33.3 mg, 0.245 mmol) in DMF (2 ml) was allowed to stir at room temperature for 3 hours. The reaction mixture was diluted with H₂O and EtOAc. To the organic layer was added NH₄OH (6 ml) and washed with brine, dried over Na₂SO₄, filtered, and concentrated under reduced pressure. The obtained residue was purified by flash column chromatography on silica gel (eluent: heptane/EtOAc=100:0 to 50:50) to give tert-butyl 3-(1-(2-(benzyloxy)-2-oxoethyl)cyclopentanecarboxamido)-2-(4-methoxybenzyl)propanoate (56.3 mg); Retention time=1.61 minutes (condition B); MS (m+1)=510.5; ¹H NMR (400

MHz, CDCl₃) δ ppm 1.37 (s, 9H) 1.57-1.70 (m, 6H) 2.00-2.04 (m, 2H) 2.66-2.86 (m, 5H) 3.24-3.47 (m, 2H) 3.77 (s, 3H) 5.08 (s, 2H) 6.36-6.39 (m, 1H) 6.79-6.82 (m, 2H) 7.07-7.11 (m, 2H) 7.30-7.34 (m, 5H).

Example 25-1

Synthesis of (S)-Benzyl 14(S)-2-(2-(2-tert-butoxy-2-oxoethyl)-2,3-dihydro-1H-indene-2-carboxamido)-3-phenylpropanoyl)pyrrolidine-2-carboxylate

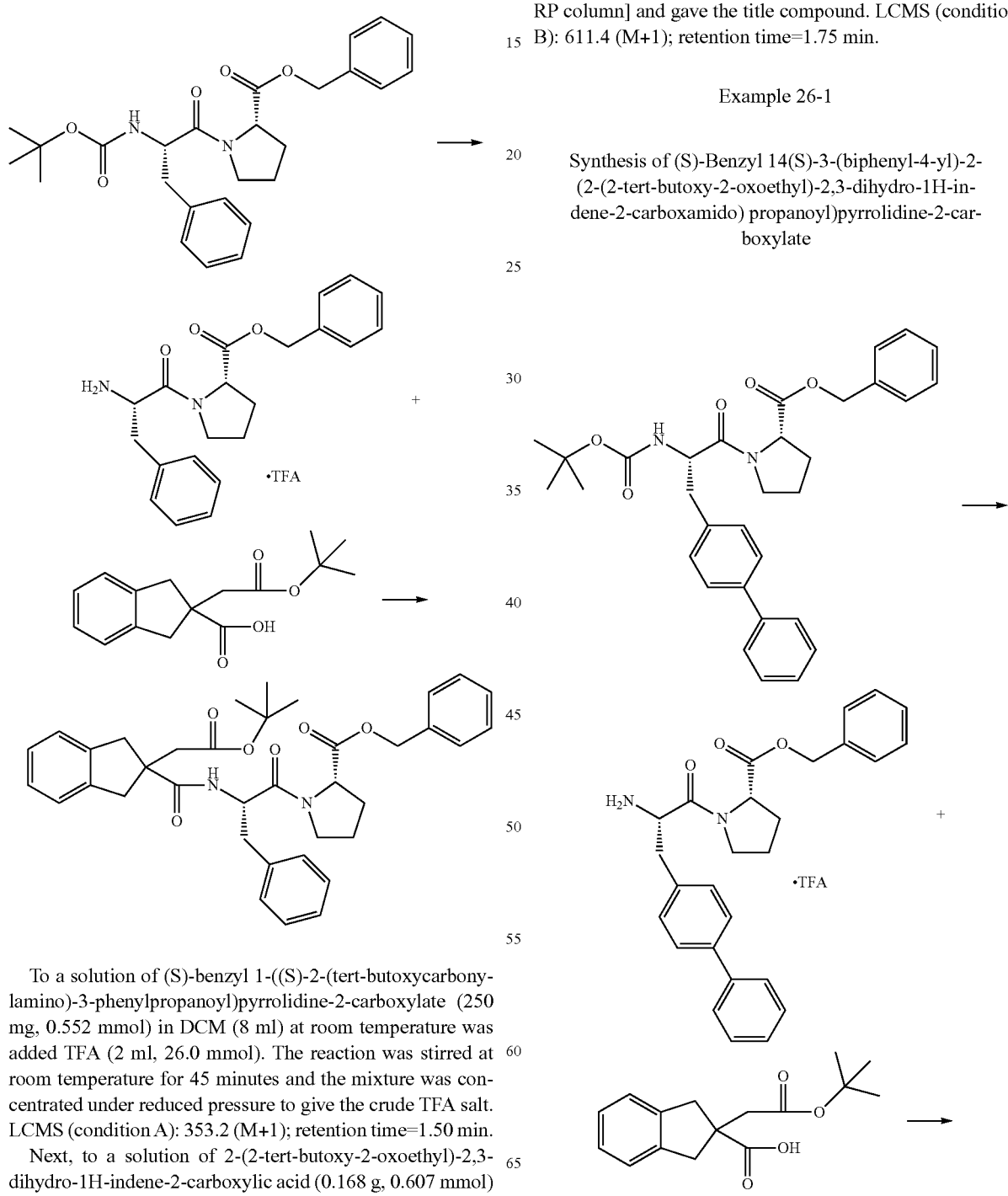

To a solution of (S)-benzyl 1-((S)-2-(tert-butoxycarbonylamino)-3-phenylpropanoyl)pyrrolidine-2-carboxylate (250 mg, 0.552 mmol) in DCM (8 ml) at room temperature was added TFA (2 ml, 26.0 mmol). The reaction was stirred at room temperature for 45 minutes and the mixture was concentrated under reduced pressure to give the crude TFA salt. LCMS (condition A): 353.2 (M+1); retention time=1.50 min.

Next, to a solution of 2-(2-tert-butoxy-2-oxoethyl)-2,3-dihydro-1H-indene-2-carboxylic acid (0.168 g, 0.607 mmol) in THF (10 ml) at room temperature was added EDC.HCl (0.159 g, 0.828 mmol) and HOBT (0.110 g, 0.718 mmol). The reaction was stirred at room temperature for 10 minutes followed by the addition of (S)-benzyl 1-((S)-2-amino-3-phenylpropanoyl)pyrrolidine-2-carboxylate trifluoroacetate (0.195 g, 0.552 mmol) and TEA (0.231 ml, 1.656 mmol). The reaction was stirred for 10 minutes and was quenched by brine and extracted with EtOAc. The combined organic layer was washed with brine and dried over anhydrous sodium sulfate, filtered and concentrated under reduced pressure. The obtained residue was purified by reverse phase HPLC [40 to 80% ACN-water (0.1% NH₄OH) over 10 min by X-Bridge RP column] and gave the title compound. LCMS (condition B): 611.4 (M+1); retention time=1.75 min.

Example 26-1

Synthesis of (S)-Benzyl 14(S)-3-(biphenyl-4-yl)-2-(2-(2-tert-butoxy-2-oxoethyl)-2,3-dihydro-1H-indene-2-carboxamido) propanoyl)pyrrolidine-2-carboxylate

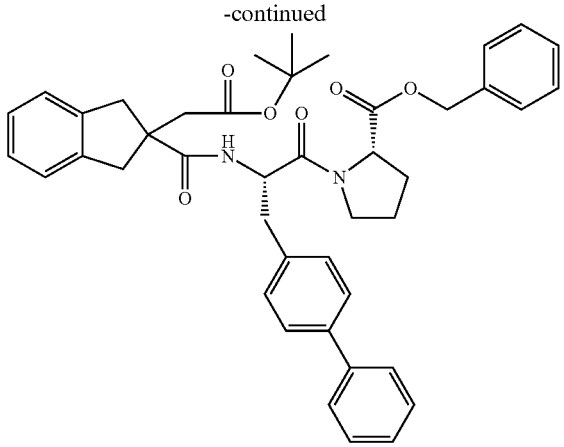

To a solution of (S)-benzyl 1-((S)-3-(biphenyl-4-yl)-2-(tert-butoxycarbonylamino) propanoyl)pyrrolidine-2-carboxylate (200 mg, 0.378 mmol) in DCM (8 ml) at room temperature was added trifluoroacetic acid (0.729 ml, 9.46 mmol) and the reaction mixture was stirred at room temperature for 2 hours. The reaction mixture was concentrated to dryness as salt and used directly for the next reaction without further purification. LCMS (condition B): 429.1 (M+1); retention time=1.13 min.

Next, to a solution of the above salt (162 mg, 0.378 mmol) in THF (10 ml) at room temperature was added 2-(2-tert-butoxy-2-oxoethyl)-2,3-dihydro-1H-indene-2-carboxylic acid (125 mg, 0.452 mmol), 1-hydroxybenzotriazole hydrate (75 mg, 0.491 mmol), EDC.HCl (109 mg, 0.567 mmol) and triethylamine (0.158 ml, 1.134 mmol). The mixture was stirred at room temperature for 1 hour. The reaction was quenched by brine and was extracted with EtOAc. The combined organic layer was washed with brine and dried over anhydrous sodium sulfate, filtered and concentrated under reduced pressure. The obtained residue was purified by flash chromatography (silica gel, 10 to 40% EtOAc/HEP) gave the title compound: 163 mg (yield: 63%). LCMS (condition B): 687.4 (M+1); retention time=1.74 min.

Example 27-1

Synthesis of Tert-butyl 3-(1-(2-(benzyloxy)-2-oxoethyl)cyclopentanecarboxamido)-2-(4-(pyridin-2-yl)benzyl) propanoate

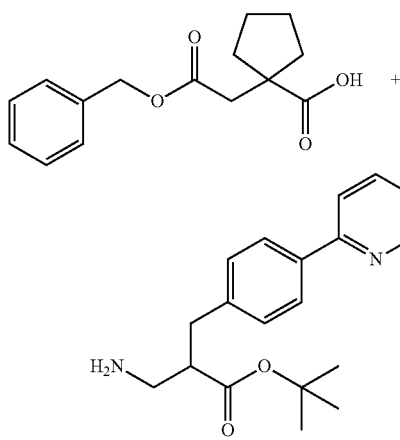

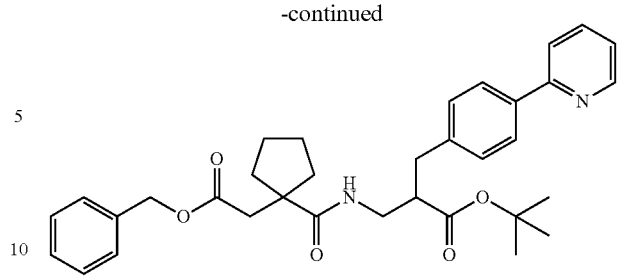

To a solution of 1-(2-(benzyloxy)-2-oxoethyl)cyclopentanecarboxylic acid (128 mg, 0.487 mmol) in THF (8 ml) at room temperature was added tert-butyl 3-amino-2-(4-(pyridin-2-yl)benzyl) propanoate (152 mg, 0.487 mmol), EDC.HCl (166 mg, 0.730 mmol), HOBT (97 mg, 0.633 mmol) and TEA (0.081 ml, 0.584 mmol). The mixture was stirred at room temperature overnight. The reaction was quenched by brine and was extracted with EtOAc. The combined organic layer was washed with brine and dried over anhydrous sodium sulfate, filtered and concentrated under reduced pressure. The obtained residue was purified by flash chromatography (silica gel, 20 to 50% EtOAc/HEP) and gave the title compound. LCMS (condition B): 557.4 (M+1); retention time=1.53 min.

Example 28-1

Synthesis of Tert-butyl 4-(1-(2-(benzyloxy)-2-oxoethyl)cyclopentylamino)-3-(biphenyl-4-ylmethyl)-4-oxobutanoate

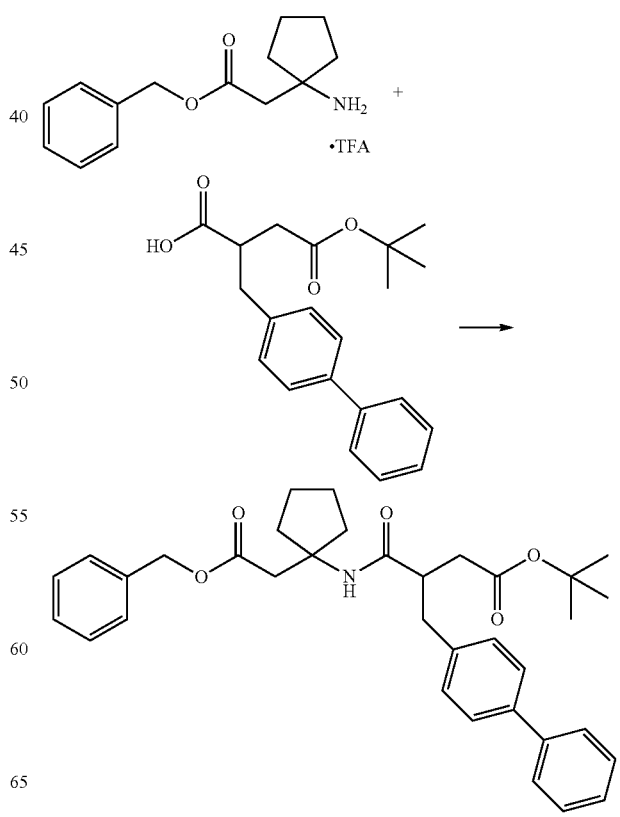

To a suspension of 2-(biphenyl-4-ylmethyl)-4-tert-butoxy-4-oxobutanoic acid (0.119 g, 0.350 mmol) in THF (10 ml) at room temperature was added EDC.HCl (0.091 g, 0.477 mmol) and HOBT (0.063 g, 0.413 mmol), and the mixture was stirred at room temperature 10 minutes. To the mixture was added benzyl 2-(1-aminocyclopentyl)trifluoroacetate (0.074 g, 0.318 mmol) in THF (5 mL) followed by TEA (0.133 ml, 0.954 mmol). The reaction was stirred at room temperature for 1 hour. The reaction was quenched by brine and was extracted with EtOAc. The combined organic layer was washed with brine and dried over anhydrous sodium sulfate, filtered and concentrated under reduced pressure. The obtained residue was purified by reverse phase HPLC [40 to 90% ACN-water (0.1% NH₄OH) over 10 min by X-Bridge 18 column] and gave the title compound. LCMS (condition G): 556.5 (M+1); retention time=1.03 min.

Example 29-1

Synthesis of (S)-Benzyl 2-(1-(2-(3'-chlorobiphenyl-4-yl)-1-(1H-tetrazol-5-yl)ethylcarbamoyl)cyclopentyl)acetate

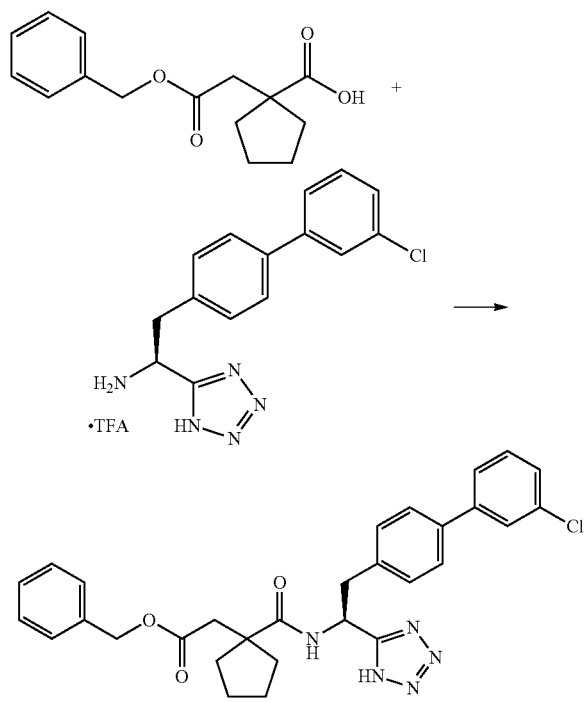

To a suspension of 1-(2-(benzyloxy)-2-oxoethyl)cyclopentanecarboxylic acid (197 mg, 0.750 mmol) in THF (8 ml) at room temperature was added EDC.HCl (192 mg, 1.000 mmol) and HOBT (134 mg, 0.875 mmol). The mixture was stirred at room temperature for 10 minutes and was added a solution of (S)-2-(3'-chlorobiphenyl-4-yl)-1-(1H-tetrazol-5-yl)ethanamine (187 mg, 0.625 mmol) in THF and TEA (0.174 ml, 1.250 mmol). The mixture was stirred overnight at room temperature. The reaction was quenched by brine and was extracted with EtOAc. The combined organic layer was washed with brine and dried over anhydrous sodium sulfate, filtered and concentrated under reduced pressure. The obtained residue was purified by flash chromatography (silica gel, 1 to 3% EtOH/DCM) and gave the title compound: 134 mg (yield: 39%). LCMS (condition B): 544.3 (M+1); retention time=1.44 min.

Example 30-1

Synthesis of (S)-benzyl 2-(1-(2-(3'-methylbiphenyl-4-yl)-1-(1H-tetrazol-5-yl)ethylcarbamoyl)cyclopentyl)acetate

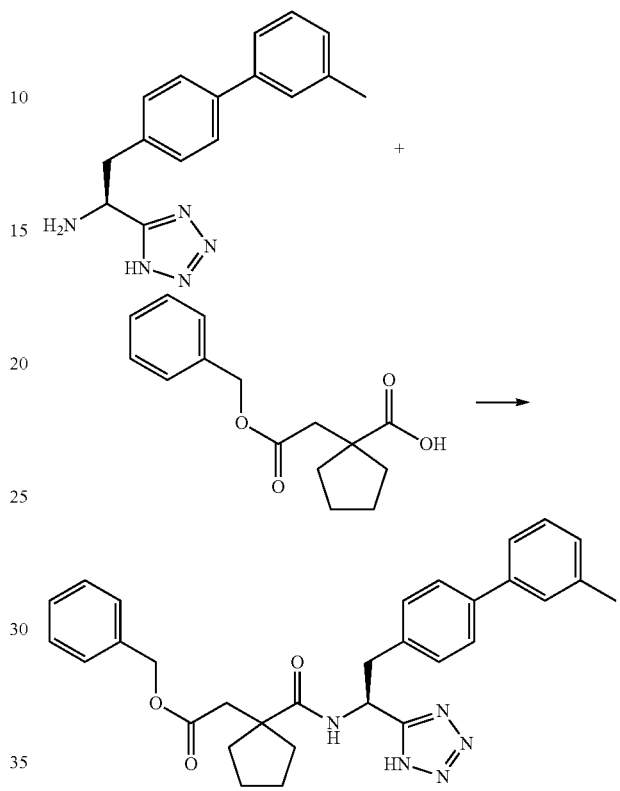

To a solution of 1-(2-(benzyloxy)-2-oxoethyl)cyclopentanecarboxylic acid (150 mg, 0.572 mmol) in DMF (3 mL) were added EDC-HCl (110 mg, 0.572 mmol), HOAt (62.3 mg, 0.423 mmol) and triethylamine (0.133 mL, 0.953 mmol) at room temperature. After being stirred for 0.5 hours, (S)-2-(3-methylbiphenyl-4-yl)-1-(1H-tetrazol-5-yl)ethanamine (106 mg, 0.381 mmol) was added and stirred for 2 hours. The reaction mixture was diluted with EtOAc and washed with saturated NH₄Cl aqueous solution and brine. The organic layer was dried over Na₂SO₄, concentrated under reduced pressure, and purified by silica gel flash column chromatography (10% MeOH in DCM/DCM) to give (S)-benzyl 2-(1-(2-(3'-methylbiphenyl-4-yl)-1-(1H-tetrazol-5-yl)ethylcarbamoyl)cyclopentyl)acetate. LCMS (condition A): 524 (M+1); retention time=1.82 min.

Example 31-1

Synthesis of (R)-benzyl 2-(1-(2-(biphenyl-4-yl)-1-(1-(2-cyanoethyl)-1H-tetrazol-5-yl)ethylcarbamoyl)cyclopentyl)acetate

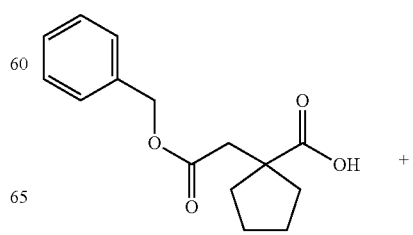

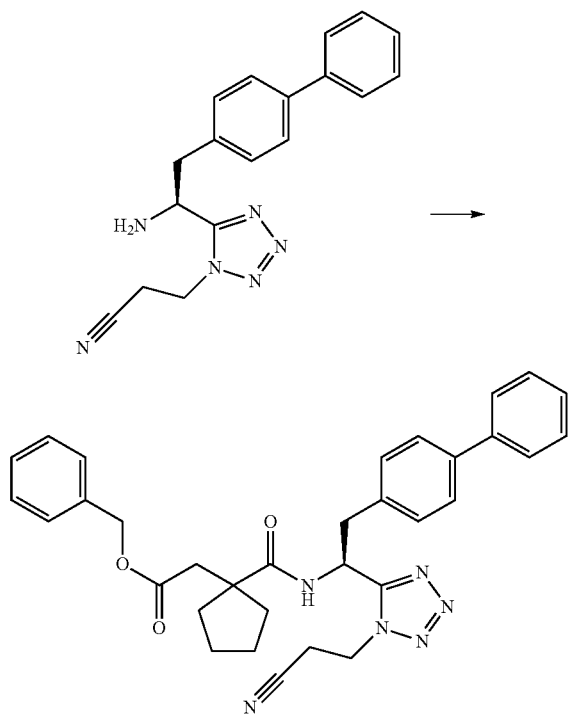

To a solution of 1-(2-(benzyloxy)-2-oxoethyl)cyclopentanecarboxylic acid (49.4 mg, 0.188 mmol) and (R)-3-(5-(1-amino-2-(biphenyl-4-yl)ethyl)-1H-tetrazol-1-yl)propanenitrile (50 mg, 0.157 mmol) in DMF (1.5 mL) were added EDC.HCl (36 mg, 0.188 mmol), HOAt (26 mg, 0.188 mmol) and triethylamine (0.033 mL, 0.236 mmol). After being stirred for 2 hours, the reaction mixture was diluted with EtOAc. The mixture was washed with H2O2O and brine, dried over Na2SO4 and concentrated. The residue was purified by silica gel flash column chromatography (eluent; EtOAc/heptane) to give (R)-benzyl 2-(1-(2-(biphenyl-4-yl)-1-(1-(2-cyanoethyl)-1H-tetrazol-5-yl)ethylcarbamoyl)cyclopentyl)acetate (39 mg). LCMS (condition A) δ 563 (M+1); retention time=1.85 min.

Example 32-2

Synthesis of {1-[(S)-2-Biphenyl-4-yl-1-(1H-tetrazol-5-yl)-ethylcarbamoyl]-cyclopentyl}-acetic acid

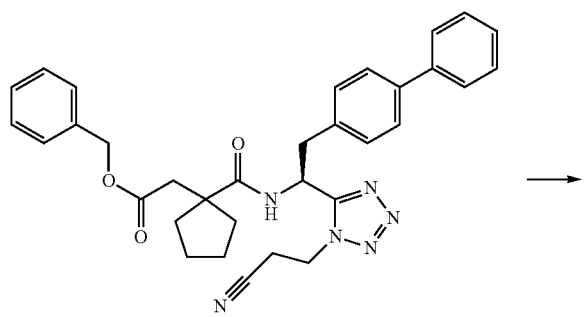

(S)-benzyl 2-(1-(2-(biphenyl-4-yl)-1-(1-(2-cyanoethyl)-1H-tetrazol-5-yl)ethylcarbamoyl)cyclopentyl)acetate (39 mg, 0.069 mmol) in MeOH (6 mL) was hydrogenated in H-Cube (Cartridge; 10% Pd/C) at room temperature for 0.5 hour. The reaction mixture was concentrated in vacuo. This was treated with 2M NaOH aqueous solution (1 mL) and MeOH (1 mL) and stirred for 0.5 hour. The reaction mixture was acidified with 1M HCl and the mixture was purified by reverse phase HPLC (column; Sunfire C-18, eluent; 0.1% TFA-H₂O/CH₃CN) to give {1-[(S)-2-biphenyl-4-yl-1-(1H-tetrazol-5-yl)-ethylcarbamoyl]-cyclopentyl}-acetic acid (2.5 mg). LCMS (condition C): 420 (M+1); retention time=1.70 min. $^1$H NMR (400 MHz, DMSO-d6) δ ppm 1.36-1.54 (m, 6H), 1.87-1.98 (m, 2H), 2.59 (s, 3H), 2.59 (s, 2H), 3.22-3.66 (m, 2H), 5.39-5.48 (m, 1H), 7.29-7.37 (m, 3H), 7.44 (t, J=8.08 Hz, 2H), 7.55 (t, J=8.34 Hz, 2H), 7.59-7.64 (m, 2H), 8.17 (d, J=8.08 Hz, 1H); HRMS (ES+) m/z for C23H25N5O3 [M+H]+ calcd 419.2. found 419.2

Starting materials or intermediates were prepared in following manner:

Intermediate 1-1

Synthesis of 1-(2-(benzyloxy)-2-oxoethyl)cyclopentanecarboxylic acid

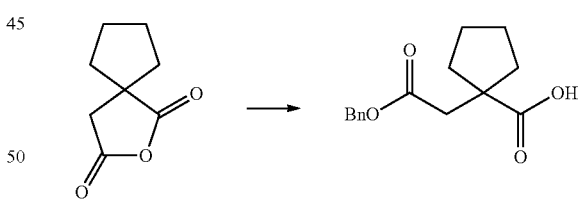

To a solution of 2-oxaspiro[4.4]nonane-1,3-dione (3 g, 19.46 mmol) in toluene (2 ml), BnOH (2.023 ml, 19.46 mmol) was added. The reaction mixture was allowed to stir at 100° C. for 19 hours, and the reaction mixture was concentrated under reduced pressure. The obtained residue was recrystallized in DCM (15 ml) and 2,2,4-trimethylpentane (100 ml). The obtained colorless crystal was washed with a 10% solution of DCM/heptane (20 ml). The obtained solid was dried under reduce pressure to give 1-(2-(benzyloxy)-2-oxoethyl)cyclopentanecarboxylic acid (3.09 g); Retention time=1.56 minutes (condition A); $^1$H NMR (400 MHz, CDCl3) δ ppm 1.24 (t, J=7.2 Hz, 3H) 1.58-1.81 (m, 6H) 2.19-2.25 (m, 2H) 2.75 (s, 2H) 5.11 (s, 2H) 7.28-7.37 (m, 5H) 11.80 (br s, 1H).

Intermediate 2-1

Synthesis of (S)-benzyl 1-((S)-2-amino-3-(biphenyl-4-yl)propanoyl)pyrrolidine-2-carboxylate hydrochloride

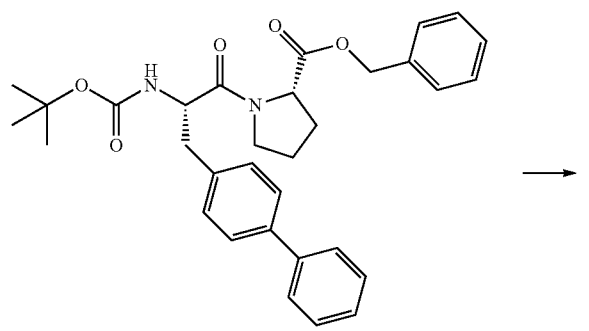

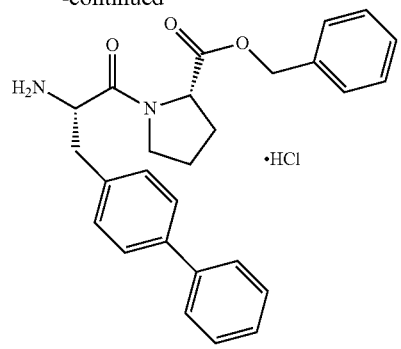

A solution of (S)-benzyl 1-((S)-3-(biphenyl-4-yl)-2-(tert-butoxycarbonylamino)propanoyl)pyrrolidine-2-carboxylate (429 mg, 0.812 mmol) and HCl in 1,4-dioxane (2.03 ml, 8.12 mmol) was allowed to stir for 1 hour and concentrated under reduced pressure to give (S)-benzyl 1-((S)-2-amino-3-(biphenyl-4-yl)propanoyl)pyrrolidine-2-carboxylate hydrochloride (396 mg); Retention time=1.00 minutes (condition B); MS (m+1)=429.2.

Following intermediates were prepared using similar procedure as described in Intermediate 2-1:

| Intermediate # | Product | Condition | HPLC-RT (condition) | MS (M+1) |
|---|---|---|---|---|
| Intermediate 2-2 | 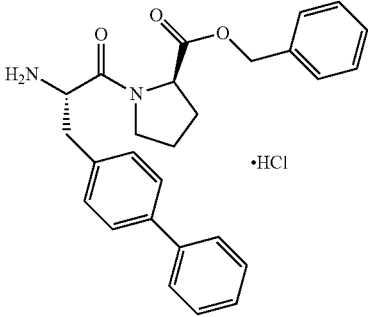<br>(R)-3-(2-aminopyrimidine-4-carboxamido)-4-(biphenyl-4-yl)butanoic acid hydrochloride | 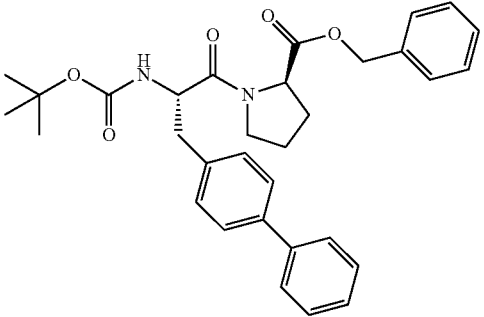<br>HCl in 1,4-dioxane, rt | 1.28 min. (B) | 429.3 |
| Intermediate 2-3 | 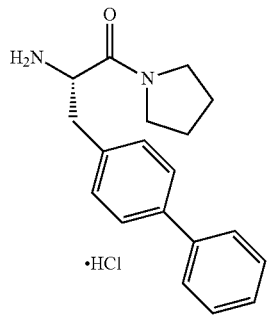<br>(S)-2-amino-3-(biphenyl-4-yl)-1-(pyrrolidin-1-yl)propan-1-one hydrochloride | 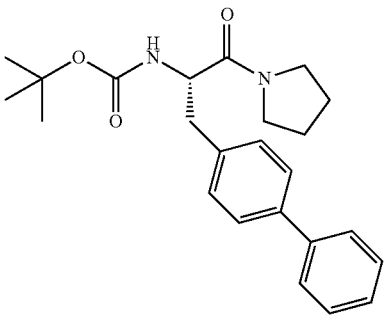<br>HCl in 1,4-dioxane, rt | 0.62 min. (B) | 295.2 |

| Intermediate # | Product | Condition | HPLC-RT (condition) | MS (M+1) |
|---|---|---|---|---|
| Intermediate 2-4 | (S)-ethyl 1-((S)-2-amino-3-(biphenyl-4-yl)propanoyl)pyrrolidine-2-carboxylate hydrochloride | HCl in 1,4-dioxane, rt | 0.94 min. (B) | 367.4 |
| Intermediate 2-5 | (S)-benzyl 1-((S)-3-amino-4-(biphenyl-4-yl)butanoyl)pyrrolidine-2-carboxylate hydrochloride | HCl in 1,4-dioxane, rt | 0.94 min. (B) | 443.3 |

Intermediated 3-1

Synthesis of (S)-benzyl 14(S)-3-(biphenyl-4-yl)-2-(tert-butoxycarbonylamino)propanoyl)pyrrolidine-2-carboxylate

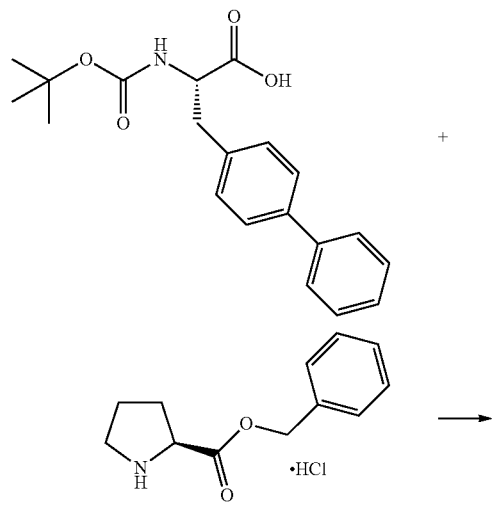

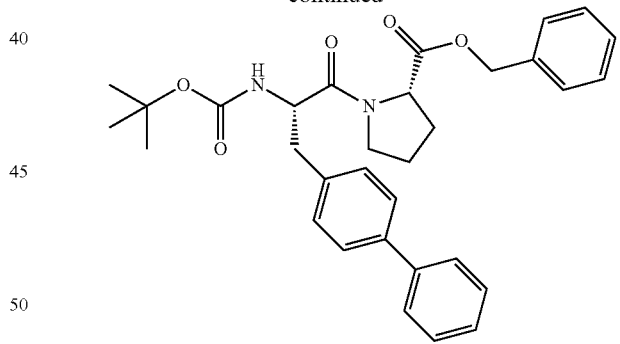

A solution of (S)-3-(biphenyl-4-yl)-2-(tert-butoxycarbonylamino)propanoic acid (1 g, 2.93 mmol), (S)-benzyl pyrrolidine-2-carboxylate hydrochloride (0.803 g, 3.22 mmol), PyBOP (1.600 g, 3.08 mmol), and DIPEA (1.074 ml, 6.15 mmol) in acetonitrile (10 ml) was allowed to stir at room temperature under nitrogen for 3 hours. The reaction mixture was diluted with H₂O, and the product was extracted with EtOAc. The organic layer was washed twice with 0.2 M HCl and once with brine, dried over Na₂SO₄, filtered, and concentrated under reduced pressure. The obtained residue was purified by flash column chromatography on silica gel (heptane/EtOAc=100:0 to 50:50) to give (S)-benzyl 14(S)-3-(biphenyl-4-yl)-2-(tert-butoxycarbonylamino)propanoyl) pyrrolidine-2-carboxylate (1.424 g); Retention time=1.69 minutes (condition B); MS (m+1)=529.3.

Following intermediates were prepared using similar procedure as described in Intermediate 3-1:

| Example # | Product | Condition | HPLC-RT (condition) | MS (M + 1) |
|---|---|---|---|---|
| Intermediate 3-2 | (R)-benzyl 1-((S)-3-(biphenyl-4-yl)-2-(tert-butoxycarbonylamino)propanoyl)pyrrolidine-2-carboxylate | PyBOP, DIPEA, DMF, rt (with pyrrolidine benzyl ester·HCl) | 1.72 min. (B) | 529.2 |
| Intermediate 3-3 | (S)-ethyl 1-((S)-3-(biphenyl-4-yl)-2-(tert-butoxycarbonylamino)propanoyl)pyrrolidine-2-carboxylate | PyBOP, DIPEA, DMF, rt (with pyrrolidine ethyl ester·HCl) | 1.57 min. (B) | 467.3 |

Intermediate 4-1

Synthesis of 1-(2-ethoxy-2-oxoethyl)cyclopentanecarboxylic acid

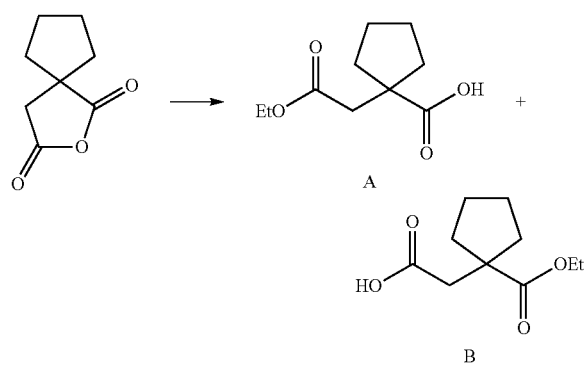

A solution of 2-oxaspiro[4.4]nonane-1,3-dione (522 mg, 3.39 mmol) in anhydrous EtOH (15 ml) was allowed to stir at 70° C. for 22 hours under nitrogen. The reaction mixture was concentrated to give a crude 1-(2-ethoxy-2-oxoethyl)cyclopentanecarboxylic acid (compound A, 672 mg). The product (86% purity) was used for next step without further purification; $^1$H NMR (400 MHz, CDCl3) δ ppm 1.24 (t, J=7.2 Hz, 3H) 1.57-1.81 (m, 6H) 2.19-2.25 (m, 2H) 2.69 (s, 2H) 4.12 (q, J=7.2 Hz, 3H) 11.65 (br s, 1H).

Intermediate 5-1

Synthesis of (S)-ethyl pyrrolidine-2-carboxylate hydrochloride

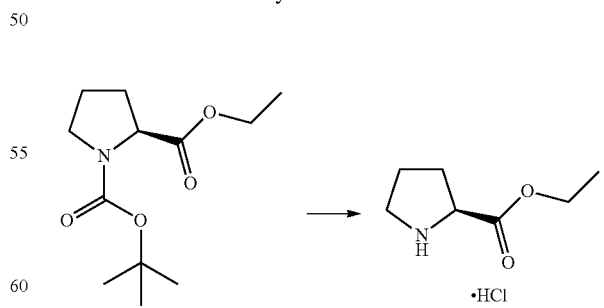

A mixture of (S)-1-tert-butyl 2-ethyl pyrrolidine-1,2-dicarboxylate (200 mg, 0.822 mmol) and HCl in 1,4-dioxane (4110 µl, 16.44 mmol) was allowed to stir for 1 hour. The reaction mixture was concentrated to give (S)-ethyl pyrrolidine-2-carboxylate hydrochloride; $^1$H NMR (400 MHz, CDCl3) δ ppm 1.32 (t, J=7.2 Hz, 3H) 2.00-2.22 (m, 3H) 2.39-2.48 (m, 1H) 3.49-3.67 (m, 2H) 4.29 (q, J=7.2 Hz, 3H) 9.09 (br s, 1H) 10.98 (br s, 1H).

Intermediate 6-1

Synthesis of (S)-benzyl 1-((S)-4-(biphenyl-4-yl)-3-(tert-butoxycarbonylamino)butanoyl)pyrrolidine-2-carboxylate

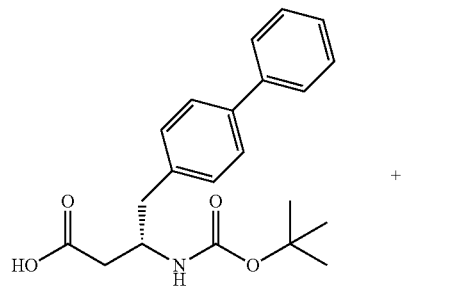

+

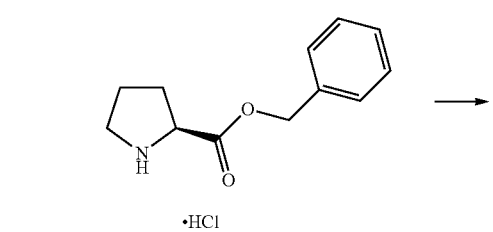

·HCl

→

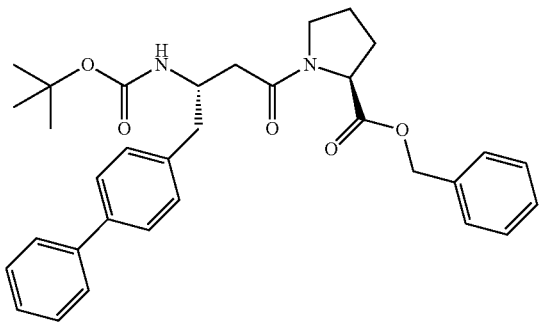

To a suspension of (S)-4-(biphenyl-4-yl)-3-(tert-butoxycarbonylamino)butanoic acid (374 mg, 0.832 mmol), (S)-benzyl pyrrolidine-2-carboxylate hydrochloride (209 mg, 0.998 mmol), WSC.HCl (191 mg, 0.998 mmol) and 1-hydroxy-7-azabenzotriazole (136 mg, 0.998 mmol) in DMF (8 ml), DIPEA (0.218 ml, 1.247 mmol) was added. After stirring for 3 hours, the reaction was diluted with H$_2$O, and the product was extracted with EtOAc. The combined organic layer was washed with brine, dried over Na$_2$SO$_4$, filtered, and concentrated under reduced pressure. The residue was purified by flash column chromatography on silica gel (eluent: heptane/EtOAc=85:15 to 0:100) to give (S)-benzyl 14(S)-4-(biphenyl-4-yl)-3-(tert-butoxycarbonylamino)butanoyl)pyrrolidine-2-carboxylate (41.3 mg); Retention time=1.72 minutes (condition B); MS (m+1)=543.3.

Intermediate 7-1

Synthesis of tert-butyl 4-(biphenyl-4-yl)-3-(tert-butoxycarbonylamino)butanoate

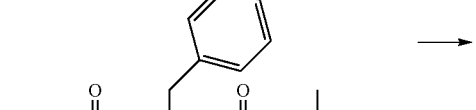

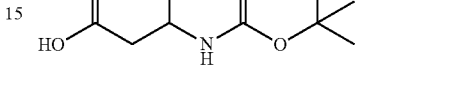

→

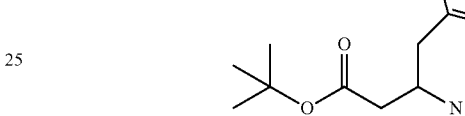

A solution of 4-(biphenyl-4-yl)-3-(tert-butoxycarbonylamino)butanoic acid (250 mg, 0.703 mmol), t-BuOH (0.135 ml, 1.407 mmol), EDCl (270 mg, 1.407 mmol) and 4-dimethylaminopyridine (86.0 mg, 0.704 mmol) in DCM (7 ml) was allowed to stir at room temperature under nitrogen for 62 hours. The reaction was quenched with water, and the organic layer was separated and concentrated under reduced pressure. The obtained residue was purified by flash column chromatography on silica gel to give tert-butyl 4-(biphenyl-4-yl)-3-(tert-butoxycarbonylamino)butanoate (110 mg); HPLC retention time=1.77 minutes (condition B); MS (ES+)=412.1 (m+1) 300.0 (m-tBux2+3; 100%); $^1$H NMR (400 MHz, CHLOROFORM-d) δ ppm 1.41 (s, 9H) 1.47 (s, 9H) 2.36 (A of ABX, J$_{ab}$=15.5 Hz, J$_{ax}$=6.2 Hz, 1H) 2.44 (B of ABX, J$_{ab}$=15.5 Hz, J$_{bx}$=5.6 Hz) 2.82-2.94 (m, 2H) 4.11-4.17 (m, 1H) 5.08-5.10 (m, 1H) 7.25-7.34 (m, 3H) 7.41-7.44 (m, 2H) 7.51-7.58 (m, 4H).

Intermediate 8-1

Synthesis of benzyl 2-(1-aminocyclopentyl)acetate hydrochloride

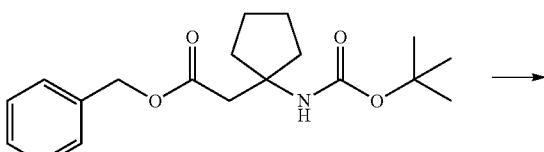

→

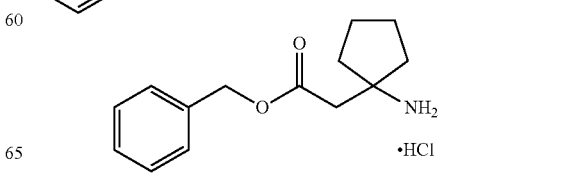

·HCl

A mixture of benzyl 2-(1-(tert-butoxycarbonylamino)cyclopentyl)acetate (82 mg, 0.246 mmol) and HCl in 1,4-dioxane (1230 μl, 4.92 mmol) was allowed to stir for 1 hour. The reaction mixture was concentrated to give 2-(1-aminocyclopentyl)acetate hydrochloride (66 mg); ¹H NMR (400 MHz, CDCl3) δ ppm 1.65-1.68 (m, 4H) 1.98-2.08 (m, 2H) 2.19-2.26 (m, 2H) 2.94 (s, 2H) 5.17 (s, 2H) 7.31-7.39 (m, 5H) 8.65 (br s, 3H).

Intermediate 9-1

Synthesis of 4-(benzyloxy)-3-(biphenyl-4-ylmethyl)-4-oxobutanoic acid

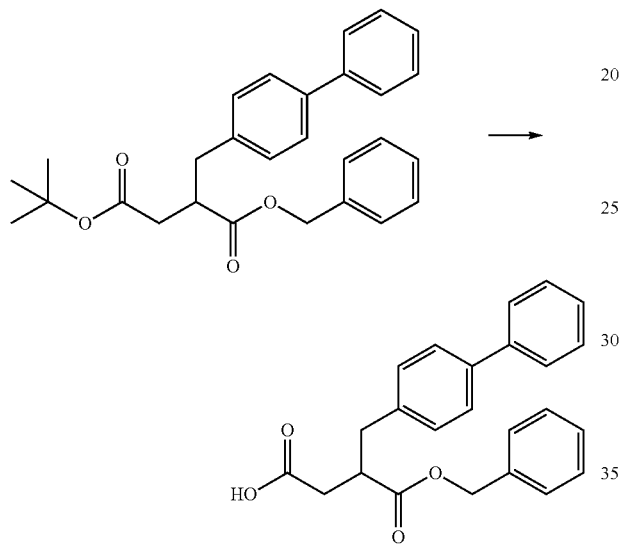

To a solution of 1-benzyl 4-tert-butyl 2-(biphenyl-4-ylmethyl)succinate (90 mg, 0.209 mmol) in DCM (1 ml), TFA (0.322 ml, 4.18 mmol) was added. The reaction mixture was allowed to stir for 1 hour, and then concentrated under reduced pressure to give 4-(benzyloxy)-3-(biphenyl-4-ylmethyl)-4-oxobutanoic acid (78 mg); Retention time=1.48 minutes (condition B); MS (m−1)=373.2.

Intermediate 10-1

Synthesis of 1-benzyl 4-tert-butyl 2-(biphenyl-4-ylmethyl)succinate

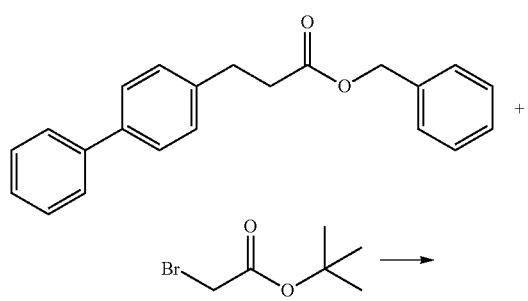

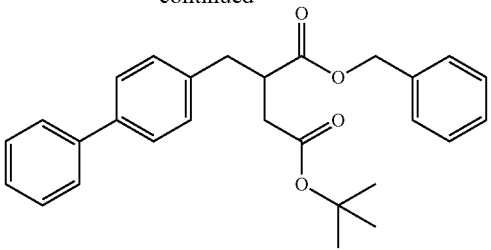

To a solution of diisopropylamine (2.70 ml, 18.96 mmol) in THF (20 ml), BuLi in hexanes (11.85 ml, 18.96 mmol) was added under nitrogen at 0° C. After stirred for 0.5 hour at the same temperature, the solution was cooled to −78° C. and then a solution of benzyl 3-(biphenyl-4-yl)propanoate (5 g, 15.80 mmol) in THF (20 ml) was added. After stirred for 1.5 hour at the same temperature, tert-butyl bromoacetate (3.33 ml, 22.12 mmol) was added, and then the mixture was warmed up to 0° C. The reaction mixture was allowed to stir at 0° C. for 2 hours, and then stirred at room temperature for 14 hours. The reaction mixture was poured into 150 ml of saturated aq. NH₄Cl. The product was extracted twice with EtOAc. The combined organic layer was washed with brine, dried over MgSO₄, filtered, and concentrated under reduced pressure. The obtained residue was purified by flash column chromatography on silica gel (eluent: heptane/EtOAc=100:0 to 10:1) to give the 1-benzyl 4-tert-butyl 2-(biphenyl-4-ylmethyl)succinate (2.97 g); Retention time=1.00 minutes (condition G); MS (m+1)=431.2.

Intermediate 11-1

Synthesis of benzyl 3-(biphenyl-4-yl)propanoate

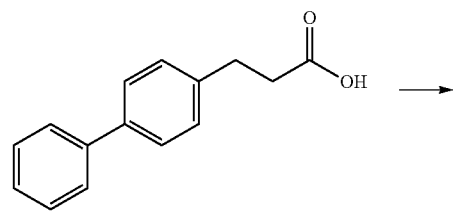

To a suspension of 3-(biphenyl-4-yl)propanoic acid (5 g, 22.10 mmol) and K₂CO₃ (6.11 g, 44.2 mmol) in DMF (22 ml), BnBr (3.94 ml, 33.1 mmol) was added. After stirred for 15 hours, additional BnBr (3.94 ml, 33.1 mmol) was added. After stirred for further 22 hours, the reaction was diluted with H₂O, extracted with EtOAc, washed with brine, dried over MgSO4, filtered, and concentrated under reduced pressure. The obtained residue was diluted with EtOAc (150 ml), and NH-silica gel was added to the suspension. The EtOAc was evaporated, and the resulted slurry was allowed to stir for 1 hour. The slurry was eluted with 10% EtOAc/heptane (150 ml) to give benzyl 3-(biphenyl-4-yl)propanoate (6.16 g);

Retention time=1.71 minutes (condition A); ¹H NMR (400 MHz, CDCl3) δ ppm 2.72 (t, J=7.8 Hz, 2H) 3.01 (t, J=7.8 Hz, 2H) 5.12 (s, 2H) 7.21-7.47 (m, 14H).

Intermediate 12-1

Synthesis of benzyl 3-(biphenyl-4-yl)-2-((tert-butoxycarbonylamino)methyl)propanoate

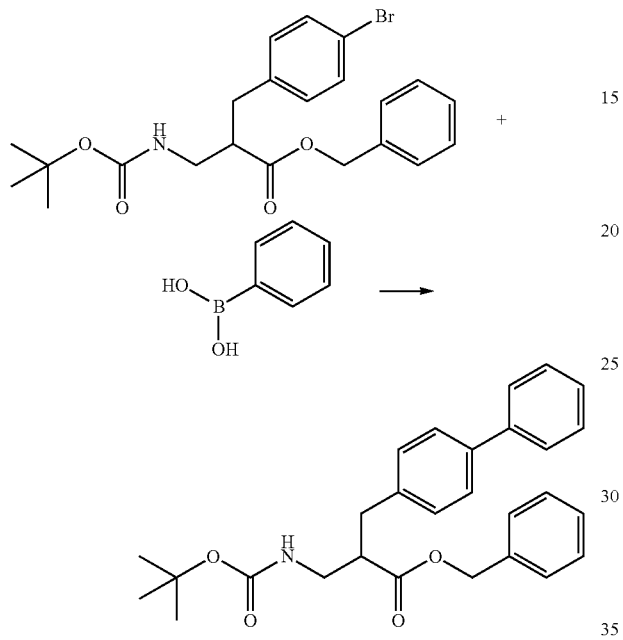

A solution of benzyl 2-(4-bromobenzyl)-3-(tert-butoxycarbonylamino)propanoate (44 mg, 0.098 mmol), phenylboronic acid (17.95 mg, 0.147 mmol), Pd(PPh3)4 (11.34 mg, 9.81 μmol) and 2M aqueous Na₂CO₃ (0.098 ml, 0.196 mmol) in toluene (1 ml) was allowed to stir under nitrogen at 95° C. for 18 hours. The reaction mixture was cooled to room temperature, and extracted with EtOAc. The combined organic layer was washed with brine, dried over MgSO₄, filtered, and concentrated under reduced pressure. The obtained residue was purified by flash column chromatography on silica gel (eluent: heptane/EtOAc=100:0 to 0:100) to give benzyl 3-(biphenyl-4-yl)-2-((tert-butoxycarbonylamino)methyl)propanoate (27.3 mg); Retention time=1.78 minutes (condition B); MS (m+1)=446.1.

Intermediate 13-1

Synthesis of benzyl 2-(4-bromobenzyl)-3-(tert-butoxycarbonylamino)propanoate

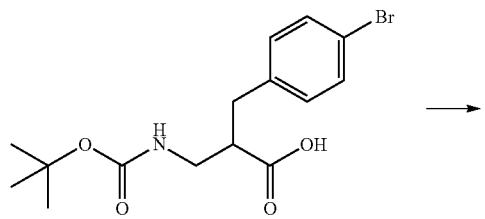

-continued

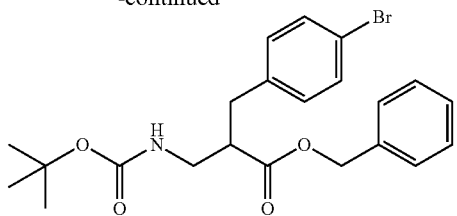

A suspension of 3-(4-bromo-phenyl)-2-(tert-butoxycarbonylamino-methyl)-propionic acid (496 mg, 1.385 mmol), K₂CO₃ (383 mg, 2.77 mmol) and BnBr (0.493 ml, 4.15 mmol) in DMF (3 ml) was allowed to stir under nitrogen for 60 hours. The reaction mixture was cooled, and brine was added. The product was extracted with EtOAc, washed with brine, dried over MgSO₄, filtered, and concentrated under reduced pressure. The residue was purified by flash column chromatography on silica gel (eluent: heptane/EtOAc=100:0 to 50:50) and then purified by RP-HPLC (XBridge Prep Phenyl OBD, H₂O (0.1% NH₄OH)/CH₃CN) to give benzyl 2-(4-bromobenzyl)-3-(tert-butoxycarbonylamino)propanoate (44 mg); Retention time=1.67 minutes (condition B); MS (ES+)= 348.0 (m-Boc+2).

Intermediate 14-1

Synthesis of tert-butyl 2-cyano-3-(3,4-dichlorophenyl)propanoate

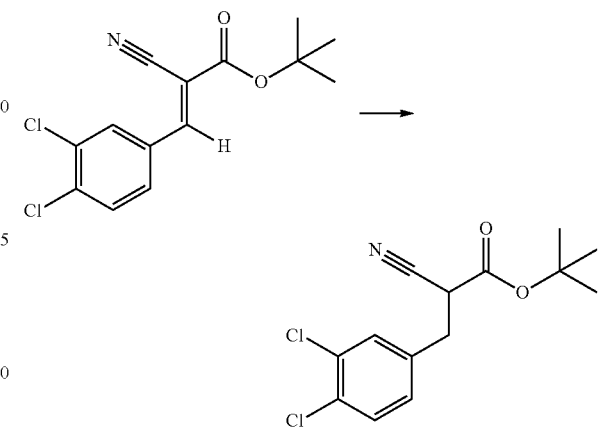

A suspension of (E)-tert-butyl 2-cyano-3-(3,4-dichlorophenyl)acrylate (1.05 g, 3.52 mmol) and zinc (3.45 g, 52.8 mmol) in AcOH (20 ml) was allowed to stir at 100° C. After stirred for 1 hour, the reaction mixture was cooled to ambient temperature, and diluted with toluene and brine. The phases were separated, and the organic layer was washed with brine, dried over Na2SO4, filtered, and concentrated under reduced pressure to give tert-butyl 2-cyano-3-(3,4-dichlorophenyl)propanoate (819 mg); Retention time=1.41 minutes (condition B); MS (ES+)=317.0 (m+18).

Following intermediates were prepared using similar procedure as described in Intermediate 14-1:

| Example # | Product | Condition | HPLC-RT (condition) | MS (M + 1) |
|---|---|---|---|---|
| Intermediate 14-2 | 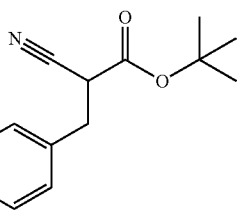<br>tert-butyl 2-cyano-3-(4-methoxyphenyl)propanoate | 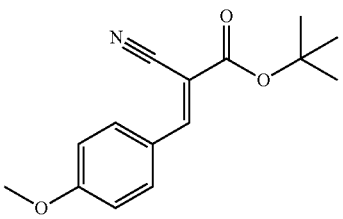<br>Zinc, AcOH, 100° C. | 1.13 min. (A) | 279.2 (m + 18) |

Intermediate 15-1

Synthesis of (E)-tert-butyl 2-cyano-3-(3,4-dichlorophenyl)acrylate

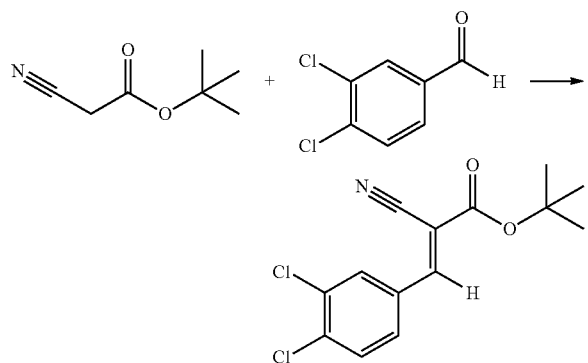

A solution of tert-butyl cyanoacetate (2.52 ml, 17.63 mmol), 3,4-dichlorobenzaldehyde (2.57 g, 14.69 mmol) and piperidine (0.145 ml, 1.469 mmol) in EtOH (50 ml) was allowed to stir at 80° C. for 15 hours, and then cooled to ambient temperature. A half volume of the solvent was evaporated, and 400 ml of water was added to the resulting mixture. The precipitated solid was collected and washed with 5% iPrOH/H$_2$O (200 ml). The solid was dried under reduced pressure to give (E)-tert-butyl 2-cyano-3-(3,4-dichlorophenyl)acrylate (3.577 g); Retention time=1.61 minutes (condition A); MS (ES+)=315.1 (m+18).

Intermediate 16-1

Synthesis of tert-butyl 3-amino-2-(4-methoxybenzyl)propanoate

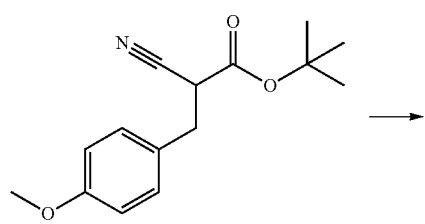

-continued

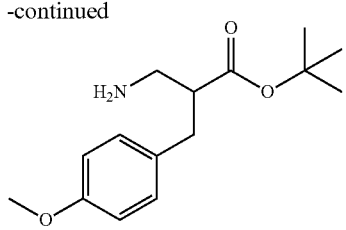

A solution of tert-butyl 2-cyano-3-(4-methoxyphenyl)propanoate (50 mg, 0.191 mmol) in EtOH (4 ml) was hydrogenated with Raney-Cobalt at 50° C. (30 atm) for 2 hours. The reaction mixture was concentrated under reduced pressure to give tert-butyl 3-amino-2-(4-methoxybenzyl)propanoate (50.1 mg); Retention time=1.24 minutes (condition A); MS (m+1)=266.3.

Intermediate 17-1

Synthesis of Methyl 2-(2-tert-butoxy-2-oxoethyl)-2,3-dihydro-1H-indene-2-carboxylate

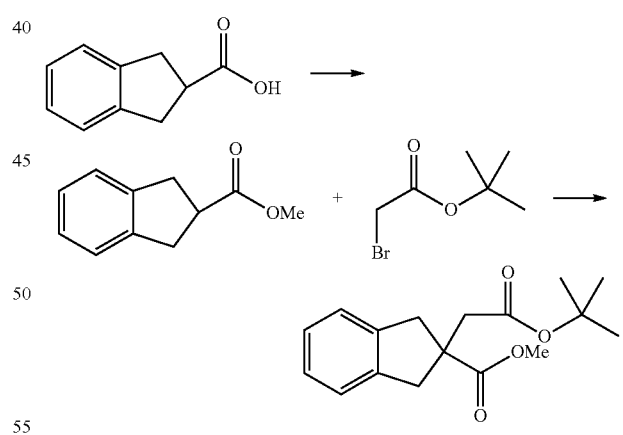

To a solution of indan-2-carboxylic acid (6 g, 37.0 mmol) in MeOH (100 ml) at 0° C. was added 4M HCl/dioxane (9.00 ml, 36.0 mmol) dropwise, and the mixture was stirred at room temperature over 48 hours. The reaction mixture was concentrated to dryness and dissolved in EtOAc, which was washed with sat. NaHCO$_3$ and brine then dried over anhydrous sodium sulfate, filtered and concentrated under reduced pressure. The obtained residue was purified by flash chromatography (silica gel, 5 to 30% EtOAc/HEP) and gave the methyl ester intermediate: 5.1 g (yield: 80%). LCMS (condition D): 177.1 (M+1); retention time=1.54 min.

Next, to a solution of the above methyl ester intermediate (5 g, 28.4 mmol) in THF (100 ml) at −78° C. was added sodium bis(trimethylsilyl)amide (42.6 ml, 42.6 mmol) dropwise over 10 minutes. The mixture was stirred for 15 minutes, then tert-butyl bromoacetate (6.28 ml, 42.6 mmol) was added dropwise over 30 minutes. The resulting mixture was stirred for 30 minutes at −78° C., and then quenched by saturated ammonium chloride at −78° C. The mixture was extracted with EtOAc, and the combined organic layer was washed with brine and dried over anhydrous sodium sulfate, filtered and concentrated under reduced pressure. The obtained residue was purified by flash chromatography (silica gel, EtOAc/HEP) and gave the title compound: 5.4 g (yield: 77%). LCMS (condition B): 291.1 (M+1); retention time=1.42 min.

Intermediate 18-1

Synthesis of 2-(2-Tert-butoxy-2-oxoethyl)-2,3-dihydro-1H-indene-2-carboxylic acid

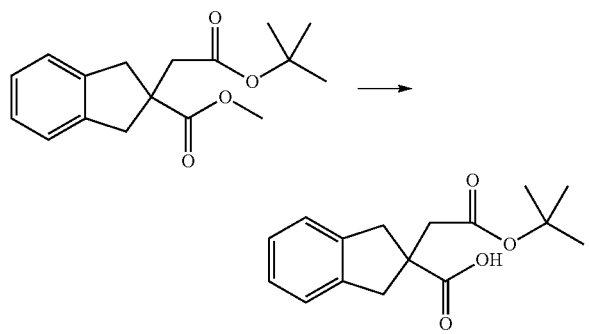

To a solution of methyl 2-(2-tert-butoxy-2-oxoethyl)-2,3-dihydro-1H-indene-2-carboxylate (4.5 g, 15.50 mmol) in EtOH/THF (70 mL, 1:1) at room temperature was added 1 M sodium hydroxide (35 ml, 35.0 mmol), and the mixture was stirred at room temperature for 1.5 hour. To the reaction mixture was added DCM and acidified by 1 M HCl to pH=7. The mixture was extracted with DCM, and the combined organic layer was washed with brine and dried over anhydrous sodium sulfate, filtered and concentrated under reduced pressure. The obtained residue was purified by flash chromatography (silica gel, 10 to 30% EtOAc/HEP) and gave the title compound: 1.4 g (yield: 15%). LCMS (condition B): 275.2 (M−1); retention time=1.17 min.

Intermediate 19-1

Synthesis of (S)-Benzyl 1-((S)-2-(tert-butoxycarbonylamino)-3-phenylpropanoyl)pyrrolidine-2-carboxylate

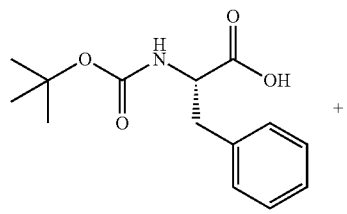

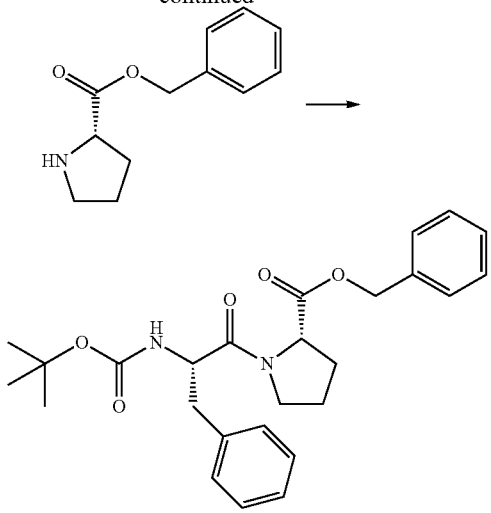

To a suspension of N-Boc-L-phenylalanine (1.000 g, 3.77 mmol) in acetonitrile (25 ml) at room temperature was added L-proline benzyl ester HCl (1.002 g, 4.15 mmol), PyBOP (2.060 g, 3.96 mmol) followed by DIPEA (1.382 ml, 7.92 mmol). The reaction turned to clear and was stirred at room temperature for 1 hour. The reaction was quenched by brine and was extracted with EtOAc. The combined organic layer was washed with brine and dried over anhydrous sodium sulfate, filtered and concentrated under reduced pressure. The obtained residue was purified by flash chromatography (silica gel, 30 to 50% EtOAc/HEP) and gave the title compound: 1.6 g (yield: 97%). LCMS (condition B): 453.4 (M+1); retention time=1.44 min.

Intermediate 20-1

Synthesis of (Z)-Tert-butyl 2-cyano-3-(4-(pyridin-2-yl)phenyl)acrylate

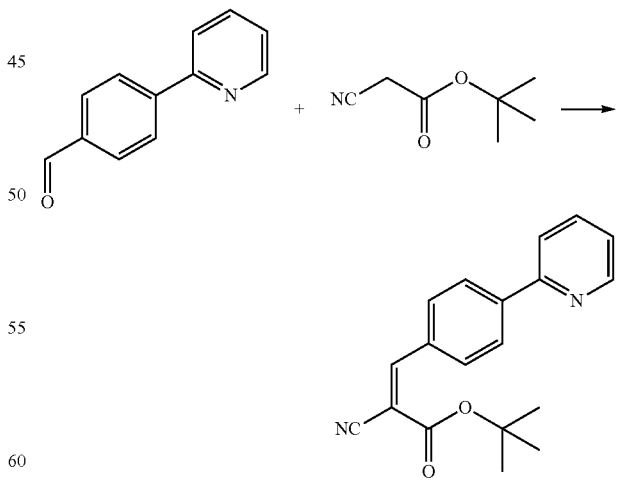

To a solution of 4-(pyridin-2-yl)-benzaldehyde (300 mg, 1.638 mmol) in EtOH (5 ml) at room temperature was added tert-butyl 2-cyanoacetate (0.281 ml, 1.965 mmol) followed by piperidine (0.016 ml, 0.164 mmol). The mixture was stirred at 73° C. overnight. The reaction mixture was cooled to room temperature and concentrated under reduced pressure.

To the obtained mixture was added water and then extracted with DCM. The combined organic layer was washed with brine and dried over anhydrous sodium sulfate, filtered and concentrated under reduced pressure. The obtained residue was purified by flash chromatography (silica gel, 15 to 30% EtOAc/Heptane) and gave the title compound: 350 mg (yield: 70%). LCMS (condition B): 307.2 (M+1); retention time=1.30 min.

Intermediate 21-1

Synthesis of Tert-butyl 2-cyano-3-(4-(pyridin-2-yl) phenyl)propanoate

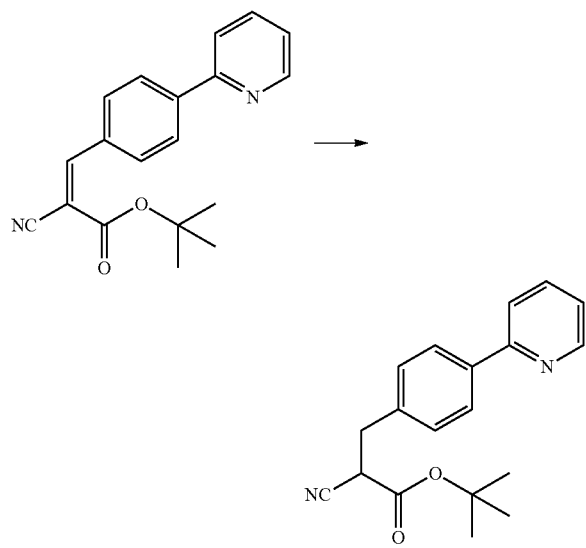

A suspension of (Z)-tert-butyl 2-cyano-3-(4-(pyridin-2-yl) phenyl)acrylate (340 mg, 1.110 mmol) and zinc (1089 mg, 16.65 mmol) in AcOH (6.5 ml) was stirred at 100° C. for 2 hours. The mixture was cooled to room temperature and filtered. To the filtrate was added EtOAc and water, and the mixture was basified by aq. NaOH. The combined organic layer was washed with brine and dried over anhydrous sodium sulfate, filtered and concentrated under reduced pressure. The obtained residue was purified by flash chromatography (silica gel, 15 to 30% EtOAc/Heptane) and gave the title compound: 150 mg (yield: 44%). LCMS (condition B): 309.2 (M+1); retention time=1.09 min.

Intermediate 22-1

Synthesis of Tert-butyl 3-amino-2-(4-(pyridin-2-yl) benzyl)propanoate

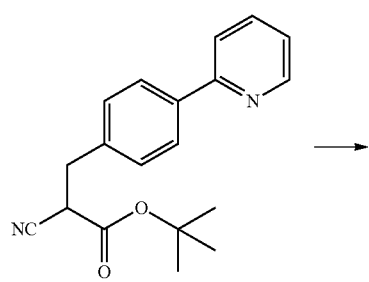

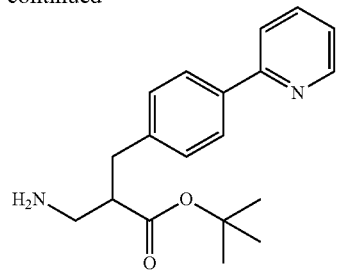

A suspension of tert-butyl 2-cyano-3-(4-(pyridin-2-yl) phenyl)propanoate (150 mg, 0.486 mmol), Raney 2800 nickel (slurry in water) (0.486 mmol), Pd/C (51.8 mg, 0.049 mmol) and ammonium hydroxide (1.894 ml, 48.6 mmol) in dioxane (10 ml) was stirred at room temperature under H$_2$ for 3 hours. The reaction mixture was filtered, and the filtrate was extracted with EtOAc. The combined organic layer was washed with brine and dried over anhydrous sodium sulfate, filtered and concentrated under reduced pressure to give the title compound. LCMS (condition B): 313.3 (M+1); retention time=0.54 min.

Intermediate 23-1

Synthesis of Benzyl 2-(1-(tert-butoxycarbonylamino)cyclopentyl)acetate

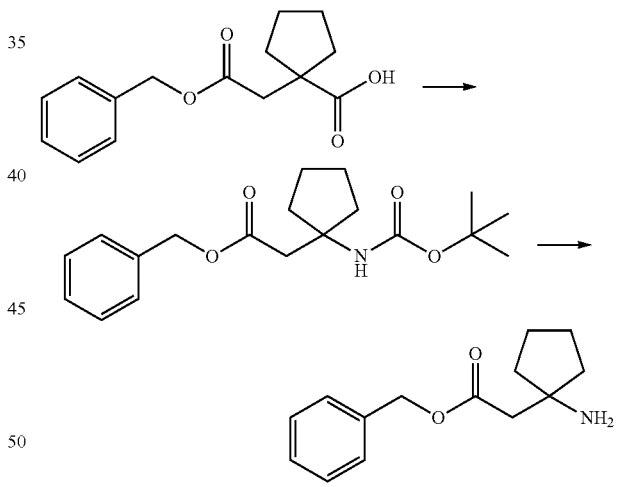

To a solution of 1-(2-(benzyloxy)-2-oxoethyl)cyclopentanecarboxylic acid (500 mg, 1.906 mmol) in t-BuOH (10 ml) at room temperature was added DPPA (0.618 ml, 2.86 mmol) followed by TEA (0.399 ml, 2.86 mmol). The reaction mixture was stirred at 93° C. overnight. The reaction mixture was cooled to room temperature and was extracted with EtOAc. The combined organic layer was washed with sat. NaHCO$_3$, brine and dried over anhydrous sodium sulfate, filtered and concentrated under reduced pressure. The obtained residue was purified by flash chromatography (silica gel, 5 to 25% EtOAc/HEP) and HPLC (50-80% ACN/water (0.1% NH$_4$OH)) by X-Bridge C18 column and gave the title compound: 106 mg (yield: 17%). LCMS (condition B): 334.0 (M+1); retention time=1.44 min.

Intermediate 24-1

Synthesis of Benzyl 2(1-aminocyclopentyl)acetate trifluoroacetate

To a solution of benzyl 2-(1-(tert-butoxycarbonylamino) cyclopentyl)acetate (106 mg, 0.318 mmol) in DCM (10 ml) at room temperature was added TFA (0.490 ml, 6.36 mmol), and the mixture was stirred at room temperature for 4 hours. The mixture was concentrated under reduced pressure to give the title compound. LCMS (condition A): 234.2 (M+1); retention time=1.06 min.

Intermediate 25-1

Synthesis of 2-(Biphenyl-4-ylmethyl)-4-tert-butoxy-4-oxobutanoic acid

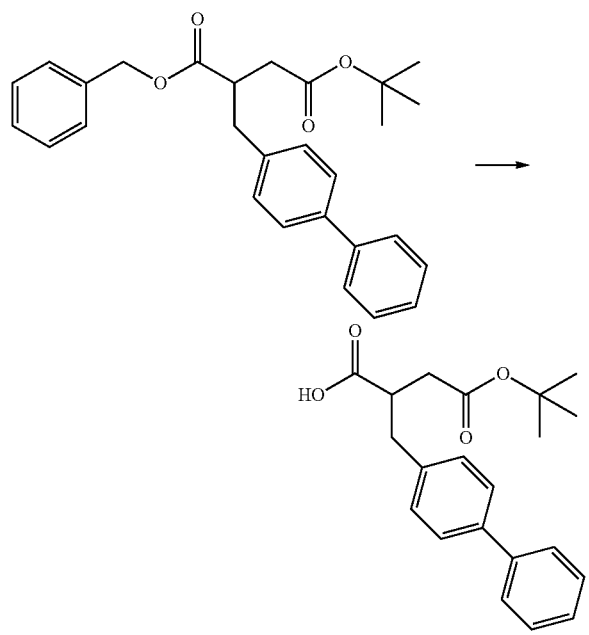

1-Benzyl 4-tert-butyl 2-(biphenyl-4-ylmethyl)succinate (500 mg, 1.161 mmol) was dissolved in 10 mL of EtOAc and hydrogenated with 10% Pd/C at room temperature. After 4 hours of the hydrogenation, the mixture was concentrated under reduced pressure. The obtained residue was purified by flash chromatography (silica gel, 2 to 5% MeOH/DCM) and gave the title compound: 296 mg (yield: 93%). LCMS (condition G): 339.1 (M−1); retention time=0.70 min.

Intermediate 26-1

Synthesis of (S)-2-(Tert-butoxycarbonylamino)-3-(3'-chlorobiphenyl-4-yl)propanoic acid

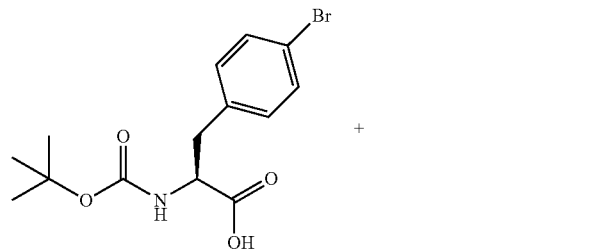

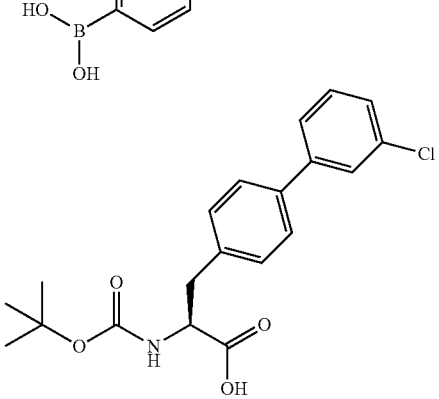

To a solution of Boc-4-bromo-L-phenylalanine (15 g, 43.6 mmol) in DME (180 ml) at room temperature was added 3-chlorobenzeneboronic acid (8.52 g, 54.5 mmol) followed by aq. $Na_2CO_3$ (32.7 ml, 65.4 mmol) and $Pd(PPh_3)_4$ (1.511 g, 1.307 mmol). The mixture was stirred at 85° C. for 3 hours. The reaction mixture was filtered and added EtOAc and acidified by 1M HCl to pH~5. The combined organic layer was washed with brine and dried over anhydrous sodium sulfate, filtered and concentrated under reduced pressure. The obtained residue was purified by flash chromatography (silica gel, 5 to 20% EtOAc/Heptane) and gave the title compound: 12.0 g (yield: 66%). LCMS (condition A): 374.2 (M−1); retention time=1.57 min.

Intermediate 27-1

Synthesis of (S)-Tert-butyl 3-(3'-chlorobiphenyl-4-yl)-1-(2-cyanoethylamino)-1-oxopropan-2-ylcarbamate

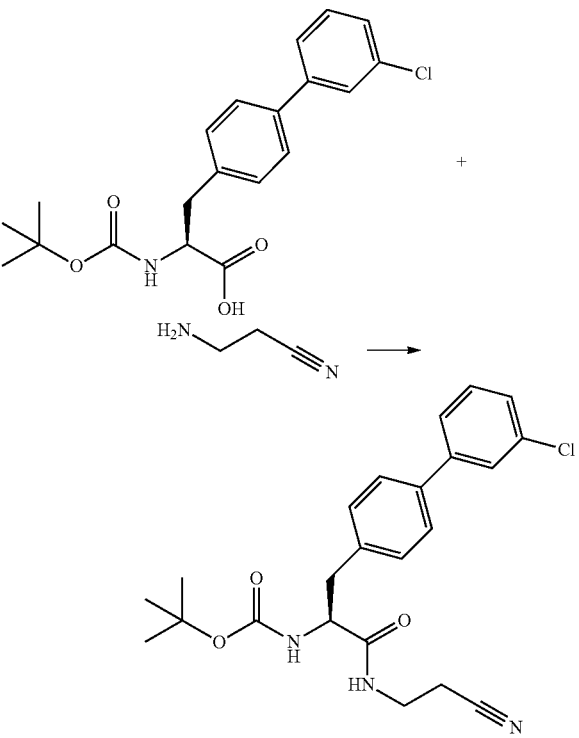

To a solution of (S)-2-(tert-butoxycarbonylamino)-3-(3'-chlorobiphenyl-4-yl)propanoic acid (1 g, 2.66 mmol) in THF (30 ml) at room temperature was added EDC.HCl (1.020 g, 5.32 mmol) and HOBT (0.815 g, 5.32 mmol). The reaction was stirred at room temperature for 10 minutes then was added 3-aminopropionitrile (0.389 ml, 5.32 mmol) and TEA (0.742 ml, 5.32 mmol). The reaction mixture was stirred at room temperature for overnight. The reaction mixture was quenched by brine and was extracted with EtOAc. The combined organic layer was washed with brine and dried over anhydrous sodium sulfate, filtered and concentrated under reduced pressure. The obtained residue was purified by flash chromatography (silica gel, 2 to 4% EtOH/DCM) and gave the title compound: 1.1 g (yield: 97%). LCMS (condition B): 428.2 (M+1); retention time=1.20 min.

Intermediate 28-1

Synthesis of (S)-Tert-butyl 2-(3'-chlorobiphenyl-4-yl)-1-(1-(2-cyanoethyl)-1H-tetrazol-5-yl)ethylcarbamate

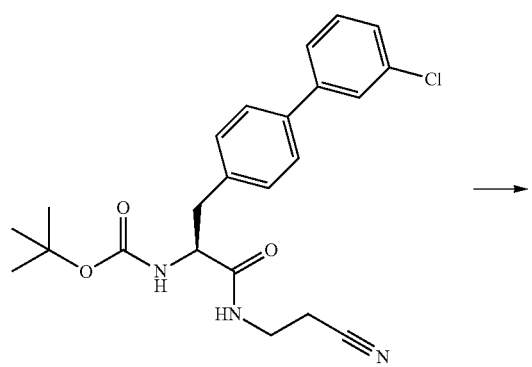

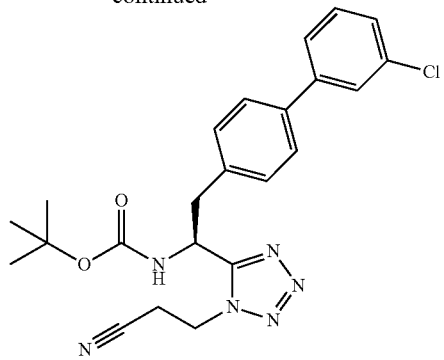

To a solution of (S)-tert-butyl 3-(3'-chlorobiphenyl-4-yl)-1-(2-cyanoethylamino)-1-oxopropan-2-ylcarbamate (1.07 g, 2.500 mmol) in THF (50 ml) at room temperature was added Ph₃P (1.640 g, 6.25 mmol), and the mixture was stirred at room temperature for 10 minutes. Then, to the mixture at 0° C. was added DIAD (1.215 ml, 6.25 mmol) and 2 minutes later was slowly added trimethylsilyl azide (0.828 ml, 6.25 mmol). The resulting light yellow suspension was slowly warmed up to room temperature and stirred overnight. The reaction mixture was concentrated under reduced pressure. The obtained residue was purified by flash chromatography (silica gel, 25 to 50% EtOAc/Heptane) and gave the title compound: 423 mg (yield: 85%). LCMS (condition B): 453.2 (M+1); retention time=1.23 min.

Following intermediates were prepared using similar procedure as described in Intermediate

| Example # | Product | HPLC-RT (condition) | MS (M + 1) |
|---|---|---|---|
| Intermediate 28-2 | {(S)-2-Biphenyl-4-yl-1-[1-(2-cyano-ethyl)-1H-tetrazol-5-yl]-ethyl}-carbamic acid tert-butyl ester | 1.42 min (Condition A) | 319 |

Intermediate 29-1

Synthesis of (S)-Tert-butyl 2-(3'-chlorobiphenyl-4-yl)-1-(1H-tetrazol-5-yl)ethylcarbamate

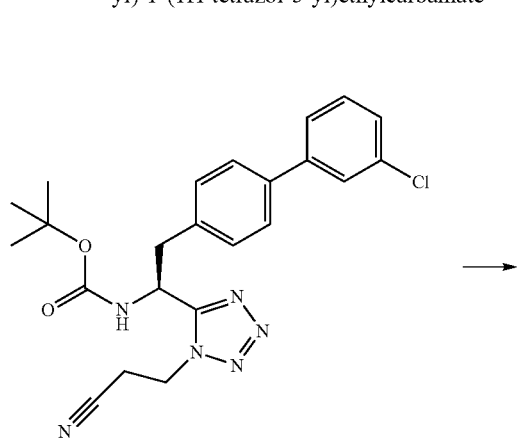

To a suspension of (S)-tert-butyl 2-(3'-chlorobiphenyl-4-yl)-1-(1-(2-cyanoethyl)-1H-tetrazol-5-yl)ethylcarbamate (300 mg, 0.662 mmol) in DCM (3 ml) at room temperature was added DBU (2 ml, 13.27 mmol), and the solution was stirred at room temperature for 1.5 hours. The reaction mixture was concentrated reduced pressure. The obtained residue was purified by reverse phase HPLC [30 to 95% ACN-water (0.1% TFA) over 10 min by Sunfire C18 column] and gave the title compound: 250 mg (yield: 94%). LCMS (condition F): 400.1 (M+1); retention time=1.28 min.

Following intermediates were prepared using similar procedure as described in Intermediate 29-1:

Intermediate 30-1

Synthesis of (S)-2-(3'-Chlorobiphenyl-4-yl)-1-(1H-tetrazol-5-yl)ethanamine

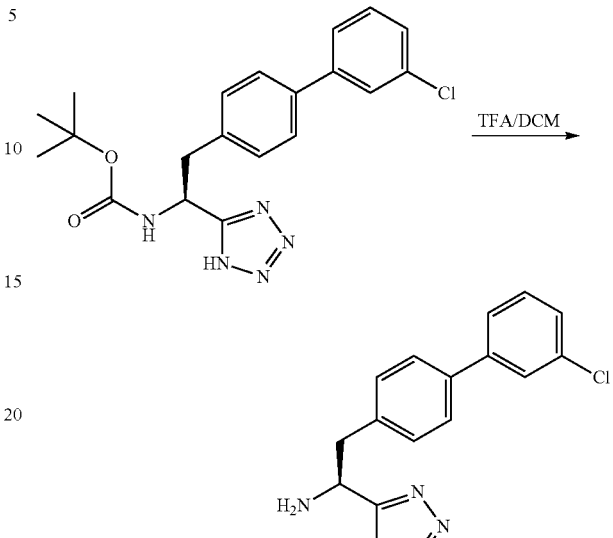

To a solution of (S)-tert-butyl 2-(3'-chlorobiphenyl-4-yl)-1-(1H-tetrazol-5-yl)ethylcarbamate (250 mg, 0.625 mmol) in DCM (5 ml) at room temperature was added TFA (2 ml, 26.0 mmol), and the mixture was stirred at room temperature for 0.5 hour. The mixture was concentrated under reduced pressure and obtained the title compound. LCMS (condition A): 300.1 (M+1); retention time=1.20 min.

Intermediate 31-1

Synthesis of (S)-2-(tert-butoxycarbonylamino)-3-(3'-methylbiphenyl-4-yl)propanoic acid

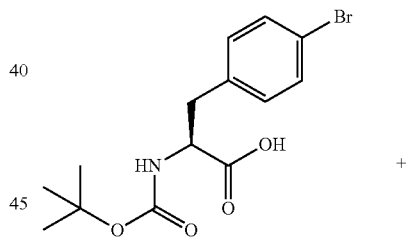

| Example # | Product | Conditions | HPLC-RT (condition) | MS (M + 1) |
|---|---|---|---|---|
| Intermediate 29-2 | [(S)-2-Biphenyl-4-yl-1-(1H-tetrazol-5-yl)-ethyl]-carbamic acid tert-butyl ester | DBU DCM 2 h RT | 1.66 min Condition (A) | 366.0 |

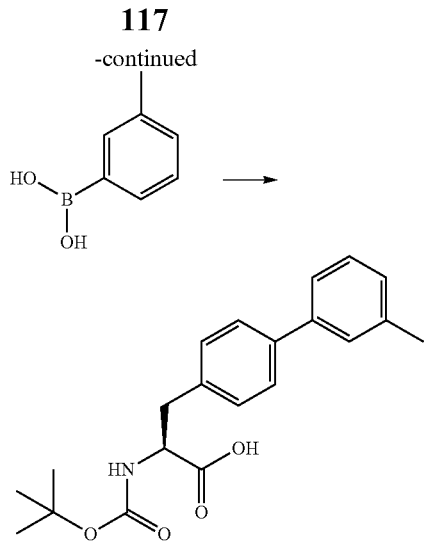

(S)-3-(4-bromophenyl)-2-(tert-butoxycarbonylamino)propanoic acid (2.0 g, 5.81 mmol), 3-methylphenylboronic acid (0.948 g, 6.97 mmol), Pd(PPh$_3$)$_4$ (0.336 g, 0.291 mmol) and 2M NaCO$_3$ aqueous solution (4.36 mL) were stirred in 1,2-dimethoxyethane (30 mL) at 80° C. for 2.5 hours. After being cooled to room temperature, the reaction mixture was diluted with EtOAc and washed with 1M HCl and brine. The organic layer was dried over Na$_2$SO$_4$, concentrated under reduced pressure, and purified by silica gel flash column chromatography (10% MeOH in DCM/DCM) to give(S)-2-(tert-butoxycarbonylamino)-3-(3'-methylbiphenyl-4-yl)propanoic acid. MS: m/z (MH$^+$-Boc) 256. Retention time=1.45 min. (condition A).

Intermediate 32-1

Synthesis of (S)-tert-butyl 1-cyano-2-(3'-methylbiphenyl-4-yl)ethylcarbamate

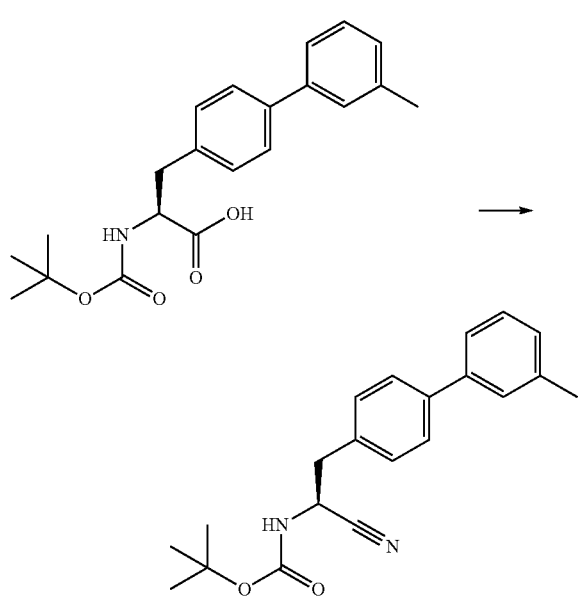

To a solution of (S)-2-(tert-butoxycarbonylamino)-3-(3'-methylbiphenyl-4-yl)propanoic acid (1.37 g, 3.85 mmol) in THF (25 mL) were added ethyl chloroformate (0.407 mL, 4.24 mmol) and triethylamine (0.591 mL, 4.24 mmol) at room temperature. After being stirred for 0.5 hours, the resultant precipitate was removed by filtration. The filtrate was treated with ammonium hydroxide (10 mL) and stirred for 1.5 hours at room temperature. The reaction mixture was diluted with EtOAc and washed with H$_2$O and brine. The organic layer was dried over Na$_2$SO$_4$ and concentrated under reduced pressure. The obtained residue was dissolved in THF (25 mL). TFAA (0.817 mL, 5.81 mmoL) and pyridine (0.935 mL, 11.56 mmol) were added at −10° C. and stirred for 2 hours. The reaction was quenched with saturated NaHCO$_3$ aqueous solution. The mixture was extracted with EtOAc and washed with brine. The organic layer was dried over Na$_2$SO$_4$, concentrated under reduced pressure, and purified by silica gel flash column chromatography (EtOAc/heptane) to give (S)-tert-butyl 1-cyano-2-(3'-methylbiphenyl-4-yl)ethylcarbamate. $^1$H NMR (400 MHz, CDCl$_3$) δ 1.45 (s, 9H), 2.42 (s, 3H), 3.04-3.19 (m, 2H), 4.68-4.94 (m, 2H), 7.17 (d, J=7.58 Hz, 1H), 7.31-7.41 (m, 5H), 7.59 (d, J=8.08 Hz, 2H); MS: m/z (MH$^+$) 337; Retention time=1.60 min. (condition A).

Intermediate 33-1

Synthesis of [(S)-2-(3'-methyl-biphenyl-4-yl)-1-(1H-tetrazol-5-yl)-ethyl]-carbamic acid tert-butyl ester

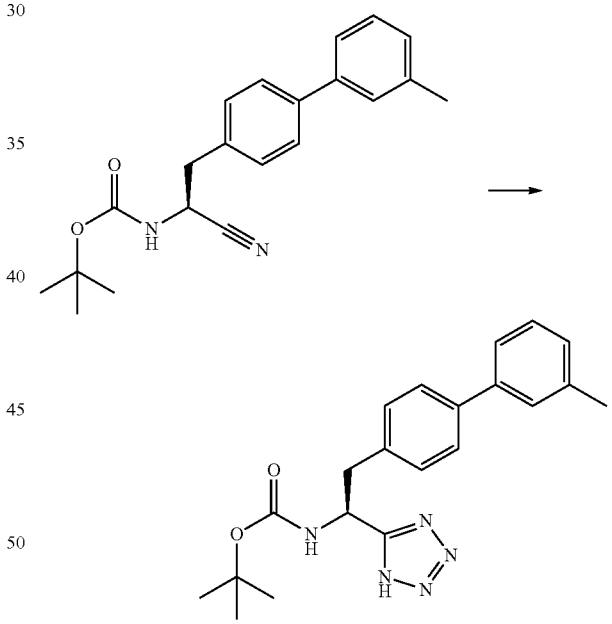

(S)-tert-butyl 1-cyano-2-(3'-methylbiphenyl-4-yl)ethylcarbamate (0.81 g, 2.408 mmol), sodium azide (0.344 g, 5.30 mmol) and zinc bromide (0.325 g, 1.445 mmol) were refluxed in i-propanol (15 mL) and H$_2$O (30 mL) for 6 hours. The reaction mixture was cooled to room temperature, diluted with EtOAc, and washed with 1M HCl and brine. The organic layer was dried over Na$_2$SO$_4$ and concentrated under reduced pressure. The obtained residue was purified by silica gel flash column chromatography (EtOAc/heptane->10% MeOH in DCM/DCM) to give [(S)-2-(3'-methyl-biphenyl-4-yl)-1-(1H-tetrazol-5-yl)-ethyl]-carbamic acid tert-butyl ester. $^1$H NMR (400 MHz, DMSO-d6) δ 1.30 (s, 9H), 2.36 (s, 3H), 3.10-3.21 (m, 1H), 3.24-3.31 (m, 1H), 4.96-5.15 (m, 1H), 7.15 (d, J=7.33 Hz, 1H), 7.27-7.35 (m, 3H), 7.39-7.46 (m, 2H), 7.55 (d, J=8.08 Hz, 2H), 7.65 (d, J=8.34 Hz, 1H); MS: m/z (MH⁺) 380; Retention time=1.51 min. (condition A)

Intermediate 34-1

Synthesis of (S)-2-(3'-methylbiphenyl-4-yl)-1-(1H-tetrazol-5-yl)ethanamine hydrochloride

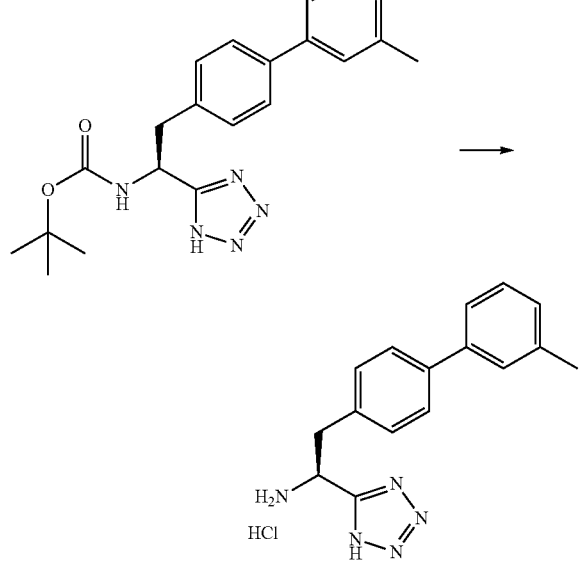

[(S)-2-(3'-Methyl-biphenyl-4-yl)-1-(1H-tetrazol-5-yl)-ethyl]-carbamic acid tert-butyl ester (560 mg, 1.48 mmol) was treated with 4M HCl in dioxane (10 mL) at room temperature for 2 hours. The reaction mixture was concentrated in vacuo to give (S)-2-(3'-methyl-biphenyl-4-yl)-1-(1H-tetrazol-5-yl)-ethylamine hydrochloride; MS: m/z (MH⁺) 280; Retention time=1.14 min. (condition A).

Following intermediates were prepared using similar procedure as described in Intermediate 34-1.

| Example # | Product | HPLC-RT (condition) | MS (M + 1) |
|---|---|---|---|
| Intermediate 34-2 | {(S)-2-Biphenyl-4-yl-1-[1-(2-cyano-ethyl)-1H-tetrazol-5-yl]-ethyl}-carbamic acid tert-butyl ester hydrochloride | 0.98 min. (Condition A) | 296 |

Intermediate 35-1

Synthesis of (S)-tert-butyl 2-(biphenyl-4-yl)-1-(3H-imidazo[4,5-c]pyridin-2-yl)ethylcarbamate

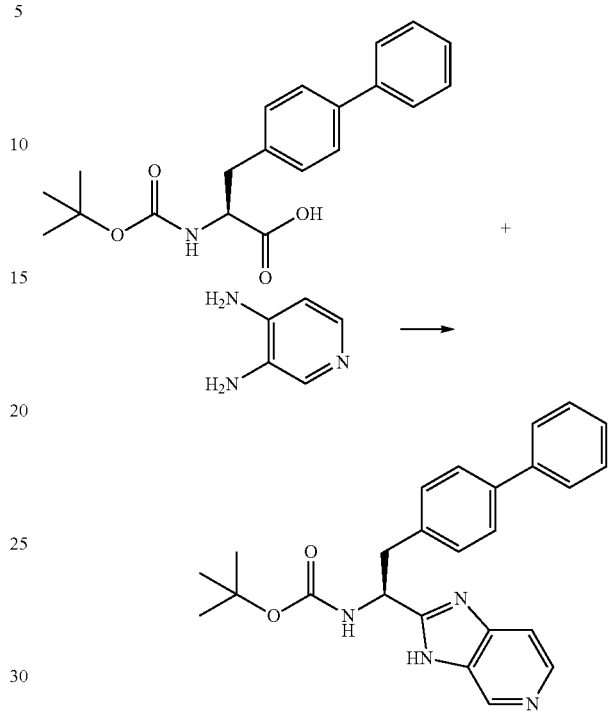

To a solution of (S)-3-(biphenyl-4-yl)-2-(tert-butoxycarbonylamino)propanoic acid (400 mg, 1.172 mmol) in DMF (5 mL) were added BOP (580 mg, 1.289 mmol) and DIPEA (0.246 mL, 1.406 mmol) at room temperature. After being stirred for 10 minutes, pyridine-3,4-diamine (130 mg, 1.230 mmol) was added and stirred for 1 hour. The reaction mixture was diluted with EtOAc and washed with H₂O and brine. The organic layer was dried over Na₂SO₄, concentrated under reduced pressure, and purified by silica gel flash column chromatography (10% MeOH in DCM/DCM). The obtained residue was stirred in acetic acid (5 mL) for 4 hours. The reaction mixture was concentrated and purified by silica gel flash column chromatography to give (S)-tert-butyl 2-(biphenyl-4-yl)-1-(3H-imidazo[4,5-c]pyridin-2-yl)ethylcarbamate; ¹H NMR (400 MHz, CDCl₃) δ 1.41 (s, 9H), 3.33-3.56 (m, 2H), 5.18-5.27 (m, 1H), 5.37-5.48 (m, 1H), 7.22-7.29 (m, 2H), 7.30-7.36 (m, 1H), 7.42 (t, J=7.83 Hz, 2H), 7.48-7.58 (m, 4H), 7.60-7.66 (m, 1H), 8.32 (d, J=5.81 Hz, 1H), 8.94 (s, 1H); MS: m/z (MH⁺) 415.

Intermediate 36-1

Synthesis of methyl 1-(2-chloroallyl)cyclopentanecarboxylate

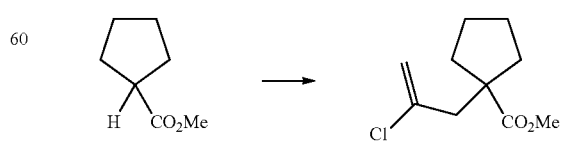

To a solution of methyl cyclopentanecarboxylate (2.0 g, 15.60 mmol) in THF (70 mL) cooled to −78° C. was added 2

M solution of LDA in THF (10.1 mL, 20.3 mmol). The mixture was stirred at −78° C. for 1 hour. To this mixture was added 2,3-dichloroprop-1-ene (3.46 g, 31.2 mmol) and allowed to warm to room temperature. The reaction mixture was quenched with aq. NH₄Cl and extracted with EtOAc. The organic layer was washed with water, brine, dried over MgSO₄, filtered, and concentrated under reduced pressure. The obtained residue was purified by chromatography using EtOAc/heptane gradient to give methyl 1-(2 chloroallyl)cyclopentanecarboxylate (1.82 g). ¹H NMR (400 MHz, CHLOROFORM-d) δ ppm 1.46-1.75 (m, 6H), 1.98-2.18 (m, 2H), 2.66 (s, 2H), 3.61 (s, 3H), 5.02 (d, J=1.3 Hz, 1H), 5.14 (d, J=1.3 Hz, 1H).

Intermediate 37-1

Synthesis of 1-(2-chloroallyl)cyclopentanecarboxylic acid

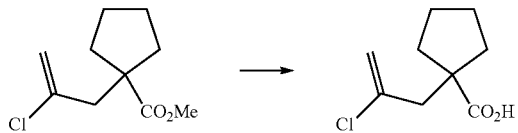

To a solution of methyl 1-(2-chloroallyl)cyclopentanecarboxylate (1.82 g, 8.98 mmol) in MeOH (30 mL) was added 1M NaOH (26.9 mL, 26.9 mmol) at room temperature. The mixture was stirred at room temperature for 2 hour then heated at 60° C. for 24 hours. The reaction mixture was quenched with excess of aq. 1 M HCl. The mixture was extracted with EtOAc, and the organic layer was washed with water, brine, dried over MgSO₄, filtered, and concentrated under reduced pressure. The obtained residue was purified by flash chromatography using 30% EtOAc/heptane to 100% EtOAc to give 1-(2-chloroallyl)cyclopentanecarboxylic acid. ¹H NMR (400 MHz, CHLOROFORM-d) δ ppm 1.43-1.82 (m, 6H), 2.04-2.28 (m, 2H), 2.69 (s, 2H), 5.08 (s, 1H), 5.17 (d, J=1.0 Hz, 1H).

Intermediate 38-1

Synthesis of (S)-tert-butyl 3-(biphenyl-4-yl)-1-(dimethylamino)-1-oxopropan-2-ylcarbamate

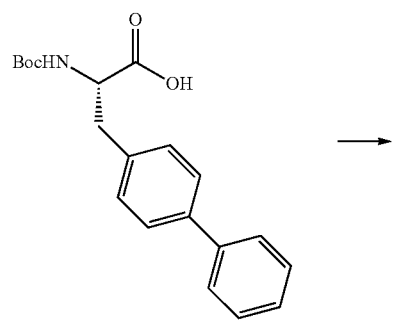

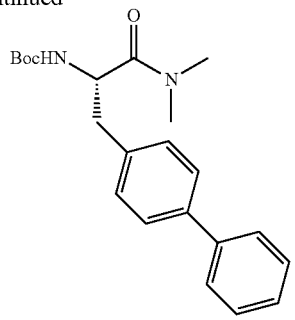

To a solution of (S)-3-(biphenyl-4-yl)-2-(tert-butoxycarbonylamino)propanoic acid (300 mg, 0.88 mmol) in DMF (1.5 mL) and DCM (1.5 mL) was added HATU (401 mg, 1.05 mmol) and triethylamine (0.37 mL, 2.64 mmol). To the mixture at room temperature was added dimethylamine (0.46 mL, 0.91 mmol). The mixture was stirred at room temperature for 2 hours, quenched with sat NaHCO₃, and extracted with EtOAc. The organic layer was washed with water (8 times), brine, dried over MgSO₄, filtered, and concentrated under reduced pressure. The obtained residue was purified by TLC preparation plates using 5% 2M Ammonia in MeOH and DCM to give (S)-tert-butyl 3-(biphenyl-4-yl)-1-(dimethylamino)-1-oxopropan-2-ylcarbamate (196 mg). HPLC retention time=1.66 minutes (condition B); MS (m+1)=369.1; ¹H NMR (400 MHz, CHLOROFORM-d) δ ppm 1.37 (s, 9H) 2.65 (s, 3H) 2.83 (s, 3H) 2.96 (d, J=7.1 Hz, 2H) 4.71-4.94 (m, 1H) 5.56 (d, J=8.6 Hz, 1H) 7.22 (d, J=8.1 Hz, 2H) 7.27 (t, J=7.5 Hz, 1H) 7.37 (t, J=7.6 Hz, 2H) 7.47 (d, J=8.1 Hz, 2H) 7.52 (d, J=7.3 Hz, 2H).

Intermediate 39-1

Synthesis of (S)-2-amino-3-(biphenyl-4-yl)-N,N-dimethylpropanamide

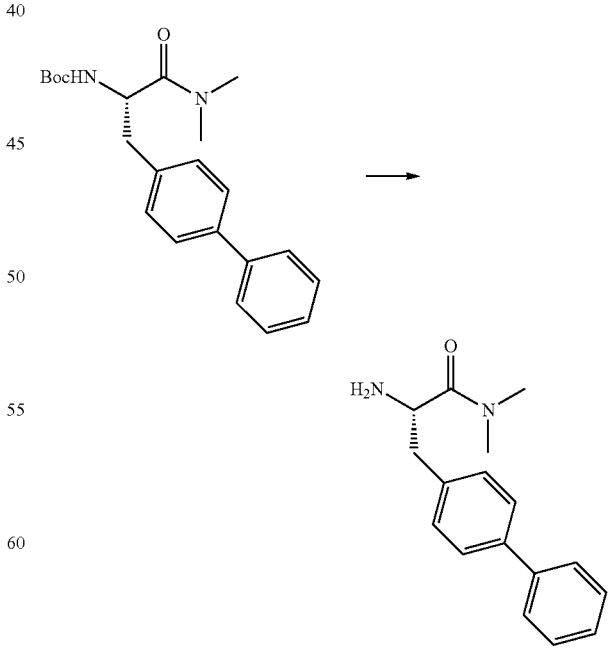

To a solution of (3)-tert-butyl 3-(biphenyl-4-yl)-1-(dimethylamino)-1-oxopropan-2-ylcarbamate (200 mg, 0.54 mmol) in DCM (4 mL) was added TFA (2 mL). The mixture was stirred at room temperature for 2 hours. The mixture was concentrated and azeotroped three times with toluene and dried under high vacuum. The crude (S)-2-amino-3-(biphenyl-4-yl)-N,N-dimethylpropanamide TFA salt (146 mg) was used as is without further purification. HPLC retention time=1.22 minutes (condition B); MS (m+1)=269.2.

Intermediate 40-1

Synthesis of (S)—N-(3-(biphenyl-4-yl)-1-(dimethylamino)-1-oxopropan-2-yl)-1-(2-chloroallyl)cyclopentanecarboxamide

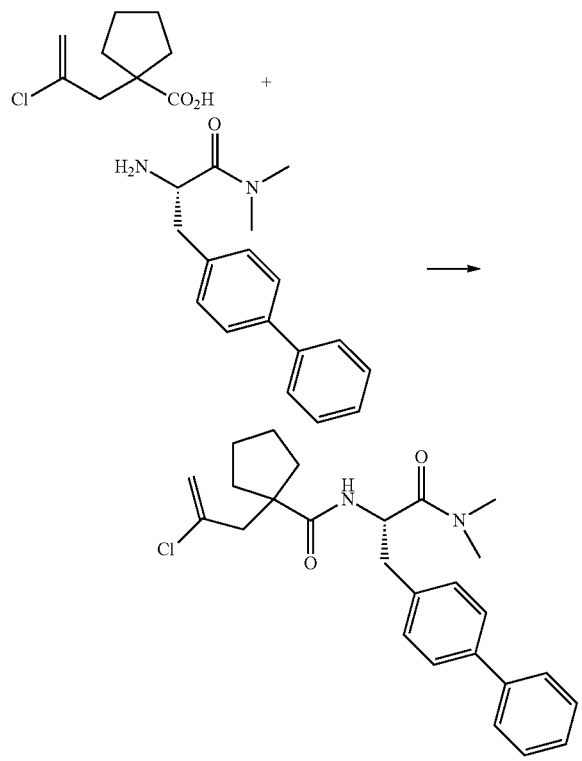

To a solution of 1-(2-chloroallyl)cyclopentanecarboxylic acid (51 mg, 0.27 mmol) in DMF (1 mL) and CH$_2$Cl$_2$ (2 mL) was added (S)-2-amino-3-(biphenyl-4-yl)-N,N-dimethylpropanamide TFA salt (109 mg, 0.41 mmol) and TEA (0.19 mL, 1.35 mmol). To the mixture at room temperature was added HATU (154 mg, 0.41 mmol) and stirred at room temperature for 47 hours. The mixture was quenched with saturated NaHCO$_3$ and extracted with EtOAc. The organic layer was washed with brine, dried over MgSO$_4$, filtered, and concentrated under reduced pressure. The obtained residue was purified by TLC preparation plates using 70% EtOAc/heptane to give (S)—N-(3-(biphenyl-4-yl)-1-(dimethylamino)-1-oxopropan-2-yl)-1-(2-chloroallyl)cyclopentanecarboxamide (83 mg). HPLC retention time=1.76 minutes (condition B); MS (m+1)=439.1; $^1$H NMR (400 MHz, DMSO-d$_6$) δ ppm 1.38-1.66 (m, 5H), 1.89-2.05 (m, 3H), 2.64 (d, J=15.3 Hz, 1H), 2.70 (d, J=15.3 Hz, 1H), 2.85 (s, 3H), 2.95 (s, 3H), 2.95 (dd, J=13.6, 6.1 Hz, 1H), 3.05 (dd, J=13.6, 6.1 Hz, 1H), 5.05 (s, 1H), 5.10 (s, 1H), 5.08-5.13 (m, 1H), 6.70 (d, J=8.1 Hz, 1H), 7.29 (d, J=8.1 Hz, 2H), 7.32-7.38 (m, 1H), 7.44 (t, J=7.7 Hz, 2H), 7.54 (d, J=8.1 Hz, 2H), 7.58-7.65 (m, 2H).

Intermediate 41-1

Synthesis of (S)-tert-butyl 3-(biphenyl-4-yl)-1-(methylamino)-1-oxopropan-2-ylcarbamate

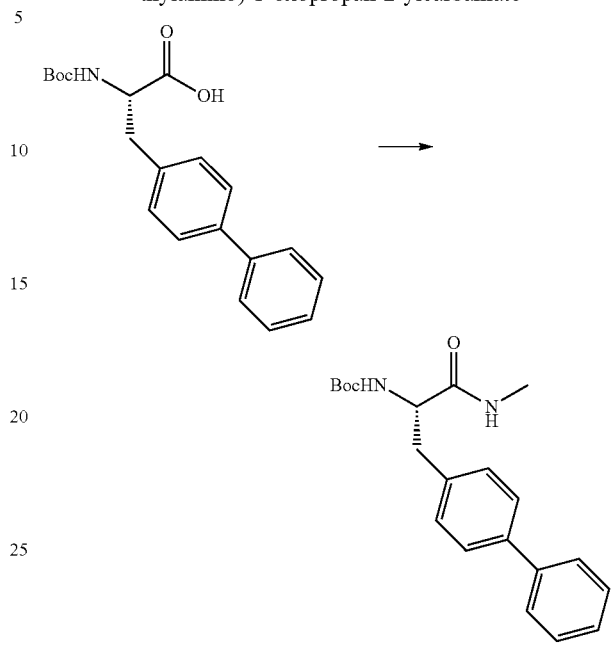

To a solution of (S)-3-(biphenyl-4-yl)-2-(tert-butoxycarbonylamino)propanoic acid (300 mg, 0.88 mmol) in DMF (1.5 mL) and DCM (1.5 mL) was added HATU (401 mg, 1.05 mmol) and triethylamine (0.37 mL, 2.64 mmol) followed by methylamine (0.46 mL, 0.91 mmol). The mixture was stirred at room temperature for 2 hours. The reaction mixture was quenched with sat NaHCO$_3$ and extracted with EtOAc. The organic layer was washed with water (8 times), brine, dried over MgSO$_4$, filtered, and concentrated under reduced pressure. The obtained residue was purified by TLC preparation plates using 3% 2N Ammonia in MeOH in DCM to give (S)-tert-butyl 3-(biphenyl-4-yl)-1-(methylamino)-1-oxopropan-2-ylcarbamate (111 mg). HPLC retention time=1.66 minutes (condition B); MS (m+1)=355.1; $^1$H NMR (400 MHz, CHLOROFORM-d) δ ppm 1.32 (s, 9H) 2.66 (d, J=4.8 Hz, 3H) 3.01 (d, J=6.3 Hz, 2H) 4.18-4.41 (m, 1H) 5.08 (br. s., 1H) 5.93 (d, J=4.3 Hz, 1H) 7.19 (d, J=8.1 Hz, 2H) 7.22-7.29 (m, 1H) 7.35 (t, J=7.6 Hz, 2H) 7.44 (d, J=8.1 Hz, 2H) 7.48 (d, J=7.3 Hz, 2H).

Intermediate 42-1

Synthesis of (S)-2-amino-3-(biphenyl-4-yl)-N-methylpropanamide

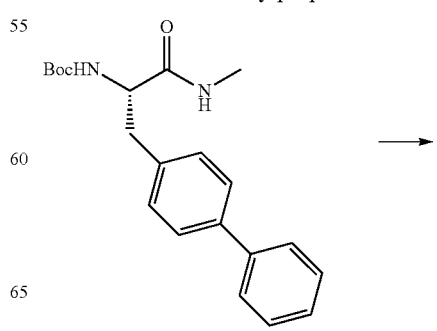

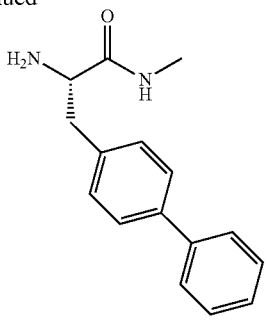

To a solution of (S)-tert-butyl 3-(biphenyl-4-yl)-1-(methylamino)-1-oxopropan-2-ylcarbamate (111 mg, 0.31 mmol) in DCM (4 mL) was added TFA (2 mL). The mixture was stirred at room temperature for 2 hours. The reaction mixture was concentrated and azeotroped (three times) with toluene and dried under high vacuum. The obtained (S)-2-amino-3-(biphenyl-4-yl)-N,N-methylpropanamide TFA salt (80 mg) was used for next step without further purification. HPLC retention time=1.21 minutes (condition B); MS (m+1)=255.0; $^1$H NMR (400 MHz, CHLOROFORM-d) δ ppm 2.48 (d, J=1.8 Hz, 3H) 2.90-3.24 (m, 2H) 4.04-4.48 (m, 1H) 7.10 (d, J=8.3 Hz, 2H) 7.20 (d, J=7.3 Hz, 1H) 7.26 (t, J=7.5 Hz, 2H) 7.37 (d, J=7.6 Hz, 4H) 8.16 (br. s., 2H).

Intermediate 43-1

Synthesis of (S)—N-(3-(biphenyl-4-yl)-1-(methylamino)-1-oxopropan-2-yl)-1-(2-chloroallyl)cyclopentanecarboxamide

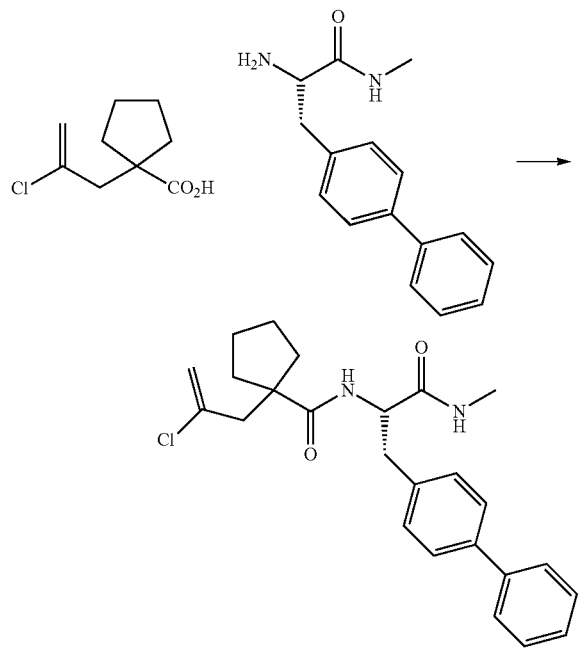

To a solution of 1-(2-chloroallyl)cyclopentanecarboxylic acid (50 mg, 0.27 mmol) in DMF (1.2 mL) was added EDC.HCl (51 mg, 0.27 mmol), HOAt (29 mg, 0.21 mmol) and triethylamine (0.04 mL, 0.27 mmol). To the mixture stirred at room temperature was added (S)-2-amino-3-(biphenyl-4-yl)-N-methylpropanamide TFA salt (45 mg, 0.18 mmol). The mixture was stirred at room temperature for 18 hours. The mixture was extracted with EtOAc, and the organic layer was washed with water (8 times), brine, dried over MgSO$_4$, filtered, and concentrated under reduced pressure. The obtained residue was purified by TLC preparation plates using 70% EtOAc/heptane to give (S)—N-(3-(biphenyl-4-yl)-1-(methylamino)-1-oxopropan-2-yl)-1-(2-chloroallyl)cyclopentanecarboxamide (38 mg). HPLC retention time=1.69 minutes (condition B); MS (m+1)=425.0; $^1$H NMR (400 MHz, CHLOROFORM-d) δ ppm 1.34-1.64 (m, 6H), 1.79-2.02 (m, 2H), 2.59 (d, J=5.8 Hz, 2H), 2.66 (d, J=4.9 Hz, 3H), 3.05 (d, J=7.3 Hz, 2H), 4.66 (q, J=7.5 Hz, 1H), 4.95 (s, 1H), 5.05 (s, 1H), 6.28-6.35 (m, 1H), 6.37 (d, J=7.7 Hz, 1H), 7.20 (d, J=8.2 Hz, 2H), 7.23-7.30 (m, 1H), 7.34 (t, J=7.5 Hz, 2H), 7.45 (dd, J=14.5, 7.8 Hz, 4H).

Intermediate 44-1

Synthesis of (S)-tert-butyl 3-(biphenyl-4-yl)-1-((furan-2-ylmethyl)(methyl)amino)-1-oxopropan-2-ylcarbamate

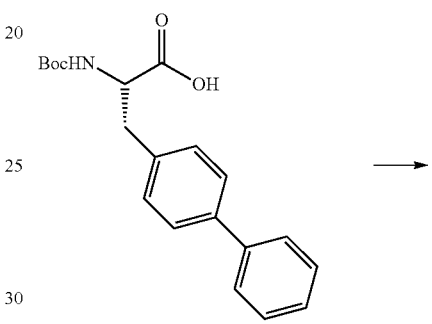

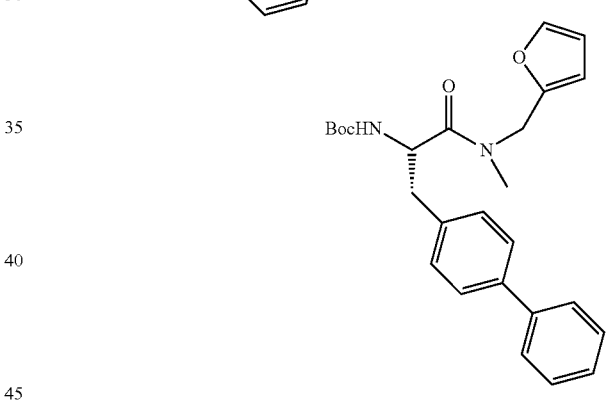

To a solution of 1-(furan-2-yl)-N-methylmethanamine (195 mg, 1.76 mmol), (S)-3-(biphenyl-4-yl)-2-(tert-butoxycarbonylamino)propanoic acid (500 mg, 1.45 mmol), in CH$_2$Cl$_2$ (3 mL) and DMF (3 mL) was added TEA (0.61 mL, 4.39 mmol) and HATU (724 mg, 1.90 mmol). The mixture was stirred at room temperature for 1 hour. The mixture was quenched with aq. NaHCO$_3$ and extracted with EtOAc. The organic layer was washed with aq. NaHCO$_3$, water, and brine. The organic layer was dried over MgSO$_4$, filtered and concentrated under reduced pressure. The obtained residue was purified by silica gel chromatography using 30%-EtOAc/heptane to 90% EtOAc/heptane to give (S)-tert-butyl 3-(biphenyl-4-yl)-1-((furan-2-ylmethyl)(methyl)amino)-1-oxopropan-2-ylcarbamate (614 mg). HPLC retention time=1.80 minutes (condition B); MS (m+1)=435.1; $^1$H NMR (400 MHz, CHLOROFORM-d) δ ppm 1.31 (s, 9H, minor rotamer), 1.34 (s, 9H, major rotamer), 2.61 (s, 3H, major rotamer), 2.83 (s, 3H, minor rotamer), 2.87-2.98 (m, 4H), 4.15-4.32 (m, 2H, minor rotamer), 4.20 (d, J=15.1 Hz, 1H, major rotamer), 4.62 (d, J=15.1 Hz, 1H, major rotamer), 4.77 (q, J=7.3 Hz, 1H, major rotamer), 4.95 (q, J=7.3 Hz, 1H, minor rotamer), 5.30 (d, J=8.6 Hz, 1H, minor rotamer), 5.39 (d, J=8.6 Hz, 1H, major rotamer), 6.05 (d, J=2.8 Hz, 1H, minor rotamer), 6.10 (d, J=2.8 Hz, 1H, major rotamer), 6.18 (br. s., 1H, minor rotamer), 6.23 (dd, J=3.2, 1.9 Hz, 1H, major rotamer), 7.10-7.50 (m, 18H).

Intermediate 45-1

Synthesis of (S)-2-amino-3-(biphenyl-4-yl)-N-(furan-2-ylmethyl)-N-methylpropanamide

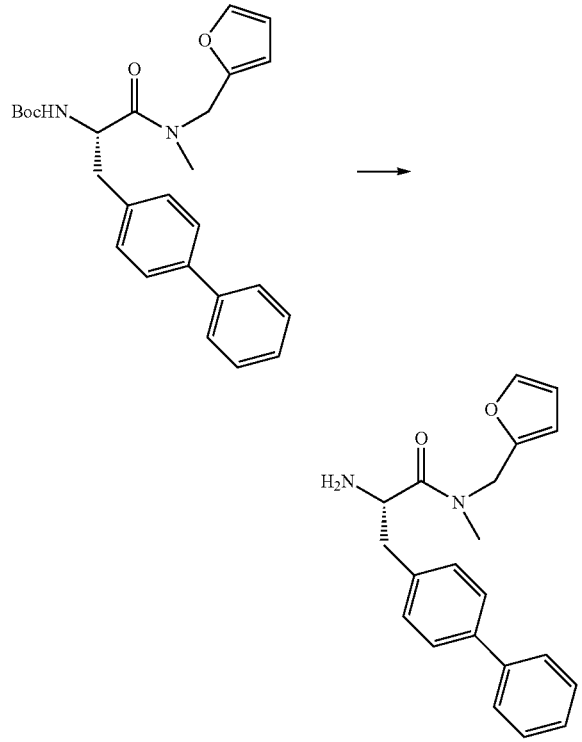

To a solution of (S)-tert-butyl 3-(biphenyl-4-yl)-1-((furan-2-ylmethyl)(methyl)amino)-1-oxopropan-2-ylcarbamate (614 mg) in CH$_2$Cl$_2$ (6 mL) was added TFA (3 mL). The mixture was stirred at room temperature for 2 hours. The mixture was concentrated under reduced pressure and azeotroped (three times) with toluene and dried under high vacuum. The crude (S)-2-amino-3-(biphenyl-4-yl)-N-(furan-2-ylmethyl)-N-methylpropanamide TFA salt (721 mg) was used for next step without further purification. HPLC retention time=1.37 minutes (condition B); MS (m+1)=335.0.

Intermediate 46-1

Synthesis of (S)—N-(3-(biphenyl-4-yl)-1-((furan-2-ylmethyl)(methyl)amino)-1-oxopropan-2-yl)-1-(2-chloroallyl)cyclopentanecarboxamide

 +

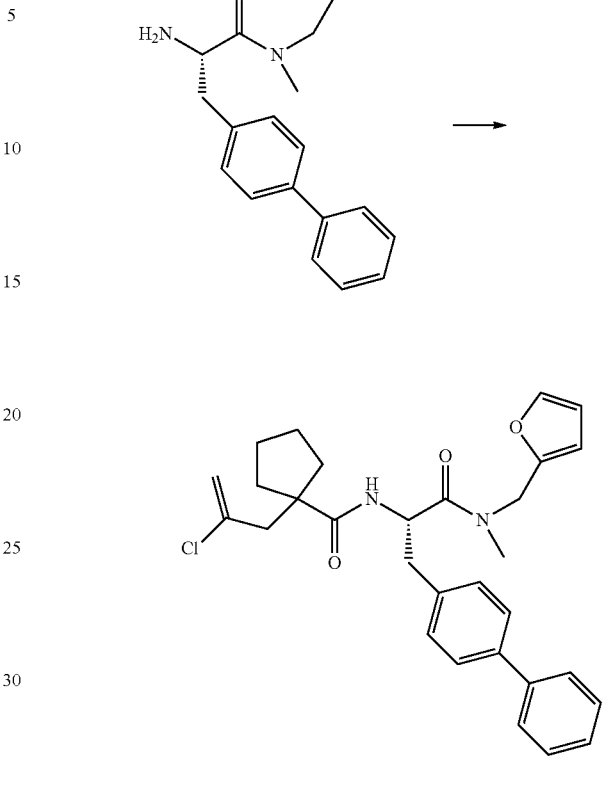

To a solution of 1-(2-chloroallyl)cyclopentanecarboxylic acid (80 mg, 0.42 mmol) in CH$_2$Cl$_2$ (3 mL) and DMF (3 mL) with (S)-2-amino-3-(biphenyl-4-yl)-N-(furan-2-ylmethyl)-N-methylpropanamide TFA salt (199 mg, 0.59 mmol) was added TEA (0.41 mL, 2.97 mmol) and HATU (161 mg, 0.42 mmol). The mixture was stirred at room temperature for 1 hour. The mixture was quenched with aq. NaHCO$_3$ and extracted with EtOAc. The organic layer was washed with water (seven times), brine, dried over MgSO$_4$, filtered, and concentrated under reduced pressure. The obtained residue was purified by silica gel chromatography using 10% EtOAc/heptane to 100% EtOAc/heptane to give (S)—N-(3-(biphenyl-4-yl)-1-((furan-2-ylmethyl)(methyl)amino)-1-oxopropan-2-yl)-1-(2-chloroallyl)cyclopentanecarboxamide (151 mg). HPLC retention time=1.89 minutes (condition B); MS (m+1)=505.3. $^1$H NMR (400 MHz, CHLOROFORM-d) δ ppm 1.61-1.80 (m, 12H), 1.96-2.19 (m, 4H), 2.54-2.83 (m, 6H), 2.74 (s, 3H, major rotamer), 2.95 (s, 3H, minor rotamer), 2.01-3.13 (m, 2H), 4.23 (d, J=16.7 Hz, 1H, minor rotamer), 4.28 (d, J=15.2 Hz, 1H, major rotamer), 4.44 (d, J=16.7 Hz, 1H, minor rotamer), 4.77 (d, J=15.2 Hz, 1H, major rotamer), 5.06 (s, 1H, minor rotamer), 5.12 (d, J=1.3 Hz, 1H, major rotamer), 5.15 (d, J=1.3 Hz, 1H, minor rotamer), 5.19 (d, J=1.3 Hz, 1H, major rotamer), 5.17-5.28 (m, 1H, major rotamer), 5.39 (q, J=7.2 Hz, 1H, minor rotamer), 6.17 (d, J=2.8 Hz, 1H, minor rotamer), 6.24 (d, J=3.3 Hz, 1H, major rotamer), 6.30 (dd, J=3.3, 1.8 Hz, 1H, minor rotamer), 6.37 (dd, J=3.2, 1.9 Hz, 1H, major rotamer), 6.57 (d, J=8.1 Hz, 1H, minor rotamer), 6.68 (d, J=7.8 Hz, 1H, major rotamer), 7.21-7.65 (m, 18H).

Intermediate 47-1

Synthesis of (S)-tert-butyl 2-(biphenyl-4-yl)-1-(1-methyl-1H-tetrazol-5-yl)ethylcarbamate and (S)-tert-butyl 2-(biphenyl-4-yl)-1-(2-methyl-2H-tetrazol-5-yl)ethylcarbamate

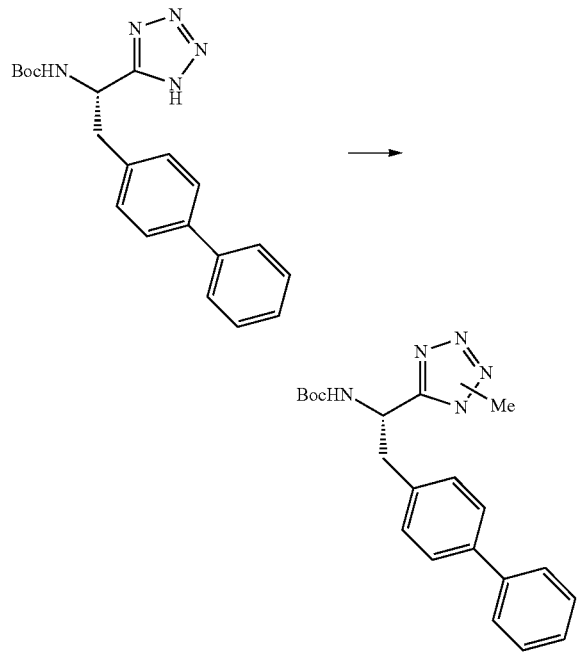

To a solution of (S)-tert-butyl 2-(biphenyl-4-yl)-1-(1H-tetrazol-5-yl)ethylcarbamate (150 mg, 0.41 mmol) in acetone (16.4 mL) was added Na₂CO₃ (65 mg, 0.62 mmol), and the mixture was stirred at room temperature for 5 minutes. Iodomethane (0.03 mL, 0.45 mmol) was added after 5 minutes and the mixture was stirred at room temperature for 18 hours. The reaction mixture was concentrated under reduced pressure and diluted with DCM and water. The water layer was extracted three times with DCM. The combined organic layer was dried over MgSO₄, filtered, and concentrated under reduced pressure. The obtained residue was purified by silica gel chromatography using 100% DCM to 10% MeOH in DCM to give a mixture of (S)-tert-butyl 2-(biphenyl-4-yl)-1-(1-methyl-1H-tetrazol-5-yl)ethylcarbamate and (S)-tert-butyl 2-(biphenyl-4-yl)-1-(2-methyl-2H-tetrazol-5-yl)ethylcarbamate (156 mg). HPLC retention time=1.76 minutes (condition B); MS (m+1)=380.0.

Intermediate 48-1

Synthesis of (S)-2-(biphenyl-4-yl)-1-(1-methyl-1H-tetrazol-5-yl)ethanamine and (S)-2-(biphenyl-4-yl)-1-(2-methyl-2H-tetrazol-5-yl)ethanamine

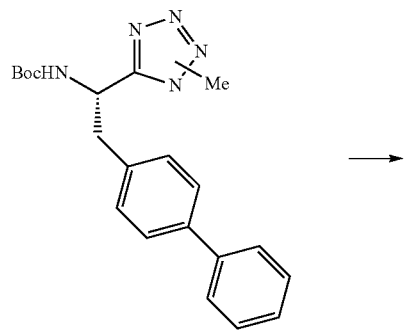

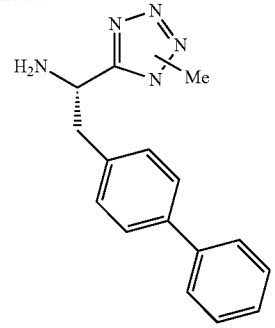

To a solution of (S)-tert-butyl 2-(biphenyl-4-yl)-1-(1-methyl-1H-tetrazol-5-yl)ethylcarbamate and (S)-tert-butyl 2-(biphenyl-4-yl)-1-(2-methyl-2H-tetrazol-5-yl)ethylcarbamate (156 mg, 0.41 mmol) in DCM (4 mL) was added TFA (2 mL). The mixture was stirred at room temperature for 2 hours. The mixture was concentrated and azeotroped three times with toluene and dried under high vacuum. The mixture of (S)-2-(biphenyl-4-yl)-1-(1-methyl-1H-tetrazol-5-yl)ethanamine TFA salt and (S)-2-(biphenyl-4-yl)-1-(2-methyl-2H-tetrazol-5-yl)ethanamine TFA salt (115 mg) was used for next step without further purification. HPLC retention time=1.43 minutes (condition B); MS (m+1)=280.0.

Intermediate 49-1

Synthesis of (S)—N-(2-(biphenyl-4-yl)-1-(1-methyl-1H-tetrazol-5-yl)ethyl)-1-(2-chloroallyl)cyclopentanecarboxamide and (S)—N-(2-(biphenyl-4-yl)-1-(2-methyl-2H-tetrazol-5-yl)ethyl)-1-(2-chloroallyl)cyclopentanecarboxamide

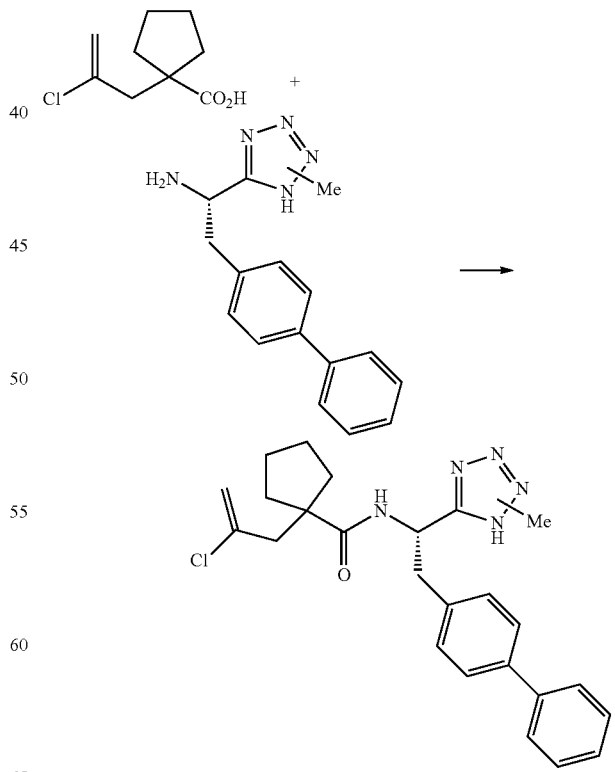

To a solution of 1-(2-chloroallyl)cyclopentanecarboxylic acid (85 mg, 0.45 mmol) in DMF (1.7 mL) and DCM (3.4 mL) was added HATU (257 mg, 0.68 mmol) and triethylamine (0.31 mL, 2.25 mmol). To the mixture stirred at room temperature was added (S)-2-(biphenyl-4-yl)-1-(1-methyl-1H-tetrazol-5-yl)ethanamine TFA salt and (S)-2-(biphenyl-4-yl)-1-(2-methyl-2H-tetrazol-5-yl)ethanamine TFA salt (151 mg, 0.54 mmol). The mixture was stirred at room temperature for 2 hours. The reaction mixture was quenched with sat NaHCO$_3$ and extracted with EtOAc. The organic layer was washed with water (8 times), brine, dried over MgSO$_4$, filtered, and concentrated under reduced pressure. The obtained residue was purified by TLC preparatory plate twice, first using 5% MeOH (2 M NH$_3$) in CH$_2$Cl$_2$ and the second time using 3% MeOH (2M NH$_3$) in CH$_2$Cl$_2$ to give a mixture of (S)—N-(2-(biphenyl-4-yl)-1-(1-methyl-1-tetrazol-5-yl)ethyl)-1-(2-chloroallyl)cyclopentanecarboxamide and (S)—N-(2-(biphenyl-4-yl)-1-(2-methyl-2H-tetrazol-5-yl)ethyl)-1-(2-chloroallyl)cyclopentanecarboxamide (51 mg). HPLC retention time=1.77 minutes (condition B); MS (m+1)=450.2. HPLC retention time=1.79 minutes (condition B), MS (m+1)=450.2. $^1$H NMR (400 MHz, CHLOROFORM-d) δ ppm 1.44-1.68 (m, 12H), 1.84-2.02 (m, 4H), 2.48-2.69 (m, 4H), 3.12-3.27 (m, 2H), 3.33-3.43 (m, 2H), 3.58 (s, 3H), 4.21 (s, 3H), 4.91 (d, J=1.3 Hz, 1H), 4.95 (d, J=1.4 Hz, 1H), 5.01 (d, J=1.4 Hz, 1H), 5.03 (d, J=1.4 Hz, 1H), 5.35-5.51 (m, 1H), 5.56-5.75 (m, 1H), 6.23 (d, J=8.1 Hz, 1H), 6.50 (d, J=8.1 Hz, 1H), 7.00-7.11 (m, 4H), 7.22-7.30 (m, 2H), 7.30-7.43 (m, 8H), 7.43-7.53 (m, 4H).

Intermediate 50-1

(S)-3-(5-(1-amino-2-(biphenyl-4-yl)ethyl)-1H-tetrazol-1-yl)propanenitrile

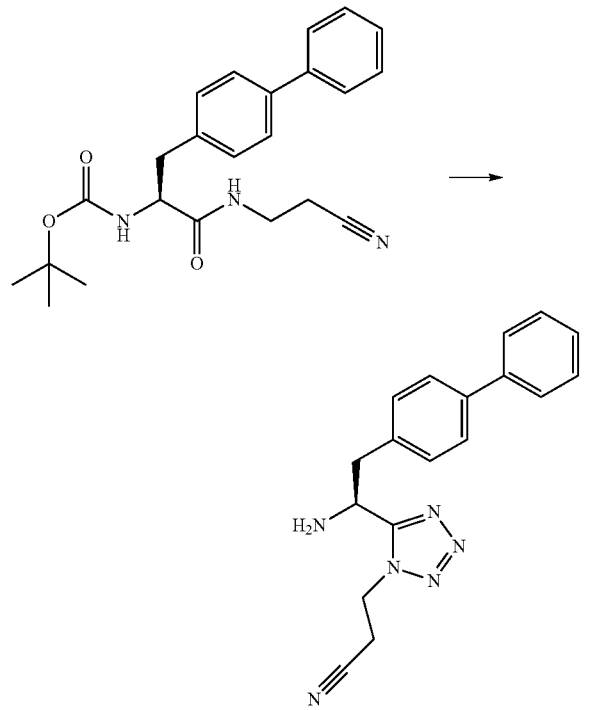

To a solution of (S)-tert-butyl 3-(biphenyl-4-yl)-1-(2-cyanoethylamino)-1-oxopropan-2-ylcarbamate (563 mg, 1.431 mmol) and triphenylphosphine (450 mg, 1.717 mmol) in THF (10 mL) were added DIAD (0.334 mL, 1.717 mmol) and TMSN$_3$ (0.228 mL, 1.717 mmol) at room temperature. After 2 hours, additional triphenylphosphine (180 mg, 0.687 mmol), DIAD (0.134 mL, 0.687 mmol) and TMSN$_3$ (0.0912 mL, 0.687 mmol) were added. After being stirred overnight, additional triphenylphosphine (180 mg, 0.687 mmol), DIAD (0.134 mL, 0.687 mmol) and TMSN$_3$ (0.0912 mL, 0.687 mmol) were added. After being additional 3 hours, the reaction mixture was concentrated and purified by silica gel flash column chromatography (eluent; EtOAc/heptane). The obtained product was treated with 4M HCl in dioxane (10 mL) at room temperature. After being stirred for 1 hour, the reaction mixture was concentrated. The residue was diluted with EtOAc, washed with saturated NaHCO$_3$aq and brine. The organic layer was dried over Na$_2$SO$_4$, concentrated and purified by silica gel flash column chromatography (eluent; MeOH/DCM) to give (S)-3-(5-(1-amino-2-(biphenyl-4-yl)ethyl)-1H-tetrazol-1-yl)propanenitrile (334 mg). $^1$H NMR (400 MHz, CHLOROFORM-d) δ ppm 2.83 (dt, J=6.82, 16.9 Hz, 1H), 2.96 (dt, J=6.82, 13.89 Hz, 1H), 3.21 (dd, J=8.08, 13.64 Hz, 1H), 3.42 (dd, J=6.06, 13.64 Hz, 1H), 4.47-4.59 (m, 2H), 4.60-4.68 (m, 1H), 7.21 (d, J=8.08 Hz, 2H), 7.33-7.39 (m, 1H), 7.42-7.48 (bt, 2H), 7.54-7.60 (m, 3H).

It can be seen that the compounds of the invention are useful as inhibitors of Neutral endopeptidase (EC 3.4.24.11) activity and therefore useful in the treatment of diseases and conditions associated with Neutral endopeptidase (EC 3.4.24.11) activity such as the diseases disclosed herein.

It will be understood that the invention has been described by way of example only and modifications may be made whilst remaining within the scope and spirit of the invention.

The following are further embodiments of the invention:

Embodiment 1

A compound of Formula I:

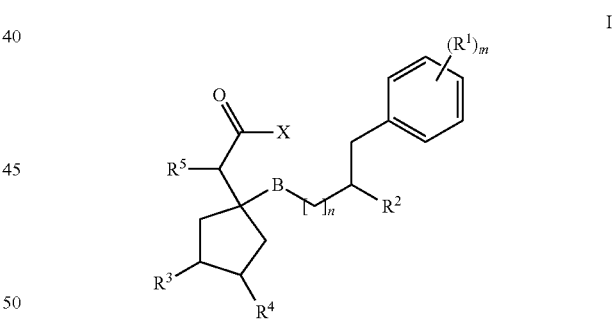

or a pharmaceutically acceptable salt thereof wherein:
R$^3$ and R$^4$ are H or R$^3$ and R$^4$ together with the carbon atoms to which they are attached form a phenyl ring;
n is 0 or 1;
R$^1$, for each occurrence, is independently halo, C$_{1-6}$alkyl, C$_{1-6}$alkoxy, hydroxy, heteroaryl or phenyl; wherein heteroaryl and phenyl can be optionally substituted with one or more substituents independently selected from halo, C$_{1-6}$alkyl, halo-C$_{1-6}$alkyl, cyano, C$_{1-6}$alkoxy, hydroxy and NR$^c$R$^d$; wherein R$^c$ and R$^d$ are independently H or C$_{1-6}$alkyl; or two adjacent R$^1$ groups form together with the carbon atoms to which they are attached a 5- or 6-membered heteroaryl ring optionally substituted with one or more substitutents independently selected from halo, C$_{1-6}$alkyl, halo-C$_{1-6}$alkyl, cyano, hydroxy and C$_{1-6}$alkoxy;

$R^2$ is $(CH_2)_pC(O)X^1$, or $(CH_2)_s$-heteroaryl; wherein heteroaryl is a mono or bicyclic heteroaryl ring containing from 5-10 ring members selected from carbon atoms and 1 to 5 heteroatoms, and each heteroatom is independently selected from O, N or S wherein S and N may be oxidized to various oxidation states and the heteroaryl is optionally substituted with one or more substituents independently selected from halo, $C_{1-6}$alkyl, halo-$C_{1-6}$alkyl, cyano, hydroxy, $C_{1-6}$alkoxy, carboxy and C(O)O—$C_{1-6}$alkyl;

$R^5$ is H, $C_{1-6}$alkyl or $C_{6-10}$aryl-$C_{1-6}$alkyl;

p is 0 or 1;

s is 0, 1, 2, 3 or 4;

m is 0, 1, 2, 3, 4 or 5;

X and $X^1$ are independently OH, O—$C_{1-6}$alkyl, O-benzyl or $NR^aR^b$ wherein $R^a$ and $R^b$ are independently H, $C_{1-6}$alkyl optionally substituted with one or more substituents independently selected from halo, hydroxy, $C_{1-6}$alkoxy and carboxy; or $R^a$ and $R^b$ together with the nitrogen atom to which they are attached form a 5- or 6-membered heterocyclyl optionally substituted with one or more substituents independently selected from $C_{9-6}$alkyl, halo, hydroxy, $C_{1-6}$alkoxy, carboxy, C(O)O—$C_{1-6}$alkyl and C(O)O-benzyl; and B is C(O)NH or NHC(O, with the proviso that the compound is not 4-(bisphenyl-4-yl)-3-(1-carboxymethyl)cyclopentanecarboxamido)butanoic acid, 4-([1,1'-biphenyl]-4-yl)-3-(1-(2-(benzyloxy)-2-oxoethyl)cyclopentanecarboxamido)butanoic acid or tert-butyl 4-([1,1'-biphenyl]-4-yl)-3-(1-(2-(benzyloxy)-2-oxoethyl)cyclopentanecarboxamido) butanoate.

Embodiment 2

The compound according to embodiment 1 of Formula II:

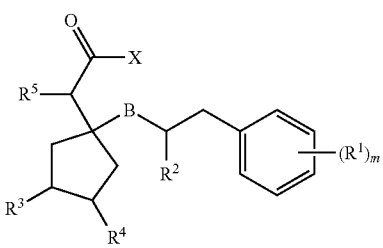

or a pharmaceutically acceptable salt thereof, wherein $R^1$, $R^2$, $R^3$, $R^4$, B, X and m have the definition of embodiment 1.

Embodiment 3

The compound according to embodiment 1 of Formula III:

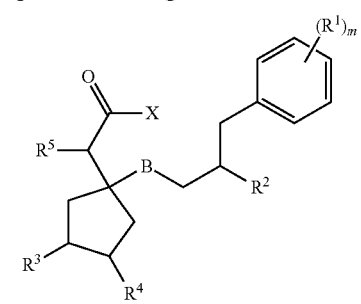

or a pharmaceutically acceptable salt thereof, wherein $R^1$, $R^2$, $R^3$, $R^4$, $R^5$, B, X and m have the definition of embodiment 1.

Embodiment 4

The compound of embodiment 1, 2 or 3 of Formula V wherein:

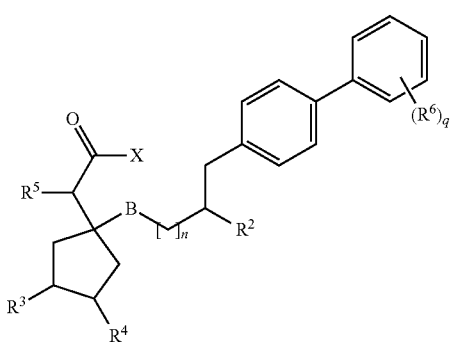

or a pharmaceutically acceptable salt thereof, wherein $R^2$, $R^3$, $R^4$, $R^5$, X, n have the definition of embodiment 1;

$R^6$ is halo, $C_{1-6}$alkyl, halo-$C_{1-6}$alkyl, cyano, $C_{1-6}$alkoxy, hydroxy or $NR^cR^d$; wherein $R^c$ and $R^d$ are independently H or $C_{1-6}$alkyl; and q is 0, 1, 2, 3, 4 or 5.

Embodiment 5

The compound of anyone of embodiments 1 to 4, having Formula VI:

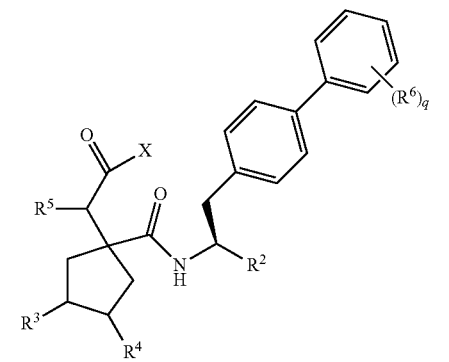

or a pharmaceutically acceptable salt thereof, wherein $R^2$, $R^3$, $R^4$, $R^5$, X, n have the definition of embodiment 1;

$R^6$ is halo, $C_{1-6}$alkyl, halo-$C_{1-6}$alkyl, cyano, $C_{1-6}$alkoxy or hydroxy; and q is 0, 1, 2, 3, 4 or 5.

Embodiment 6

The compound according to anyone of embodiments 1 to 5 wherein $R^2$ is $(CH_2)_pC(O)X^1$ or a pharmaceutically acceptable salt thereof.

Embodiment 7

The compound according to embodiment 6 wherein $R^2$ is $CH_2C(O)X^1$, n is 0, $X^1$ is $NR^aR^b$ or a pharmaceutically acceptable salt thereof.

Embodiment 8

The compound according to embodiment 6 wherein $R^2$ is $CH_2C(O)X^1$, n is 0, B is NHC(O) or a pharmaceutically acceptable salt thereof.

Embodiment 9

The compound according to anyone of embodiments 1 to 5 wherein $R^2$ is $(CH_2)_5$heteroaryl; wherein heteroaryl is a mono or bicyclic heteroaryl ring containing from 5-10 ring members selected from carbon atoms and 1 to 5 heteroatoms, and each heteroatom is independently selected from O, N or S wherein S and N may be oxidized to various oxidation states and the heteroaryl is optionally substituted with one or more substituents independently selected from halo, $C_{1-6}$alkyl, halo-$C_{1-6}$alkyl, cyano, hydroxy, $C_{1-6}$alkoxy, carboxy and C(O)—O$C_{1-6}$alkyl; or a pharmaceutically acceptable salt thereof.

Embodiment 10

The compound according to embodiment 9 wherein $R^2$ is tetrazole or imidazole, each of which is optionally substituted with one or more substitutents independently selected from halo, $C_{1-6}$alkyl, halo-$C_{1-6}$alkyl, cyano, hydroxy, $C_{1-6}$alkoxy, carboxy and C(O)—O$C_{1-6}$alkyl; or a pharmaceutically acceptable salt thereof.

Embodiment 11

The compound according to anyone of embodiments 1 to 10 wherein $R^3$ and $R^4$ are H, or a pharmaceutically acceptable salt thereof.

Embodiment 12

The compound according to anyone of embodiments 1 to 10 wherein $R^3$ and $R^4$ together with the carbon atom to which they are attached, form a phenyl ring, or a pharmaceutically acceptable salt thereof.

Embodiment 13

The compound according to any of embodiments 1, 5 and 11 to 12 wherein $R^2$ is $C(O)X^1$ or $(CH_2)_5$heteroaryl, wherein heteroaryl is optionally substituted with one or more substituents independently selected from halo, $C_{1-6}$alkyl, halo-$C_{1-6}$alkyl, cyano, hydroxy, $C_{1-6}$alkoxy, carboxy and C(O)O—$C_{1-6}$alkyl, or a pharmaceutically acceptable salt thereof.

Embodiment 14

A pharmaceutical composition comprising a compound according to any one of embodiments 1 to 13 or a pharmaceutically acceptable salt thereof and one or more pharmaceutically acceptable carriers.

Embodiment 15

A combination comprising: a compound according to any one of embodiments 1 to 13 or a pharmaceutically acceptable salt thereof and one or more therapeutically active agents selected from HMG-Co-A reductase inhibitor, an angiotensin receptor blocker, angiotensin converting enzyme Inhibitor, a calcium channel blocker, an endothelin antagonist, a renin inhibitor, a diuretic, an ApoA-1 mimic, an anti-diabetic agent, an obesity-reducing agent, an aldosterone receptor blocker, an endothelin receptor blocker, an aldosterone synthase inhibitors, a CETP inhibitor and a phophodiesterase type 5 (PDE5) inhibitor.

Embodiment 16

A method of inhibiting neutral endopeptidase EC. 3.4.24.11. activity in a subject in need thereof, comprising: administering to the subject a therapeutically effective amount of the compound according to any one of embodiments 1 to 13 or a pharmaceutically acceptable salt thereof.

Embodiment 17

A method of treating a disorder or a disease associated with neutral endopeptidase EC. 3.4.24.11. activity in a subject in need thereof, comprising: administering to the subject a therapeutically effective amount of the compound according to any one of embodiments 1 to 13 or a pharmaceutically acceptable salt thereof.

Embodiment 18

The method according to embodiment 17, wherein the disorder or the disease is selected from hypertension, pulmonary hypertension, pulmonary arterial hypertension, isolated systolic hypertension, resistant hypertension, peripheral vascular disease, heart failure, congestive heart failure, left ventricular hypertrophy, angina, renal insufficiency, renal failure, diabetic nephropathy, non-diabetic nephropathy, contrast induced nephropathy, nephroic syndrome, glomerulonephritis, scleroderma, glomerular sclerosis, proteinurea of primary renal disease, renal vascular hypertention, diabetic retinopathy and end-stage renal disease (ESRD), endothelial dysfunction, diastolic dysfunction, hypertrophic cardiomyopathy, diabetic cardiac myopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), renal failure, cyclical oedema, Menieres disease, hyperaldosteroneism hypercalciuria, ascites, glaucoma, menstrual disorders, preterm labor, pre-eclampsia, endometriosis, and reproductive disorders, asthma, obstructive sleep apnea, inflammation, leukemia, pain, epilepsy, affective disorders, depression, psychotic condition, dementia, geriatric confusion, obesity, gastrointestinal disorders, wound healing, septic shock, gastric acid secretion dysfunction, hyperreninaemia, cystic fibrosis, restenosis, type-2 diabetes, metabolic syndrome, diabetic complications, atherosclerosis, male and female sexual dysfunction.

Embodiment 19

The compound according to any one of embodiments 1 to 13, or a pharmaceutically acceptable salt thereof, for use as a medicament.

Embodiment 20

Use of the compound according to any one of embodiments 1 to 13, or a pharmaceutically acceptable salt thereof, for the treatment of a disorder or disease associated with neutral endopeptidase EC. 3.4.24.11. activity in a subject in need of such treatment.

Embodiment 21

The use of embodiment 20, wherein the disorder or disease is selected from hypertension, pulmonary hypertension, pulmonary arterial hypertension, isolated systolic hypertension, resistant hypertension, peripheral vascular disease, heart failure, congestive heart failure, left ventricular hypertrophy, angina, renal insufficiency, renal failure, diabetic nephropathy, non-diabetic nephropathy, contrast induced nephropathy, nephroic syndrome, glomerulonephritis, scleroderma, glomerular sclerosis, proteinurea of primary renal disease, renal vascular hypertention, diabetic retinopathy and end-stage renal disease (ESRD), endothelial dysfunction, diastolic dysfunction, hypertrophic cardiomyopathy, diabetic cardiac myopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), renal failure, cyclical oedema, Menieres disease, hyperaldosteroneism hypercalciuria, ascites, glaucoma, menstrual disorders, preterm labor, pre-eclampsia, endometriosis, and reproductive disorders, asthma, obstructive sleep apnea, inflammation, leukemia, pain, epilepsy, affective disorders, depression, psychotic condition, dementia, geriatric confusion, obesity, gastrointestinal disorders, wound healing, septic shock, gastric acid secretion dysfunction, hyperreninaemia, cystic fibrosis, restenosis, type-2 diabetes, metabolic syndrome, diabetic complications, atherosclerosis, male and female sexual dysfunction.

What is claimed is:

1. A compound of Formula I:

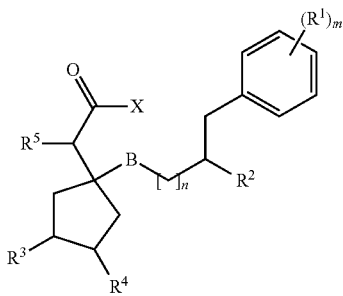

I or a pharmaceutically acceptable salt thereof wherein:

$R^3$ and $R^4$ are H or $R^3$ and $R^4$ together with the carbon atoms to which they are attached form a phenyl ring;

n is 0 or 1;

$R^1$ is phenyl or pyridinyl each of which is optionally substituted by one or more substituents selected from halo, $C_{1-6}$alkyl, halo-$C_{1-6}$alkyl, cyano, $C_{1-6}$alkoxy, hydroxy and $NR^cR^d$; wherein $R^c$ and $R^d$ are independently H or $C_{1-6}$alkyl, $R^2$ is $(CH_2)_pC(O)X^1$, or $(CH_2)_s$-heteroaryl; wherein heteroaryl is a mono or bicyclic heteroaryl ring containing from 5-10 ring members selected from carbon atoms and 1 to 5 heteroatoms, and each heteroatom is independently selected from O, N or S wherein S and N may be oxidized to various oxidation states and the hereroaryl is optionally substituted with one or more substituents independently selected from halo, $C_{1-6}$alkyl, halo-$C_{1-6}$alkyl, cyano, hydroxy, $C_{1-6}$alkoxy, carboxy and $C(O)O$—$C_{1-6}$alkyl;

$R^5$ is H, $C_{1-6}$alkyl or $C_{6-10}$aryl-$C_{1-6}$alkyl;

p is 0 or 1;

s is 0, 1, 2, 3 or 4;

m is 1;

X and $X^1$ are independently OH, O—$C_{1-6}$alkyl, O-benzyl or $NR^aR^b$ wherein $R^a$ and $R^b$ are independently H, $C_{1-6}$alkyl optionally substituted with one or more substituents independently selected from halo, hydroxy, $C_{1-6}$alkoxy and carboxy; or $R^a$ and $R^b$ together with the nitrogen atom to which they are attached form a 5- or 6-membered heterocyclyl optionally substituted with one or more substituents independently selected from $C_{1-6}$alkyl, halo, hydroxy, $C_{1-6}$alkoxy, carboxy, C(O)O—$C_{1-6}$alkyl and C(O)O-benzyl; and B is C(O)NH or NHC(O), with the proviso that the compound is not 4-(bisphenyl-4-yl)-3-(1-carboxymethyl) cyclopentanecarboxamido)butanoic acid, 4-([1,1'-biphenyl]-4-yl)-3-(1-(2-(benzyloxy)-2-oxoethyl) cyclopentanecarboxamido)butanoic acid or tert-butyl 4-([1,1'-biphenyl]-4-yl)-3-(1-(2-(benzyloxy)-2-oxoethyl)cyclopentanecarboxamido)butanoate.

2. The compound according to claim 1 of Formula II:

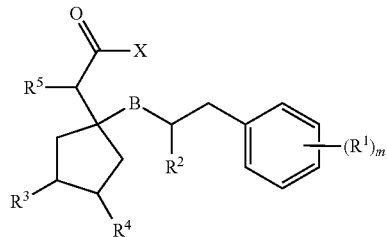

II or a pharmaceutically acceptable salt thereof, wherein $R^1$, $R^2$, $R^3$, $R^4$, $R^5$, B, X and m have the definition of claim 1.

3. The compound according to claim 1 of Formula III:

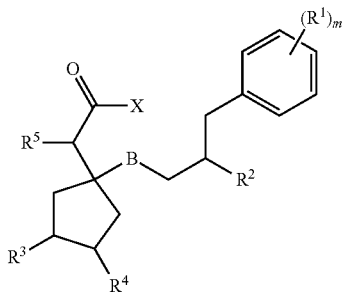

III or a pharmaceutically acceptable salt thereof, wherein $R^1$, $R^2$, $R^3$, $R^4$, $R^5$, B, X and m have the definition of claim 1.

4. The compound of claim 1 of Formula V wherein:

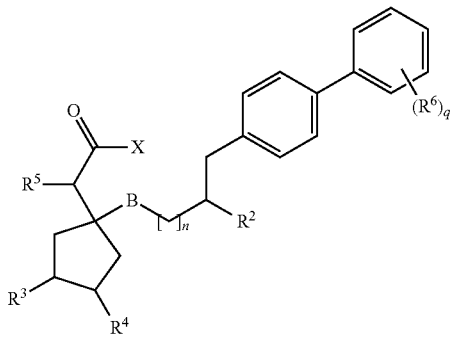

V or a pharmaceutically acceptable salt thereof, wherein $R^2$, $R^3$, $R^4$, $R^5$, X, n have the definition of claim 1;

$R^6$ is halo, $C_{1-6}$alkyl, halo-$C_{1-6}$alkyl, cyano, $C_{1-6}$alkoxy, hydroxy or $NR^cR^d$; wherein $R^c$ and $R^d$ are independently H or $C_{1-6}$alkyl; and q is 0, 1, 2, 3, 4 or 5.

5. The compound of claim 1, having Formula VI:

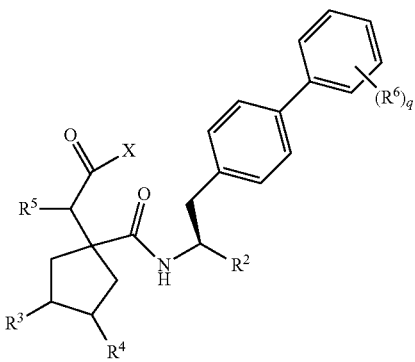

or a pharmaceutically acceptable salt thereof, wherein $R^2$, $R^3$, $R^4$, $R^5$, X, n have the definition of claim 1;
$R^6$ is halo, $C_{1-6}$alkyl, halo-$C_{1-6}$alkyl, cyano, $C_{1-6}$alkoxy or hydroxy; and
q is 0, 1, 2, 3, 4 or 5.

6. The compound according to claim 1 wherein $R^2$ is $(CH_2)_pC(O)X^1$ or a pharmaceutically acceptable salt thereof.

7. The compound according to claim 6 wherein $R^2$ is $CH_2C(O)X^1$, n is 0, $X^1$ is $NR^aR^b$ or a pharmaceutically acceptable salt thereof.

8. The compound according to claim 6 wherein $R^2$ is $CH_2C(O)X^1$, n is 0, B is NHC(O) or a pharmaceutically acceptable salt thereof.

9. The compound according to claim 1 wherein $R^2$ is $(CH_2)_s$-heteroaryl; wherein heteroaryl is a mono or bicyclic heteroaryl ring containing from 5-10 ring members selected from carbon atoms and 1 to 5 heteroatoms, and each heteroatom is independently selected from O, N or S wherein S and N may be oxidized to various oxidation states and the heroaryl is optionally substituted with one or more substituents independently selected from halo, $C_{1-6}$alkyl, halo-$C_{1-6}$alkyl, cyano, hydroxy, $C_{1-6}$alkoxy, carboxy and C(O)—O$C_{1-6}$alkyl; or a pharmaceutically acceptable salt thereof.

10. The compound according to claim 9 wherein $R^2$ is tetrazole or imidazole, each of which is optionally substituted with one or more substitutents independently selected from halo, $C_{1-6}$alkyl, cyano, hydroxy, $C_{1-6}$alkoxy, carboxy and C(O)—O$C_{1-6}$alkyl;
or a pharmaceutically acceptable salt thereof.

11. The compound according to claim 1 wherein $R^3$ and $R^4$ are H, or a pharmaceutically acceptable salt thereof.

12. The compound according to claim 1 wherein $R^3$ and $R^4$ together with the carbon atom to which they are attached, form a phenyl ring, or a pharmaceutically acceptable salt thereof.

13. The compound according to claim 1 wherein $R^2$ is $C(O)X^1$ or $(CH_2)_s$-heteroaryl, wherein heteroaryl is optionally substituted with one or more substituents independently selected from halo, $C_{1-6}$alkyl, cyano, hydroxy, $C_{1-6}$alkoxy, carboxy and C(O)O—$C_{1-6}$alkyl, or a pharmaceutically acceptable salt thereof.

14. A pharmaceutical composition comprising a compound according to claims 1 or a pharmaceutically acceptable salt thereof and one or more pharmaceutically acceptable carriers.

15. A combination comprising: a compound according to claim 1 or a pharmaceutically acceptable salt thereof and one or more therapeutically active agents selected from HMG-Co-A reductase inhibitor, an angiotensin receptor blocker, angiotensin converting enzyme Inhibitor, a calcium channel blocker, an endothelin antagonist, a renin inhibitor, a diuretic, an ApoA-I mimic, an anti-diabetic agent, an obesity-reducing agent, an aldosterone receptor blocker, an endothelin receptor blocker, an aldosterone synthase inhibitors, a CETP inhibitor and a phophodiesterase type 5 (PDE5) inhibitor.

16. A method of inhibiting neutral endopeptidase (EC. 3.4. 24.11.) activity in a subject in need thereof, comprising: administering to the subject a therapeutically effective amount of the compound according to claim 1 or a pharmaceutically acceptable salt thereof.

17. The method of treating a disease or disorder associated with neutral endopeptidase (EC 3.4.24.11) activity in a subject in need thereof, comprising: administering to the subject a therapeutically effective amount of the compound according to claim 1 or a pharmaceutically acceptable salt thereof, wherein the disorder or disease is selected from hypertension, pulmonary hypertension, pulmonary arterial hypertension, isolated systolic hypertension, resistant hypertension, peripheral vascular disease, heart failure, congestive heart failure, left ventricular hypertrophy, angina, renal insufficiency, renal failure, diabetic nephropathy, non-diabetic nephropathy, contrast induced nephropathy, nephroic syndrome, scleroderma, glomerular sclerosis, proteinurea of primary renal disease, renal vascular hypertention, diabetic retinopathy and end-stage renal disease (ESRD), endothelial dysfunction, diastolic dysfunction, hypertrophic cardiomyopathy, diabetic cardiac myopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), renal failure, cyclical oedema, glaucoma, preterm labor, wound healing, septic shock, gastric acid secretion dysfunction, restenosis, type-2 diabetes, metabolic syndrome, atherosclerosis, male and female sexual dysfunction.

18. A method of treating a disorder or a disease associated with neutral endopeptidase (EC. 3.4. 24.11.) activity in a subject in need thereof, comprising: administering to the subject a therapeutically effective amount of the compound according to claim 1, or a pharmaceutically acceptable salt thereof wherein the disorder is selected from hypertension, pulmonary hypertension, isolated systolic hypertension, resistant hypertension, peripheral vascular disease, congestive heart failure or pulmonary arterial hypertension.

* * * * *